United States Patent
Kato et al.

(10) Patent No.: US 10,295,525 B2
(45) Date of Patent: May 21, 2019

(54) IMAGE GENERATION DEVICE, IMAGE GENERATION METHOD, RECORDING MEDIUM, AND PROCESSING METHOD

(71) Applicant: Panasonic Intellectual Property Management Co., Ltd., Osaka (JP)

(72) Inventors: Yumiko Kato, Osaka (JP); Taichi Sato, Kyoto (JP); Yoshihide Sawada, Kyoto (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 144 days.

(21) Appl. No.: 15/450,548

(22) Filed: Mar. 6, 2017

(65) Prior Publication Data
US 2017/0270662 A1 Sep. 21, 2017

(30) Foreign Application Priority Data

Mar. 18, 2016 (JP) ................................ 2016-056168
Nov. 7, 2016 (JP) ................................ 2016-217674

(51) Int. Cl.
*G01N 33/483* (2006.01)
*H04N 5/225* (2006.01)
(Continued)

(52) U.S. Cl.
CPC ......... *G01N 33/4833* (2013.01); *G01B 11/24* (2013.01); *G01N 21/84* (2013.01); *G02B 21/06* (2013.01); *G02B 21/367* (2013.01); *G06T 7/571* (2017.01); *H04N 5/2256* (2013.01); *H04N 5/23212* (2013.01); *G01B 2210/52* (2013.01); *G06T 2207/10016* (2013.01);
(Continued)

(58) Field of Classification Search
CPC ...... G02B 21/06; G02B 21/367; G06T 7/571; G06T 5/003; G06T 5/50; G01N 21/84; G01N 33/4833; H04N 5/2256; H04N 5/23212; G01B 11/24; G06K 9/0014; G06K 9/4633
USPC ............ 382/154, 103; 348/79, 50, 46, 222.1
See application file for complete search history.

(56) References Cited

U.S. PATENT DOCUMENTS 9,767,341 B2 * 9/2017 Ozcan .................. G06K 9/0014
2003/0206653 A1 * 11/2003 Katayama .............. G06K 9/209
382/154

(Continued)

FOREIGN PATENT DOCUMENTS

JP 2013-101512 5/2013

*Primary Examiner* — Michael E Teitelbaum
*Assistant Examiner* — Sean N. Haiem
(74) *Attorney, Agent, or Firm* — Wenderoth, Lind & Ponack, L.L.P.

(57) ABSTRACT

An image generation device generates a plurality of reference in-focus images of an object placed on a surface of an image sensor by using a plurality of images captured by the image sensor using sensor pixels when the object is irradiated with light by a plurality of illuminators. Each of the reference in-focus images is an in-focus image corresponding to one of a plurality of virtual reference focal planes that are located between the image sensor and the plurality of illuminators. The plurality of reference focal planes pass through the object and are spaced apart from one another. The image generation device generates a three-dimensional image of the object by using the reference in-focus images and displays the three-dimensional image on a display screen.

12 Claims, 37 Drawing Sheets

(51) Int. Cl.
  *H04N 5/232* (2006.01)
  *G01B 11/24* (2006.01)
  *G06T 7/571* (2017.01)
  *G02B 21/06* (2006.01)
  *G01N 21/84* (2006.01)
  *G02B 21/36* (2006.01)

(52) U.S. Cl.
  CPC ............... *G06T 2207/10024* (2013.01); *G06T 2207/10056* (2013.01); *G06T 2207/10152* (2013.01); *G06T 2207/30024* (2013.01); *G06T 2207/30044* (2013.01)

(56) References Cited

U.S. PATENT DOCUMENTS

| | | | |
|---|---|---|---|
| 2012/0098950 A1* | 4/2012 | Zheng | G02B 21/06 348/79 |
| 2012/0223217 A1* | 9/2012 | Zheng | B01L 3/508 250/215 |
| 2014/0133702 A1* | 5/2014 | Zheng | G06K 9/00624 382/103 |
| 2015/0124073 A1* | 5/2015 | Fujishima | G02B 21/16 348/79 |

* cited by examiner

FIG. 6

| FILE ID | ILLUMINATOR POSITION INFORMATION | | |
|---|---|---|---|
| | x | y | z |
| ⋮ | ⋮ | ⋮ | ⋮ |
| 0000101 | 0360 | −1020 | 800 |
| 0000102 | 0420 | −1020 | 800 |
| 0000103 | 0480 | −1020 | 800 |
| ⋮ | ⋮ | ⋮ | ⋮ |

FIG. 32

| MODEL ID | NUMBER OF CELLS | CULTURE PERIOD | SCHEMATIC DIAGRAM |
|---|---|---|---|
| 0001 | 1 | 0 TO ta | |
| 0002 | 2 | ta TO tb | |
| 0003 | 3 | tb TO tc | |
| 0004 | 4 | tc TO td | |
| ⋮ | ⋮ | ⋮ | ⋮ |

FIG. 33

| NUMBER OF CELLS IN EMBRYO | NUMBER OF CANDIDATE OPTIMUM FOCAL PLANES | LARGEST NUMBER OF CELLS POSSIBLY INCLUDED IN OPTIMUM SECTIONAL IMAGE AT OPTIMUM FOCAL PLANE |
|---|---|---|
| 1 | 1 | 1 |
| 2 | 1 | 2 |
| 3 | 1 | 3 |
| 4 | 2 | 4 |
| 5 | 2 | 4 |
| 6 | 2 | 5 |
| 7 | 2 | 5 |
| 8 | 2 | 6 |
| ⋮ | ⋮ | ⋮ |

IMAGE GENERATION DEVICE, IMAGE GENERATION METHOD, RECORDING MEDIUM, AND PROCESSING METHOD

BACKGROUND

1. Technical Field

The present disclosure relates to a technique for use in lensless microscopes to generate an image of an object by using a virtual focal plane on the basis of a plurality of images captured by using a plurality of light sources.

2. Description of the Related Art

There is a need for continuous observation of cultured cells without staining the cells in many fields in which cultured cells are used for medical and industrial purposes, such as production of cells for use in medical treatment and investigation of the efficacy of a medicine. However, since most cells are colorless and transparent, the three-dimensional structure of cultured cells is not clearly revealed by imaging with optical microscopes using transmitted light.

Japanese Unexamined Patent Application Publication No. 2013-101512 discloses a method for generating an in-focus image (virtual sectional image) at a plane that is not parallel to an objective lens from many images for which the focal plane is parallel to the objective lens and the focal point is at different heights with respect to an object (i.e., many images captured by changing the focus along a height direction of the object) in order to evaluate the sectional profile of cells.

Continuous observation of cultured cells is carried out in a limited space, such as an incubator, in order to maintain a humid environment for culturing the cells. To enable observation in a limited humid space, U.S. Patent Application Publication No. 2014/0133702 discloses a lensless microscope that enables observation of minute cells without using lenses. U.S. Patent Application Publication No. 2014/0133702 discloses a method for increasing the resolution by superimposing a plurality of images captured under illumination from a plurality of different positions (ptychography).

According to the method disclosed in Japanese Unexamined Patent Application Publication No. 2013-101512, since a partial image is extracted from each image at a corresponding one of the heights after imaging and then the extracted partial images are linked together, the joints of the partial images become discontinuous. Consequently, the image quality of the virtual sectional image degrades due to discontinuity. In addition, if processing for blurring is performed on the discontinuous portions to decrease the degradation of image quality due to discontinuity, the sharpness of the virtual sectional image decreases.

SUMMARY

One non-limiting and exemplary embodiment provides an image generation device and the like capable of generating an image of an object by using high-quality in-focus images that are generated for respective virtual focal planes by using a plurality of captured images.

In one general aspect, the techniques disclosed here feature an image generation device including a plurality of illuminators; an image sensor including a plurality of sensor pixels, the image sensor having a surface on which an object is placed; and a control circuit that generates a plurality of reference in-focus images each corresponding to one of a plurality of virtual reference focal planes that are located between the image sensor and the plurality of illuminators and generates a three-dimensional image of the object by using the plurality of reference in-focus images, wherein the image sensor captures a plurality of images, each of the plurality of images being captured by using pixel values based on light received by the plurality of sensor pixels when a corresponding one of the plurality of illuminators irradiates the object with the light, wherein each of the plurality of reference in-focus images includes a plurality of in-focus pixels, and wherein the control circuit (a1) obtains the plurality of images captured by the image sensor, (a2) obtains information regarding the plurality of virtual reference focal planes that pass through the object and are spaced apart from one another, (a3) generates the plurality of reference in-focus images by obtaining pixel values of the sensor pixels corresponding to the plurality of in-focus pixels of the plurality of reference in-focus images by using the information regarding the plurality of virtual reference focal planes and the plurality of images, (a4) extracts an outline of the object by using a reference in-focus image including an outline of the object having the highest contrast from among the plurality of reference in-focus images, (a5) identifies a three-dimensional outline of the object on the basis of the extracted outline of the object, (a6) generates a plurality of reference sectional images of the object by removing a region outside the three-dimensional outline from the plurality of reference in-focus images, and (a7) generates the three-dimensional image of the object by using the plurality of reference sectional images and causes the three-dimensional image to be displayed on a display screen.

According to embodiments of the present disclosure, an image of an object is successfully generated by using high-quality in-focus images that are generated for respective virtual focal planes by using a plurality of captured images.

It should be noted that general or specific embodiments may be implemented as a system, a method, an integrated circuit, a computer program, a computer-readable recording medium, or any selective combination of a device, a system, a method, an integrated circuit, a computer program, and a computer-readable recording medium. Examples of the computer-readable recording medium include nonvolatile recording media, such as a Compact Disc-Read Only Memory (CD-ROM).

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 6 is a diagram illustrating an example of information stored in a storage unit according to the first embodiment;

FIG. 32 is a diagram illustrating an example of early embryo models stored in a first memory;

FIG. 33 is a diagram illustrating an example of an optimum section setting table stored in the first memory;

DETAILED DESCRIPTION

Figure 1:
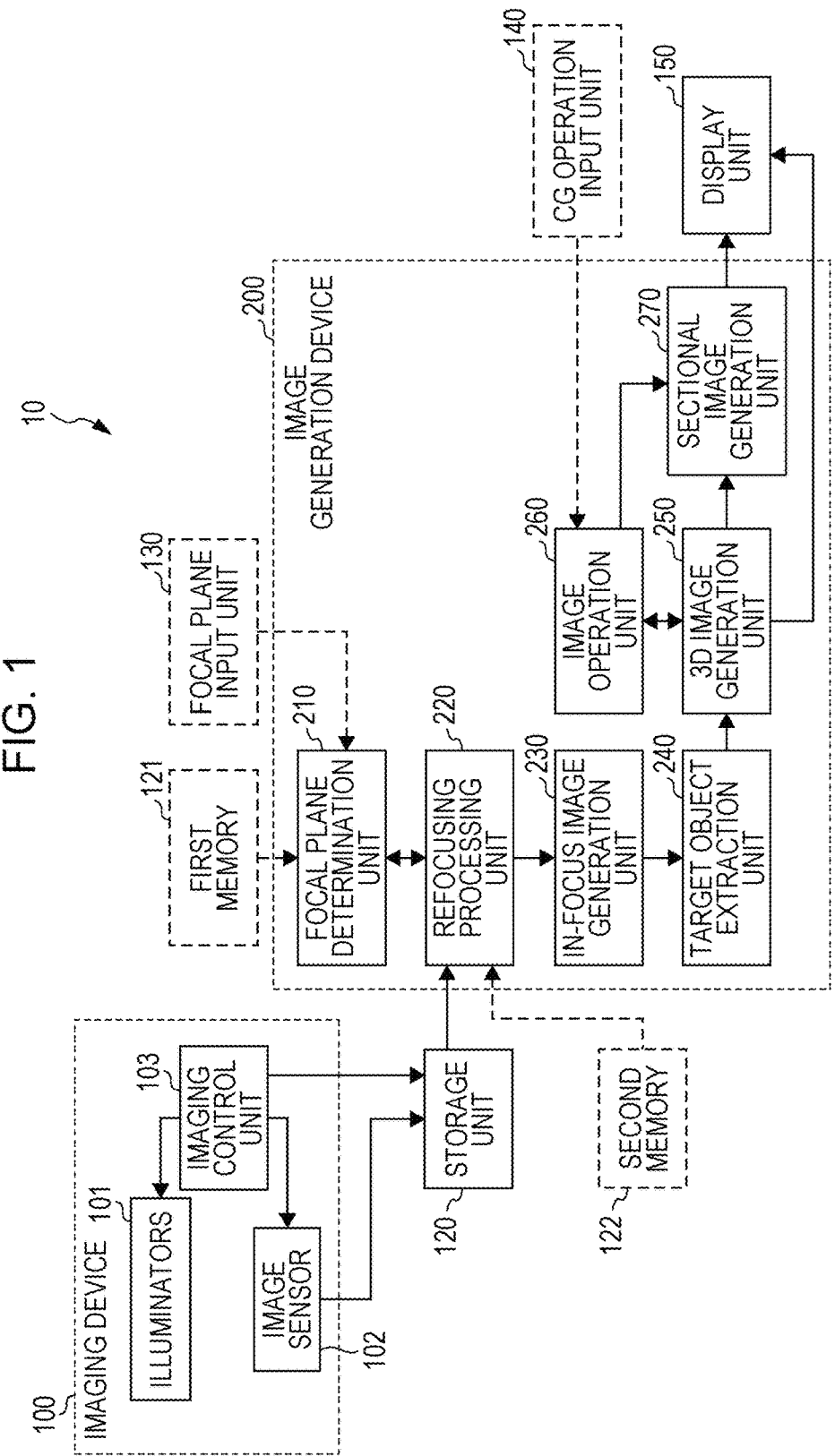
FIG. 1 is a block diagram illustrating an example of the functional configuration of an image generation system according to a first embodiment.

An image generation device according to an aspect of the present disclosure includes a plurality of illuminators; an image sensor including a plurality of sensor pixels, the image sensor having a surface on which an object is placed; and a control circuit that generates a plurality of reference in-focus images each corresponding to one of a plurality of virtual reference focal planes that are located between the image sensor and the plurality of illuminators and generates a three-dimensional image of the object by using the plurality of reference in-focus images, wherein the image sensor captures a plurality of images, each of the plurality of images being captured by using pixel values based on light received by the plurality of sensor pixels when a corresponding one of the plurality of illuminators irradiates the object with the light, wherein each of the plurality of reference in-focus images includes a plurality of in-focus pixels, and wherein the control circuit (a1) obtains the plurality of images captured by the image sensor, (a2) obtains information regarding the plurality of virtual reference focal planes that pass through the object and are spaced apart from one another, (a3) generates the plurality of reference in-focus images by obtaining pixel values of the sensor pixels corresponding to the plurality of in-focus pixels of the plurality of reference in-focus images by using the information regarding the plurality of virtual reference focal planes and the plurality of images, (a4) extracts an outline of the object by using a reference in-focus image including an outline of the object having the highest contrast from among the plurality of reference in-focus images, (a5) identifies a three-dimensional outline of the object on the basis of the extracted outline of the object, (a6) generates a plurality of reference sectional images of the object by removing a region outside the three-dimensional outline from the plurality of reference in-focus images, and (a7) generates the three-dimensional image of the object by using the plurality of reference sectional images and causes the three-dimensional image to be displayed on a display screen.

According to this aspect, a plurality of in-focus images (i.e., reference in-focus images) are successfully generated for a plurality of focal planes that pass through an object, and a three-dimensional (3D) image of the object is successfully generated by using the generated in-focus images. The use of in-focus images for a plurality of focal planes that pass through an object enables a 3D image of the object to be displayed three-dimensionally including contents of the object even if the object is translucent or transparent. In addition, since the in-focus images are generated for the plurality of focal planes instead of the entire region of the object, a processing amount required for generation of the 3D image of the object is successfully reduced. Note that the surface of the image sensor on which the object is placed includes a surface above sensor pixels of the image sensor.

In the image generation device according to the aspect of the present disclosure, the control circuit may select a section of the object in the displayed three-dimensional image of the object in accordance with an instruction externally input, may generate an image of the selected section of the object by using pixel values of a plurality of pixels of the plurality of reference in-focus images, the image of the selected section of the object including a plurality of section pixels, and may calculate a pixel value of each of the plurality of section pixels of the image of the selected section of the object by using a pixel value of a pixel of the reference in-focus image located at the section pixel or by using pixel values of pixels of the reference in-focus images located near the section pixel.

According to this aspect, a given section is successfully selected by using the 3D image of the object and an image of the selected section is successfully displayed. Since pixel values of a plurality of section pixels of the sectional image of the object are calculated by using pixel values of the respective pixels of the reference in-focus image that are located at the section pixels or pixel values of pixels of the reference in-focus image near the respective section pixels, the sectional image of the object can be a sharp image in which discontinuity and blur are reduced.

In the image generation device according to the aspect of the present disclosure, the pixels of the reference in-focus images located near the section pixel that are used to calculate the pixel value of the section pixel may be pixels of the reference in-focus images for two virtual reference focal planes having the section pixel interposed therebetween. According to this aspect, since a pixel value of each section pixel is calculated by using pixels of reference in-focus images at respective reference focal planes located on the respective sides of the section pixel, the pixel value can be highly accurate.

In the image generation device according to the aspect of the present disclosure, the control circuit may generate a preview sectional image representing a section of the object for preview and cause the preview sectional image to be displayed on the display screen, the preview sectional image including a plurality of pixels, and the control circuit may generate the preview sectional image by using, as a pixel value of each of the plurality of pixels of the preview sectional image, a pixel value of a pixel of the reference in-focus image located at the pixel of the preview sectional image. According to this aspect, the user is allowed to select a to-be-displayed section of the object with reference to a preview sectional image. In addition, since a pixel value of each pixel of the reference in-focus image is used as a pixel value of a corresponding pixel of the preview sectional image without processing the pixel value, the preview sectional image is generated easily.

In the image generation device according to the aspect of the present disclosure, the control circuit may calculate the pixel value of each of the plurality of in-focus pixels by using a pixel value of each of the sensor pixels that satisfy a relationship in which the position of the illuminator, the position of the in-focus pixel, and the position of the sensor pixel are on a line. According to this aspect, for each pixel of an in-focus image at the focal plane, pixel values of the plurality of photographic images corresponding to the pixel can be reflected. Thus, a high-quality in-focus image of the object is successfully generated.

In the image generation device according to the aspect of the present disclosure, the object may be an embryo, the outline of the embryo included in the reference in-focus image may be circular, and the three-dimensional outline of the embryo may be spherical. In this aspect, cells included in an embryo are seen through from outside the embryo. The image sensor can capture images of the embryo and cells irradiated with light by respective illuminators. An embryo having such properties is suitably used for image generation performed by the image generation device.

An image generation method according to an aspect of the present disclosure is an image generation method for generating an image of an object placed on an image sensor, including (b1) capturing a plurality of images, each of the plurality of images being captured by using pixel values based on light received by a plurality of sensor pixels of the image sensor when a corresponding one of a plurality of illuminators irradiates the object with the light; (b2) setting a plurality of virtual reference focal planes between the image sensor and the plurality of illuminators, the plurality of virtual reference focal planes passing through the object and being spaced apart from one another; (b3) generating a plurality of reference in-focus images each corresponding to one of the plurality of virtual reference focal planes by obtaining pixel values of the sensor pixels corresponding to a plurality of in-focus pixels of the plurality of reference in-focus images by using information regarding the plurality of virtual reference focal planes and the plurality of captured images; (b4) extracting an outline of the object by using a reference in-focus image including an outline of the object having the highest contrast from among the plurality of reference in-focus images; (b5) identifies a three-dimensional outline of the object on the basis of the extracted outline of the object; (b6) generating a plurality of reference sectional images of the object by removing a region outside the three-dimensional outline of the object from the plurality of reference in-focus images; and (b7) generating a three-dimensional image of the object by using the plurality of reference sectional images and causing the three-dimensional image to be displayed on a display screen, at least one of (b1) to (b7) being performed by a control circuit.

The image generation method according to the aspect of the present disclosure may further include (c1) selecting a section of the object in the three-dimensional image of the object; (c2) generating an image of the selected section of the object by using pixel values of a plurality of pixels of the plurality of reference in-focus images, the image of the selected section of the object including a plurality of section pixels; and (c3) calculating a pixel value of each of the plurality of section pixels of the image of the selected section of the object by using a pixel value of a pixel of the reference in-focus image located at the section pixel or by using pixel values of pixels of the reference in-focus images located near the section pixel.

Further, in the image generation method according to the aspect of the present disclosure, in the calculating of a pixel value of each of the plurality of section pixels, pixels of the reference in-focus images for two virtual reference focal planes having the section pixel interposed therebetween may be used as the pixels of the reference in-focus images located near the section pixel.

The image generation method according to the aspect of the present disclosure may further include (d1) generating a preview sectional image representing a section of the object for preview and causing the preview sectional image to be displayed on the display screen, the preview sectional image including a plurality of pixels, and in the generating of the preview sectional image, as a pixel value of each of the plurality of pixels of the preview sectional image, a pixel value of a pixel of the reference in-focus image located at the pixel of the preview sectional image may be used.

In the image generation method according to the aspect of the present disclosure, the pixel value of each of the plurality of in-focus pixels may be calculated by using a pixel value of each of the sensor pixels that satisfy a relationship in which the position of the illuminator, the position of the in-focus pixel, and the position of the sensor pixel are on a line.

In the image generation device according to the aspect of the present disclosure, the object may be an embryo, the outline of the embryo included in the reference in-focus image may be circular, and the three-dimensional outline of the embryo may be spherical.

A recording medium according to an aspect of the present disclosure is a recording medium storing a control program that causes a device including a processor to perform a process, the recording medium being nonvolatile and computer-readable, the process including (e1) capturing, using an image sensor, a plurality of images of an object placed on the image sensor, each of the plurality of images being captured by using pixel values based on light received by a plurality of sensor pixels of the image sensor when a corresponding one of a plurality of illuminators irradiates the object with the light; (e2) setting a plurality of virtual reference focal planes between the image sensor and the plurality of illuminators, the plurality of virtual reference focal planes passing through the object and being spaced apart from one another between the image sensor and the plurality of illuminators; (e3) generating a plurality of reference in-focus images each corresponding to one of the plurality of virtual reference focal planes by obtaining pixel values of the sensor pixels corresponding to a plurality of in-focus pixels of the plurality of reference in-focus images by using information regarding the plurality of virtual reference focal planes and the plurality of captured images; (e4) extracting an outline of the object by using a reference in-focus image including an outline of the object having the highest contrast from among the plurality of reference in-focus images; (e5) identifying a three-dimensional outline of the object on the basis of the extracted outline of the object; (e6) generating a plurality of reference sectional images of the object by removing a region outside the three-dimensional outline of the object from the plurality of reference in-focus images; and (e7) generating a three-dimensional image of the object by using the plurality of reference sectional images and causing the three-dimensional image to be displayed on a display screen.

An image generation device according to another aspect of the present disclosure includes a plurality of illuminators; an image sensor having a surface on which an object is placed; and a control circuit that generates an in-focus image of the object at a virtual focal plane located between the image sensor and the plurality of illuminators, wherein the object includes a first object and one or more second objects included in the first object, and wherein the control circuit (a1) obtains a plurality of images captured by the image sensor, each of the plurality of images being captured when a corresponding one of the plurality of illuminators irradiates the object with light, (a2) identifies feature points of the one or more second objects included in each of the plurality of images that have been obtained, (a3) calculates three-dimensional positions of the feature points of the one or more second objects on the basis of the positions of the feature points of the one or more second objects in each of the plurality of images and the positions of the plurality of illuminators, and (a4) determines a section of the first object including a largest number of feature points of second objects among the one or more second objects, generates an in-focus image of the section, and causes the in-focus image of the section to be displayed on a display screen.

According to this aspect, the image generation device selects a section including a largest number of feature points of the second object(s) included in the first object and displays an in-focus image of the selected section. The displayed in-focus image of the section successfully shows many features inside the first object. Accordingly, the image generation device is capable of automatically generating and providing useful information to the user.

In the image generation device according to the other aspect of the present disclosure, the control circuit may associate with each other the feature points of each of the one or more second objects in the plurality of images when the feature point of the second object is identified. According to this aspect, corresponding feature points of the second object are identified in captured images. For example, when two or more feature points are set, a positional relationship between corresponding feature points in captured images can be calculated. Consequently, when the first object includes two or more second objects, the image generation device can include more second objects in an in-focus image of the section by associating corresponding feature points of each of the second objects.

In the image generation device according to the other aspect of the present disclosure, the first object may be a spherical embryo, the second object may be a cell, and the feature point may be a center point of the cell. In this aspect, cells included in an embryo are seen through from outside the embryo. The image sensor can capture images of the embryo and cells irradiated with light by respective illuminators. An embryo having such properties is suitably used for image generation performed by the image generation device.

An image generation method according to another aspect of the present disclosure is an image generation method for generating an image of an object placed on an image sensor by using an in-focus image at a virtual focal plane located between the image sensor and a plurality of illuminators, the object including a first object and one or more second objects included in the first object, the image generation method including (b1) obtaining a plurality of images captured by sequentially causing the plurality of illuminators to irradiate the object with light; (b2) identifies feature points of the one or more second objects included in each of the plurality of images that have been obtained; (b3) calculating three-dimensional positions of the feature points of the one or more second objects on the basis of positions of the feature points of the one or more second objects in the plurality of images and the positions of the plurality of illuminators; and (b4) determining a section of the first object including a largest number of feature points of second objects among the one or more second objects, generating an in-focus image of the section, and causing the in-focus image of the section to be displayed on a display screen, at least one of (b1) to (b4) being performed by a control circuit.

In the image generation method according to the other aspect of the present disclosure, the feature points of each of the one or more second objects in the plurality of images may be associated with each other when the feature point of the second object is identified.

In the image generation method according to the other aspect of the present disclosure, the first object may be a spherical embryo, the second object may be a cell, and the feature point may be a center point of the cell.

A recording medium according to another aspect of the present disclosure is a recording medium storing a control program causing a device including a processor to perform a process, the recording medium being nonvolatile and computer-readable, the process including (c1) obtaining a plurality of images, each of the plurality of images being captured by an image sensor when a corresponding one of a plurality of illuminators irradiates an object with light, the object being placed on the image sensor and including a first object and one or more second objects included in the first object; (c2) identifying feature points of the one or more second objects in each of the plurality of images that have been obtained; (c3) calculating three-dimensional positions of the feature points of the one or more second objects on the basis of positions of the feature points of the one or more second objects in the plurality of images and the positions of the plurality of illuminators; and (c4) determining a section of the first object including a largest number of feature points of second objects among the one or more second objects, generating an in-focus image of the section, and causing the in-focus image of the section to be displayed on a display screen.

In the recording medium according to the other aspect of the present disclosure, the feature points of each of the one or more second objects in the plurality of captured images may be associated with each other when the feature point of the second object is identified.

In addition, in the recording medium according to the other aspect of the present disclosure, the first object may be a spherical embryo, the second object may be a cell, and the feature point may be a center point of the cell.

It should be noted that general or specific embodiments of these image generation devices and image generation methods may be implemented as a device, a method, an integrated circuit, a computer program, a computer-readable recording medium such as a CD-ROM, or any selective combination thereof. For example, the image generation methods may be implemented by a processor such as a central processing unit (CPU) or a micro processing unit (MPU); a circuit such as a large scale integration (LSI) chip; an integrated circuit (IC) card; or a discrete module, or the like.

In addition, processes according to embodiments may be implemented by a software program or digital signals based on the software program. For example, the software program and the digital signals based on the software program may be stored on a computer-readable recording medium, for example, a flexible disk, a hard disk, a CD-ROM, an MO, a Digital Versatile Disc (DVD), a DVD-ROM, DVD-random access memory (RAM), BD (Blu-ray (registered trademark) Disc), or a semiconductor memory. In addition, the software program and the digital signals based on the software program may be transmitted via an electrical communication line, a wireless or wired communication line, a network such as the Internet, data broadcasting, or the like. In addition, the software program and the digital signals based on the software program may be transferred to another independent computer system after being recorded on a recorded medium or via a network or the like and may be executed by the other independent computer system.

Image generation systems according to an aspect of the present disclosure will be described below with reference to the drawings. Note that each embodiment to be described below provides general or specific examples. The values, shapes, components, arrangement and connection of the components, steps, the order of steps, etc., described in the following embodiments are merely illustrative and are not intended to limit the claims. Among the components in the following embodiments, a component not recited in any of the independent claims indicating the most generic concept is described as an optional component. In the following description of the embodiments, the expression accompanying "substantially", such as substantially parallel or substantially orthogonal, is sometimes used. For example, the expression "substantially parallel" not only indicates the state of being completely parallel but also indicates the state of being substantially parallel, that is, the state of allowing an error of several percent, for example. The same applies to other expressions accompanying "substantially".

First Embodiment

An image generation system including an image generation device according to a first embodiment generates an image of an object at a virtual focal plane located between a plurality of illuminators and an image sensor by using a plurality of images each of which is captured by imaging the object when the object placed on the image sensor is irradiated with light by a corresponding one of a plurality of illuminators. The image generated by using the plurality of captured images is also referred to as an in-focus image or a refocusing image, and generating an image of an object at a virtual focal plane by using captured images is also referred to as a refocusing process. During the refocusing process, pixels on the virtual focal plane may be determined by using pixels of captured images. The image generation system generates in-focus images at a plurality of virtual focal planes and generates a three-dimensional (3D) model of the object by using the plurality of generated in-focus images. Further, the image generation system generates a given sectional image of the 3D model by using the plurality of in-focus images included in the 3D model.

1-1. Configuration of Image Generation System 1-1-1. Overall Configuration of Image Generation System FIG. 1 is a functional block diagram of an image generation system 10 according to the first embodiment. The image generation system 10 illustrated in FIG. 1 includes an imaging device 100, an image generation device 200, a storage unit 120, and a display unit 150. The image generation system 10 may further include a first memory 121 that stores information regarding predetermined focal planes, the shape of an object to be imaged, and the like; a second memory 122 that stores information regarding pixel(s) that have been subjected to refocusing processing; a focal plane input unit 130 that accepts input of specifying information for specifying a focal plane; and a computer graphics (CG) operation input unit 140 that accepts input of an operation instruction for an object displayed on the display unit 150. The display unit 150 is implemented by a display and displays an image or the like generated by an image operation unit 260 and a sectional image generation unit 270. The focal plane input unit 130 and the CG operation input unit 140 may be implemented by various input devices, such as a keyboard, a mouse, or a touchpad of a computer device or the like or by an input device based on a screen, such as a touchscreen, of the display unit 150.

1-1-2. Configuration of Imaging Device

The configuration of the imaging device 100 will be described first. The imaging device 100 includes a plurality of illuminators 101, an image sensor 102, and an imaging control unit 103. The imaging device 100 captures images (photographic images) of an object. Note that the imaging device 100 does not include a focus lens.

The object to be imaged includes, for example, a plurality of translucent objects placed on the surface of the image sensor 102. Specifically, the object is placed on a plurality of pixels, which are sensor pixels included in the image sensor 102 (described later). The surface of the image sensor 102 on which the object is placed includes a surface above the pixels of the image sensor 102. A specific example of the object is an early embryo of vertebrate animals, that is, a spherical embryo. A plurality of elements may three-dimensionally overlap in the object. A specific example of the plurality of elements is spherical cells. Herein, an embryo is an example of a first object, and a cell is an example of a second object. The first embodiment will be described below by using an embryo. The shape of an object to be imaged as the first object is not limited to sphere, and the object may have any shape. For example, the object to be imaged may have an ellipsoidal shape, a columnar shape, or a polygonal shape. The shape of the plurality of elements each serving as the second object is not limited to sphere and may have any shape. For example, the plurality of elements may have an ellipsoidal shape, a columnar shape, or a polygonal shape. The object to be imaged as the first object may be, for example, treated to be transparent or translucent so that the plurality of elements each serving as the second object contained therein is also imaged when the object is imaged. The plurality of elements each serving as the second object may be, for example, treated to be transparent or translucent so that light from the illuminators 101 passes therethrough; however, the plurality of elements may have a property other than being transparent or translucent. The element serving as the second object need not be provided in plural and a single element may serve as the second object.

The plurality of illuminators 101 are arranged in a line or on a surface, for example. Each of the plurality of illuminators 101 is an illuminator that outputs parallel rays or diffused rays. The plurality of illuminators 101 include a first illuminator and a second illuminator. Each of the first and second illuminators radiates rays that do not cross each other. That is, a plurality of first rays representing first light radiated from the first illuminator do not cross each other. In addition, a plurality of second rays representing second light radiated from the second illuminator do not cross each other. Accordingly, when light is radiated from one of the first illuminator and the second illuminator, the light from the one of the first illuminator and the second illuminator reaches each pixel of the image sensor 102 from a single direction. That is, light does not reach each pixel from two or more directions.

Hereinafter, such illumination is referred to as non-crossing illumination. Non-crossing illumination can be implemented by, for example, parallel rays or diffused rays from a point light source. The plurality of illuminators 101 sequentially radiate light. The plurality of illuminators 101 are arranged at different positions and irradiate the object with light from directions different from one another.

The image sensor 102 includes a plurality of pixels serving as sensor pixels. Each pixel of the image sensor 102 is disposed on a light-receiving surface and obtains intensity of light radiated from the plurality of irradiators 101. The image sensor 102 captures an image on the basis of intensities of light obtained by the respective pixels.

An example of the image sensor 102 may be a complementary metal-oxide semiconductor (CMOS) image sensor or a charge coupled device (CCD) image sensor.

The imaging control unit 103 controls radiation of light performed by the plurality of illuminators 101 and imaging performed by the image sensor 102. Specifically, the imaging control unit 103 controls the order in which the plurality of illuminators 101 radiate light and intervals at which the plurality of illuminators 101 radiate light. The imaging control unit 103 is constituted by a computer system (not illustrated) including a CPU, a RAM, and a ROM, for example. Functions of some or all of the components of the imaging control unit 103 may be implemented as a result of the CPU executing a program stored on the ROM by using the RAM as its work memory. In addition, functions of some or all of the components of the imaging control unit 103 may be implemented by a dedicated hardware circuit.

Figure 2:
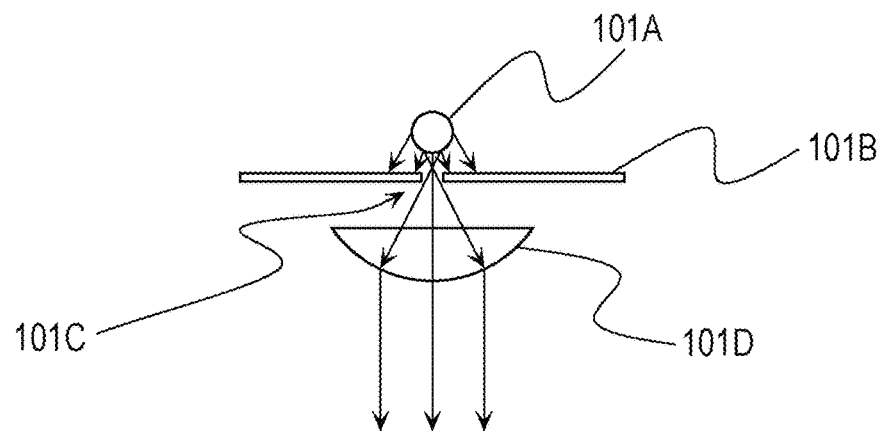
FIG. 2 is a diagram schematically illustrating an example of the structure of an illuminator according to the first embodiment.

Light radiated from the plurality of illuminators 101 that are disposed at different positions with respect to the light-receiving surface of the image sensor 102 are incident on the light-receiving surface at different incident angles. In the case where the plurality of illuminators 101 radiate parallel rays, the plurality of illuminators 101 radiate parallel rays having different incident angles with respect to the light-receiving surface of the image sensor 102. Parallel rays can be obtained by diffracting, using a collimating lens 101D, light emitted from a light-emitting diode (LED) light source 101A via a pinhole 101C of a light-shielding plate 101B as illustrated in FIG. 2, for example.

Figure 3:
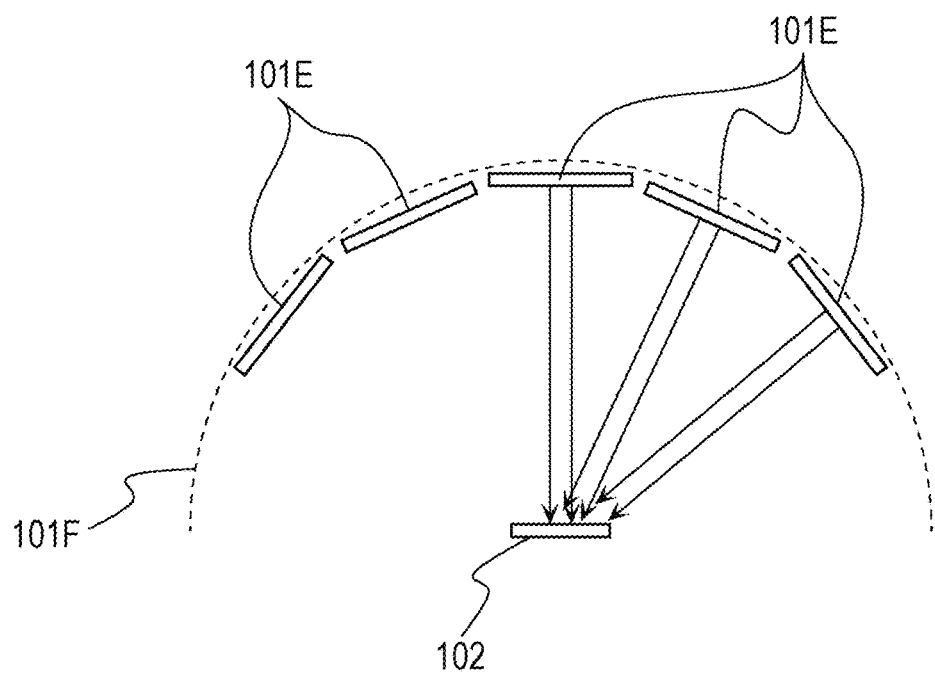
FIG. 3 is a diagram schematically illustrating an example of the structure of the illuminators according to the first embodiment.

FIG. 3 is a schematic diagram illustrating an example of the structure of the plurality of illuminators 101. In the example of the plurality of illuminators 101 illustrated in FIG. 3, a plurality of light sources 101E each of which radiates parallel rays are fixed at different angles with respect to the light-receiving surface of the image sensor 102. In the example illustrated in FIG. 3, the plurality of light sources 101E are disposed on the inner surface of a hemisphere 101F that covers the image sensor 102. Incident angles of light that reaches the light-receiving surface of the image sensor 102 from the plurality of light sources 101E are different from one another.

Figure 4:
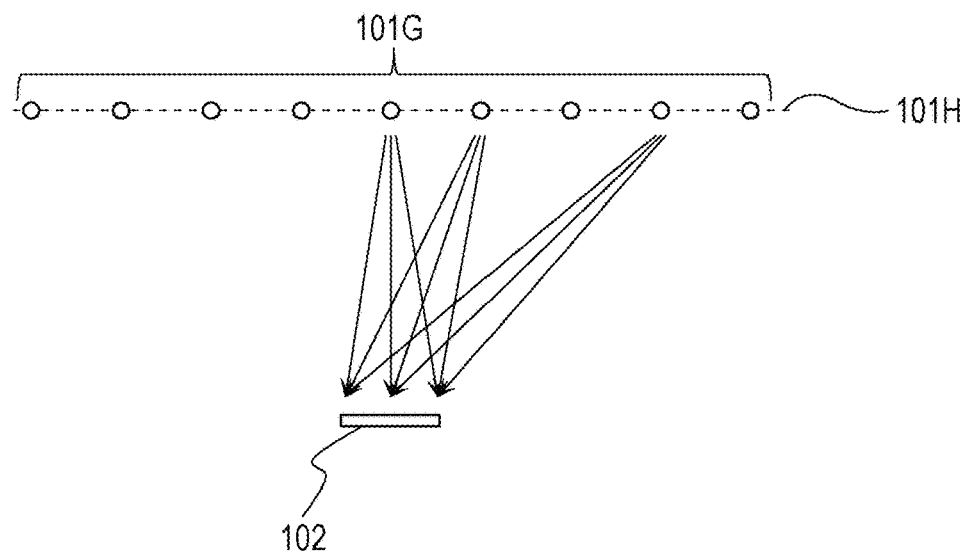
FIG. 4 is a diagram schematically illustrating an example of the structure of the illuminators according to the first embodiment.

FIG. 4 is a schematic diagram illustrating another example of the structure of the plurality of illuminators 101. In the example of the plurality of illuminators 101 illustrated in FIG. 4, a plurality of pseudo point light sources 101G are disposed at different positions on a flat surface 101H that is parallel to the light-receiving surface of the image sensor 102 so as to face the image sensor 102. Rays emitted from the plurality of pseudo point light sources 101G are incident on each pixel on the light-receiving surface of the image sensor 102 from different directions. Each of the plurality of pseudo point light sources 101G is implemented by placing the light-shielding plate 101B having the pinhole 101C near the LED light source 101A, for example. The diameter of the pinhole 101C is limited by a pixel pitch of the image sensor 102, a distance between the image sensor 102 and the pinhole 101C, and a distance of a point at which an in-focus image is generated from the image sensor 102.

Figure 5:
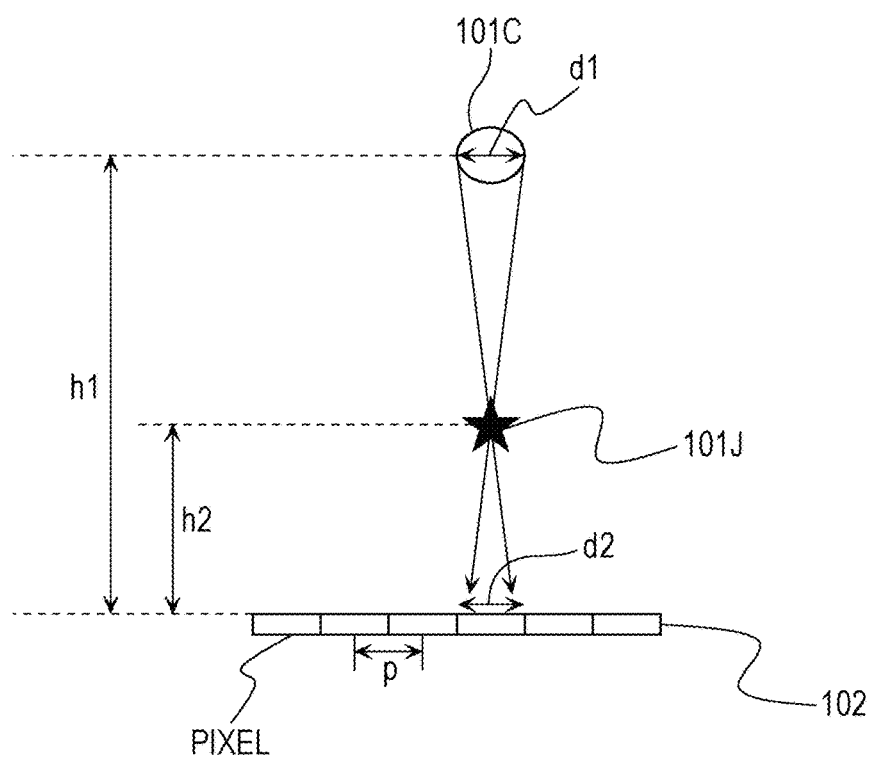
FIG. 5 is a schematic diagram for describing a condition of the diameter to be met by a pinhole of the illuminator according to the first embodiment.

FIG. 5 is a schematic diagram for describing a condition of the diameter to be met by the pinhole 101C. In FIG. 5, d1 denotes the diameter of the pinhole 101C, h1 denotes a distance from the light-receiving surface of the image sensor 102 to the pinhole 101C, and h2 denotes a distance from the light-receiving surface of the image sensor 102 to a focal point 101J (i.e., a point located on a focal plane of a given pixel of an in-focus image). In addition, d2 denotes the diameter of an extent of light that has passed through the focal point 101J from the pinhole 101 and has reached the light-receiving surface of the image sensor 102, and p denotes a pixel pitch of the image sensor 102.

At that time, light that exits from the pinhole 101C ideally passes through the focal point 101J and reaches a single point on the light-receiving surface of the image sensor 102. That is, it is desirable that light that exits from the pinhole 101C pass through the focal point 101J and reach a single pixel of the image sensor 102. Accordingly, it is desirable that d2 be smaller than the pixel pitch p of the image sensor 102. That is, d2<p is a condition for realizing non-crossing illumination as denoted by Equation 1.

$$d2 = \frac{d1 \cdot h2}{h1 - h2} < p \qquad \text{Equation 1}$$

A condition to be met by d1 can be expressed as Equation 2 by modifying Equation 1.

$$d1 < \frac{p(h1 - h2)}{h2} \qquad \text{Equation 2}$$

For example, when the pixel pitch p is equal to 0.001 mm, the distance h1 from the light-receiving surface of the image sensor 102 to the pinhole 101C is equal to 2 mm, and the distance h2 from the light-receiving surface of the image sensor 102 to the focal point 101J is equal to 0.1 mm, the diameter d1 of the pinhole 101C may be smaller than 0.19 mm.

1-1-3. Configuration of Image Generation Device

The configuration of the image generation device 200 will be described next. The image generation device 200 is implemented by a control circuit. As illustrated in FIG. 1, the image generation device 200 includes a focal plane determination unit 210, a refocusing processing unit 220, an in-focus image generation unit 230, a target object extraction unit 240, a 3D image generation unit 250, the image operation unit 260, and the sectional image generation unit 270.

The focal plane determination unit 210 is implemented by, for example, a control circuit or a processor. The focal plane determination unit 210 determines a virtual focal plane located between the image sensor 102 and the plurality of illuminators 101. Specifically, the focal plane determination unit 210 determines a focal plane on the basis of information regarding predetermined focal planes stored in the first memory 121, for example. The focal plane determination unit 210 may also determine the focal plane in accordance with information input from outside via the focal plane input unit 130. In the first embodiment, the focal plane determination unit 210 determines a plurality of focal planes that are substantially parallel to the light-receiving surface of the image sensor 102. In other words, the focal planes are flat planes in the first embodiment.

The storage unit 120 is implemented by, for example, a semiconductor memory or a hard disk drive. The storage unit 120 stores each image captured by the image sensor 102 together with position information of the illuminator 101 used for the imaging.

FIG. 6 illustrates an example of information stored in the storage unit 120. The storage unit 120 stores each image file of an image captured by the imaging device 100 in association with corresponding position information of the illuminator 101 used when the image file was created. In the example illustrated in FIG. 6, position information of the illuminator 101 represents a relative position of the illuminator 101 with respect to the image sensor 102. Hereinafter, position information of the illuminator 101 is also referred to as illumination position information. The illumination position information is stored together with the file ID of each image file and is associated with image data using the file ID. Note that the illumination position information may be stored as part of the image file (e.g., header information).

Referring to FIG. 1, the refocusing processing unit 220 is implemented by, for example, a control circuit or a processor. The refocusing processing unit 220 calculates intensity of light at each pixel of an in-focus image at a virtual focal plane by using the plurality of images, position information of the plurality of illuminators 101, and information regarding the virtual focal plane. In the first embodiment, the refocusing processing unit 220 calculates intensities of light at respective pixels of in-focus images at a plurality of focal planes. Details about this refocusing process will be described later.

The in-focus image generation unit 230 is implemented by, for example, a control circuit or a processor. The in-focus image generation unit 230 generates an in-focus image at each focal plane from pixel values of respective pixels calculated by the refocusing processing unit 220. A pixel value shows brightness of a region in an image.

The target object extraction unit 240 is implemented by, for example, a control circuit or a processor. The target object extraction unit 240 identifies an outline of an object-showing region, which is a region of the object, in an in-focus image at each focal plane and removes background that is located outside the outline from the in-focus image. That is, the target object extraction unit 240 generates a background-removed in-focus image.

The 3D image generation unit 250 is implemented by, for example, a control circuit or a processor. The 3D image generation unit 250 extracts an outline reference in-focus image which is an image including the outline of the object-showing region having the highest contrast from among a plurality of background-removed in-focus images. The 3D image generation unit 250 identifies a specific 3D outline of the object in accordance with the shape of two-dimensional (2D) outline in the outline reference in-focus image and the shape of the object stored in the first memory 121. The 3D image generation unit 250 further associates the plurality of background-removed in-focus images with the 3D outline of the object and removes a region outside the 3D outline from the plurality of background-removed in-focus images. In this way, sectional images of the object each corresponding to one of the plurality of background-removed in-focus images are generated. These sectional images are sectional images at focal planes set in advance and are referred to as reference sectional images. The 3D image generation unit 250 generates a 3D model of the object by using the plurality of reference sectional images. This 3D model can include information regarding the 3D outline of the object and the plurality of reference sectional images.

The image operation unit 260 is implemented by, for example, a control circuit or a processor. The image operation unit 260 displays the 3D model of the object generated by the 3D image generation unit 250 on the display unit 150. At that time, the image operation unit 260 displays the 3D outline of the object or the like on the display unit 150. Further, in response to selection of a position of the section of the object, the image operation unit 260 displays a brief image of the selected section on the display unit 150 together with the 3D outline of the object. At that time, the 3D image generation unit 250 generates a preview sectional image, which is the brief sectional image of the object, by using information included in the plurality of reference sectional images. Accordingly, for example, when the selected section is a section that crosses the focal planes (hereinafter, referred to as reference sectional image planes) corresponding to the plurality of reference sectional images, regions between the plurality of reference sectional image planes are not clearly shown in the preview sectional image. The image operation unit 260 accepts, via the CG operation input unit 140, an instruction to select a position of the preview sectional image to be displayed and displays the preview sectional image of the object on the basis of this instruction.

The sectional image generation unit 270 is implemented by, for example, a control circuit or a processor. The sectional image generation unit 270 generates a detailed image of a to-be-displayed section of the object by using the position of the to-be-displayed section of the object and information included in the plurality of reference sectional images and displays the detailed sectional image on the display unit 150. Specifically, the sectional image generation unit 270 uses, as a pixel value of a pixel in a region of the to-be-displayed section of the object that overlaps or crosses a reference sectional image plane, a pixel value of the corresponding pixel of the reference sectional image. The sectional image generation unit 270 calculates a pixel value of a pixel in a region of the to-be-displayed section of the object that neither overlaps nor crosses any reference sectional image plane, by using pixel values of pixels of reference sectional images at respective reference sectional image planes that are located near this pixel. That is, the sectional image generation unit 270 calculates a pixel value of a pixel (hereinafter, also referred to an interpolation pixel) located between pixels for which respective pixels of the corresponding reference sectional images are used in the to-be-displayed section of the object. The sectional image generation unit 270 then generates a detailed image of the section of the object by using the pixel values of pixels included in the reference sectional images and the pixel values of interpolation pixels. The sectional image generation unit 270 displays the generated image on the display unit 150. The sectional image generation unit 270 can be informed of the position of the to-be-displayed section of the object via the CG operation input unit 140. Specifically, the to-be-displayed section of the object may be selected by using the CG operation input unit 140 from among preview sectional images of the object displayed on the display unit 150. In this way, the to-be-displayed section of the object may be determined.

Figure 7:
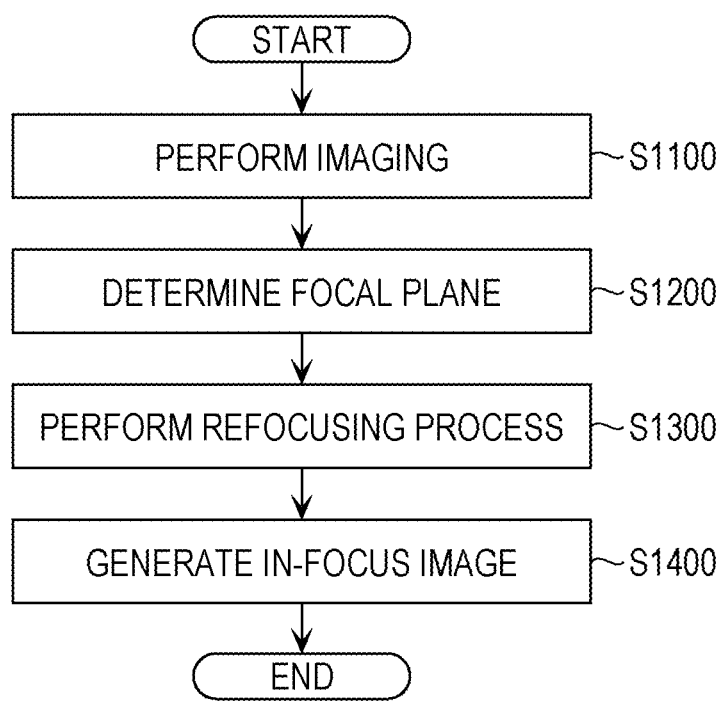
FIG. 7 is a flowchart illustrating an example of an operation of the image generation system according to the first embodiment.
Figure 8:
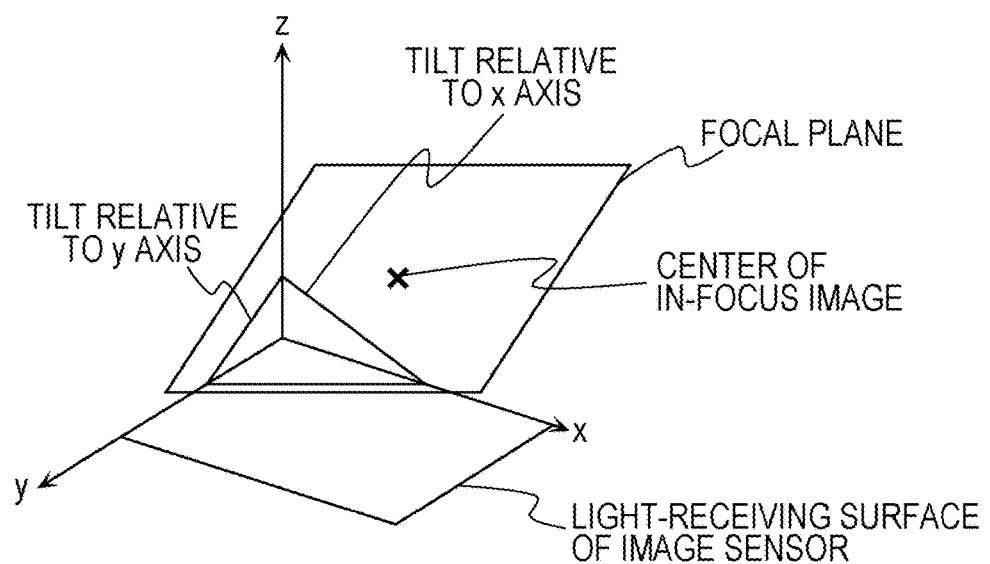
FIG. 8 is a schematic diagram illustrating an example of a relationship between coordinates and a focal plane.

1-2. Operation of Image Generation System 1-2-1. Overview of Operation of Refocusing Process of Image Generation System An overview of an operation of the refocusing process performed by the image generation system 10 thus configured, that is, an overview of an operation of generating an in-focus image, will be described next. FIG. 7 is a flowchart illustrating an example of an operation of generating an in-focus image performed by the image generation system 10 according to the first embodiment. FIG. 8 is a schematic diagram illustrating an example of a relationship between coordinates and a focal plane.

In step S1100, the imaging control unit 103 of the imaging device 100 irradiates the object with light by sequentially using the plurality of illuminators 101 and captures a plurality of images of the object. Specifically, the imaging control unit 103 records intensity of light that has reached each pixel on the light-receiving surface of the image sensor 102 when the object is irradiated with light by each of the plurality of illuminators 101. In this way, the imaging control unit 103 captures images of the object. Each captured image is stored in the storage unit 120 together with the position information of the illuminator 101 that has irradiated the object with light at the time of imaging. In this embodiment, the positions of the plurality of illuminators 101 are fixed with respect to the image sensor 102, and thus the position information of each of the plurality of illuminators 101 is predetermined. Details of the imaging process will be described later.

In step S1200, the focal plane determination unit 210 of the image generation device 200 determines the focal plane. Specifically, the focal plane determination unit 210 determines the position and tilt (angle) of the focal plane with respect to the image sensor 102. For example, the focal plane determination unit 210 may determine the focal plane on the basis of information regarding predetermined focal planes stored in the first memory 121. Alternatively, the focal plane determination unit 210 may determine the focal plane on the basis of specifying information that is accepted from the user via the focal plane input unit 130 and that specifies the focal plane. The focal plane corresponds to a virtual plane for which an in-focus image is generated. That is, a plurality of pixels included in an in-focus image of an object at a focal plane and a plurality of points on the focal plane have a one-to-one correspondence. For example, the focal plane determination unit 210 determines the focal plane by using the angle and position of the focal plane. The angle and position of the focal plane are defined by using an xyz space illustrated in FIG. 8, for example.

Referring to FIG. 8, the x-y plane matches the light-receiving surface of the image sensor 102. The z axis is orthogonal to the light-receiving surface of the image sensor 102. In this case, the angle of the focal plane is defined using angles with respect to the x axis and y axis in the xyz space having the original at the center of the light-receiving surface of the image sensor 102. The position of the focal plane is defined by coordinates of the center of the focal plane. The sectional image generation unit 270 is implemented by, for example, a control circuit or a processor. The sectional image generation unit 270 generates a detailed image of a to-be-displayed section of the object by using the position of the to-be-displayed section of the object and information included in a plurality of reference sectional images and displays the detailed image on the display unit 150.

In step S1300, the refocusing processing unit 220 performs a refocusing process on the basis of the plurality of captured images, the position information of the plurality of illuminators 101, and information regarding the focal plane and determines a pixel value of each pixel (i.e., each point) on the focal plane. Details of the refocusing process will be described later.

In step S1400, the in-focus image generation unit 230 generates an in-focus image at the focal plane, which is image data that can be output to a display, on the basis of the result of the refocusing process performed in step S1300.

1-2-2. Imaging Process

Figure 9:
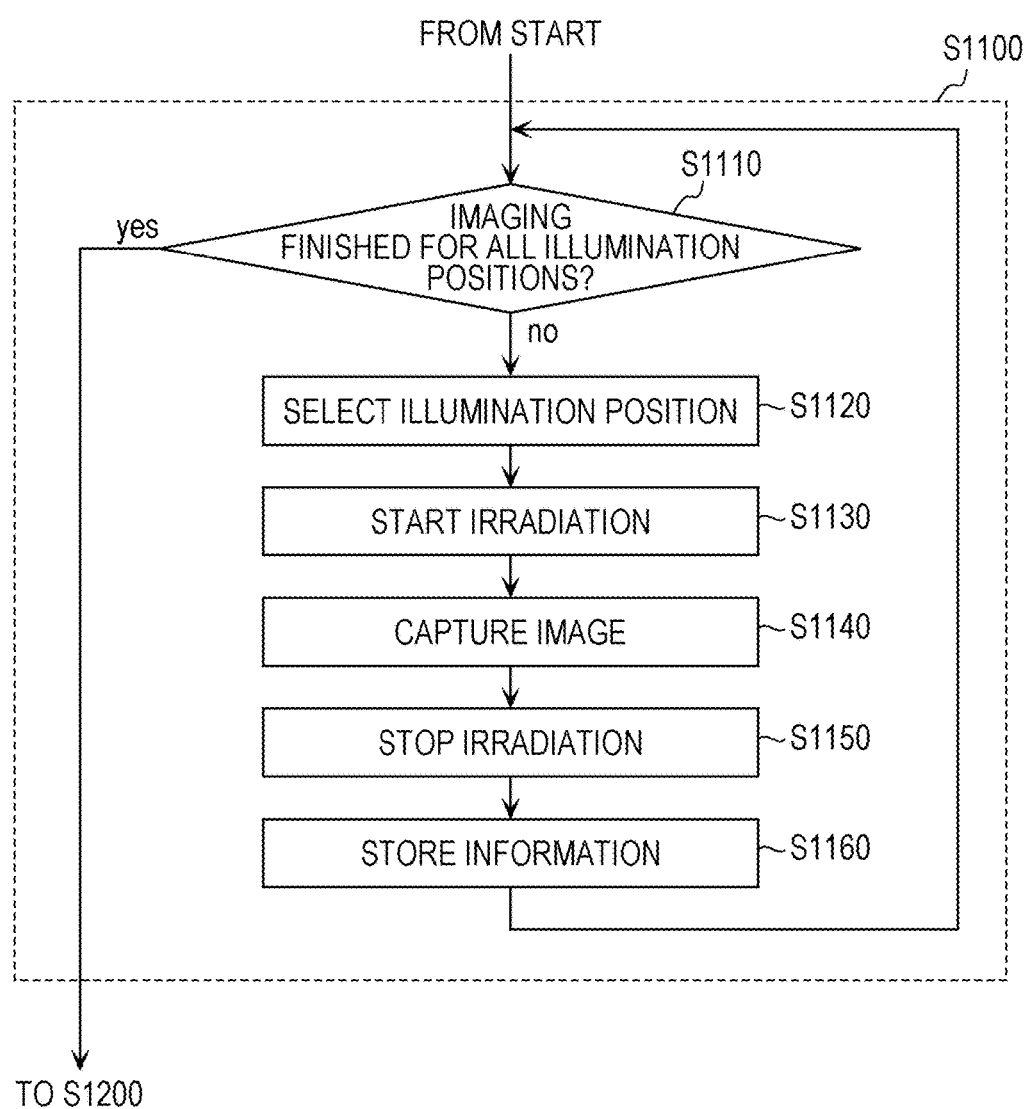
FIG. 9 is a flowchart illustrating an example of an operation of an imaging device according to the first embodiment.

Now, details of the operation performed by the imaging device 100 in step S1100, specifically, the operation of the imaging control unit 103, is described. FIG. 9 is a flowchart illustrating an example of the operation of the imaging device 100.

In step S1110, the imaging control unit 103 determines whether imaging of an object irradiated with light from illumination positions has been finished with reference to a list (hereinafter, referred to as an illumination position list) of a plurality of predetermined illumination positions or a plurality of illumination positions specified through an input from outside (not illustrated). The plurality of illuminators 101 and the plurality of illumination positions included in the illumination position list have a one-to-one correspondence.

If imaging is finished for illumination from all the illumination positions included in the illumination position list (yes in step S1110), the process proceeds to step S1200 to determine the focal plane. On the other hand, if imaging is not finished for illumination from any of the illumination positions included in the illumination position list (no in step S1110), the process proceeds to step S1120.

In step S1120, the imaging control unit 103 selects an illumination position from which light has not been radiated yet from among the plurality of illumination positions included in the illumination position list and outputs control signals to the plurality of illuminators 101. If light has not been radiated from a plurality of illumination positions, the imaging control unit 103 selects one illumination position from among the plurality of illumination positions. Each illumination position is represented, for example, by a number assigned to the illumination position in the illumination position list. Alternatively, each illumination position is represented, for example, by coordinate values in the xyz space illustrated in FIG. 8. The illumination position is selected in ascending order of the list, for example.

In step S1130, the plurality of illuminators 101 start irradiating the object with light in accordance with the control signals output from the imaging control unit 103 in step S1120. That is, the illuminator 101 located at the illumination position selected in step S1120 starts irradiating the object with light.

In step S1140, while the object is irradiated with light by the illuminator 101, the image sensor 102 captures an image formed by light that has been emitted from the illuminator 101 and has passed through the object.

In step S1150, the imaging control unit 103 then outputs control signals to the plurality of illuminators 101 to stop irradiation of the object with light. Irradiation of the object with light need not be stopped in accordance with the control signals output from the imaging control unit 103. For example, the plurality of illuminators 101 may count a period from the start of irradiation and may spontaneously stop irradiation upon the counted period exceeding a predetermined period. Alternatively, the image sensor 102 may output control signals for stopping irradiation to the plurality of illuminators 101 after the image sensor 102 finishes capturing an image in step S1140.

In step S1160, the imaging control unit 103 then outputs data of the image captured in step S1140 and the position information of the illuminator 101 used in step S1130 to the storage unit 120. The storage unit 120 then stores the image data and the illumination position information in association with each other. The process returns to step S1110 after step S1160.

As a result of iteration of the process from step S1110 to step S1160, the object is sequentially irradiated with light by the illuminators 101 located at the respective illumination positions included in the illumination position list and an image is captured every time the object is irradiated with light.

1-2-3. Detailed Operation of Refocusing Process of Image Generation System

Figure 10:
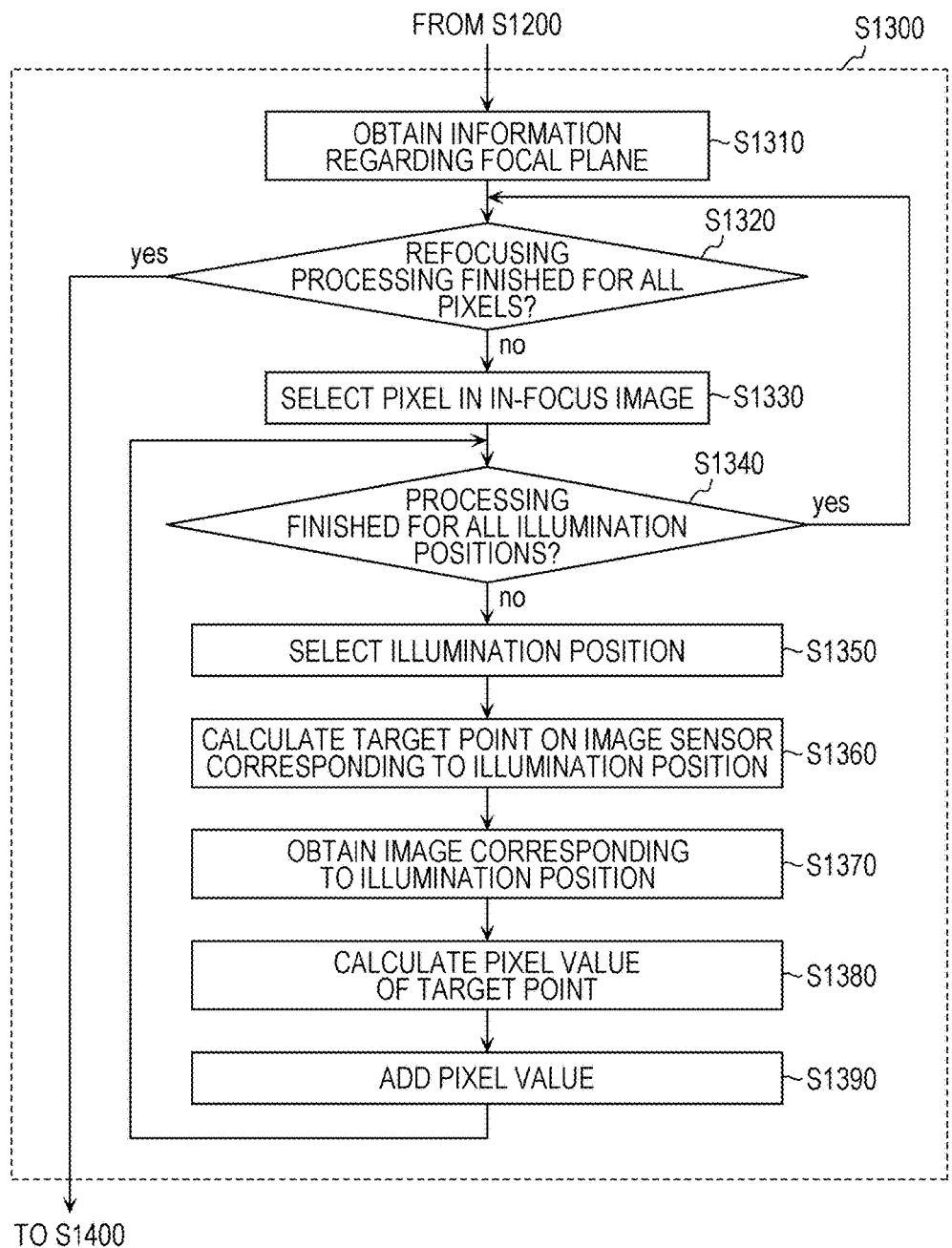
FIG. 10 is a flowchart illustrating an example of an operation of a refocusing processing unit according to the first embodiment.

A detailed operation performed by the refocusing processing unit 220 in step S1300 will be further described. FIG. 10 is a flowchart illustrating an example of an operation of the refocusing processing unit 220 according to the first embodiment. FIGS. 11 to 15 are schematic diagrams for describing a specific example of a calculation method performed in the refocusing process.

Each step of FIG. 10 will be described below with reference to FIGS. 11 to 15.

In step S1310, the refocusing processing unit 220 obtains information regarding the focal plane determined in step S1200 from the focal plane determination unit 210.

The information regarding the focal plane includes, for example, coordinate values of the center of the focal plane and a value representing the tilt of the focal plane. The tilt of the focal plane is represented by, for example, an angle between a line of intersection of the focal plane and the x-z plane and the x axis. In addition, the tilt of the focal plane is represented by, for example, an angle between a line of intersection of the focal plane and the y-z plane and the y axis. The coordinate values of the center of the focal plane are coordinate values of a point on the focal plane that corresponds to the pixel located at the center of the in-focus image.

Figure 11:
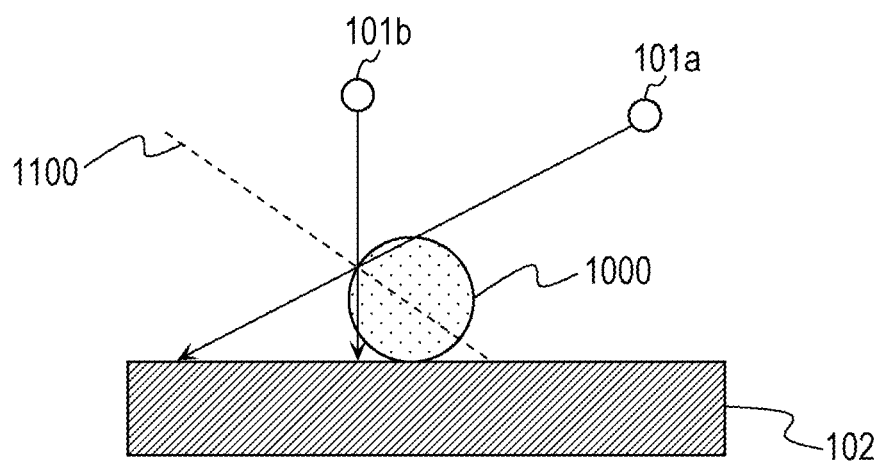
FIG. 11 is a schematic diagram for describing a specific example of a refocusing process according to the first embodiment.

FIG. 11 illustrates an example of a sectional view of the imaging device 100 and an object 1000 at the x-z plane. The object 1000 is located between illuminators 101a and 101b and the image sensor 102 and is located on the image sensor 102. The refocusing processing unit 220 obtains information regarding a focal plane 1100.

In step S1320, the refocusing processing unit 220 determines whether refocusing processing has been finished for all pixels included in an in-focus image. Herein, the refocusing processing indicates processing from step S1320 to step S1390.

If the refocusing processing has been finished for all pixels included in the in-focus image (yes in step S1320), the refocusing processing unit 220 ends the refocusing process (and the process proceeds to step S1400).

If the refocusing processing has not been finished for any of the pixels included in the in-focus image (no in step S1320), the refocusing processing unit 220 continues the refocusing process (and the process proceeds to step S1330).

Figure 12:
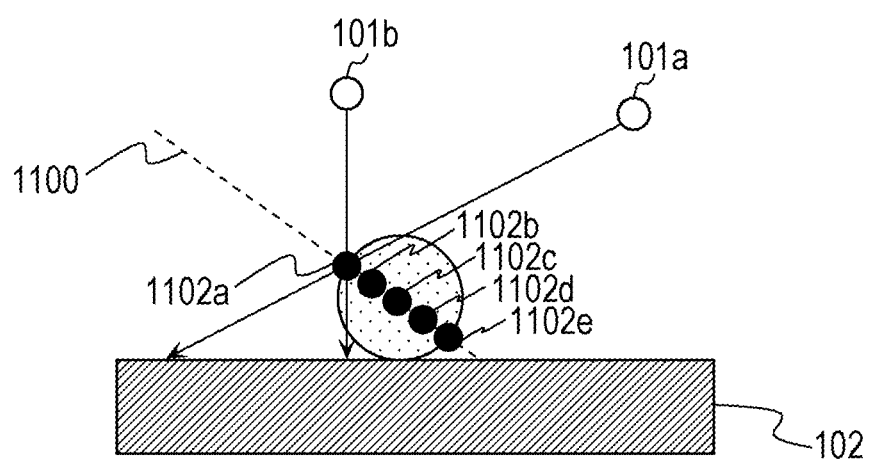
FIG. 12 is a schematic diagram for describing the specific example of the refocusing process according to the first embodiment.

The in-focus image includes a plurality of pixels. The plurality of pixels included in the in-focus image and a plurality of points on the focal plane have a one-to-one correspondence. FIG. 12 illustrates a plurality of points 1102a to 1102e on the focal plane 1100 that correspond to a plurality of pixels included in the in-focus image. The plurality of points 1102a to 1102e on the focal plane 1100 illustrated in FIG. 12 are points on the object 1000; however, points that are not on the object 1000 may correspond to respective pixels of the in-focus image.

In step S1330, the refocusing processing unit 220 selects a pixel from among the plurality of pixels included in the in-focus image. The pixel selected in this step is a pixel for which the refocusing processing has not been performed yet from among the plurality of pixels included in the in-focus image. Note that the initial pixel value of the in-focus image is equal to zero.

Figure 13:
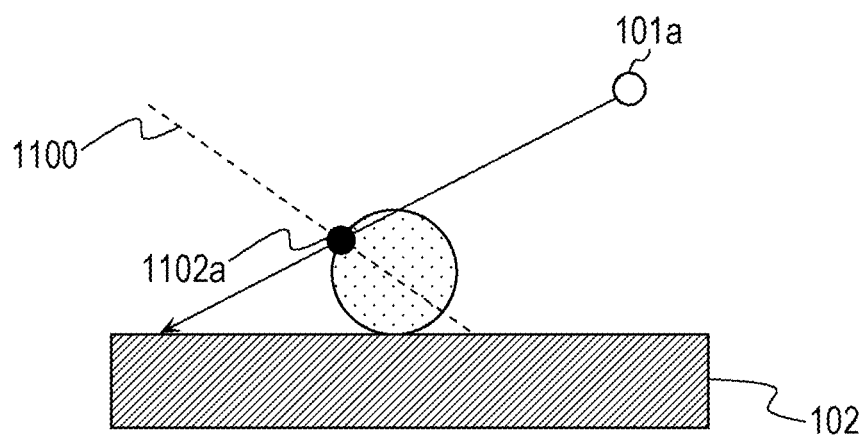
FIG. 13 is a schematic diagram for describing the specific example of the refocusing process according to the first embodiment.

For example, information regarding pixel(s) of the in-focus image for which the refocusing processing has already been performed is stored in the second memory 122 illustrated in FIG. 1. After processing of step S1390 (described later) is performed, the refocusing processing unit 220 stores information regarding the pixel subjected to the refocusing processing in the second memory 122. The refocusing processing unit 220 selects a pixel for which the refocusing processing has not been performed yet with reference to the information regarding the pixel(s) stored in the second memory 122. A case where a pixel corresponding to the point 1102a is selected as illustrated in FIG. 13 will be described below. The pixel corresponding to the point 1102a is also referred to as a selected pixel.

In step S1340, the refocusing processing unit 220 determines whether addition processing has been finished for all the illumination positions.

If addition processing has been finished for all the illumination positions (yes in step S1340), the process of the refocusing processing unit 220 returns to step S1320.

On the other hand, if addition processing has not been finished yet for any of the illumination positions (no in step S1340), the refocusing processing unit 220 continues the addition processing (and the process proceeds to step S1350). Here, addition processing indicates processing from step S1340 to step S1390.

In step S1350, the refocusing processing unit 220 selects an illumination position for which addition processing has not been finished yet from among all the illumination positions used for imaging.

In step S1360, the refocusing processing unit 220 calculates the position of a point at which a line that passes through the selected illumination position and the position corresponding to the selected pixel on the focal plane crosses the light-receiving surface of the image sensor 102.

Figure 14:
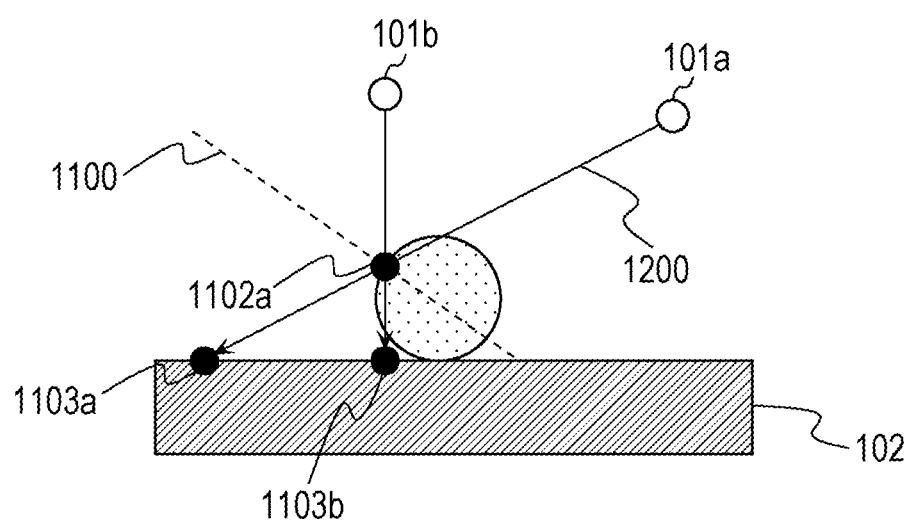
FIG. 14 is a schematic diagram for describing the specific example of the refocusing process according to the first embodiment.

FIG. 14 illustrates an intersection point 1103a of a line 1200 that passes through the position of the illuminator 101a and the point 1102a corresponding to the selected pixel and the light-receiving surface of the image sensor 102. Hereinafter, the intersection point 1103a is also referred to as a target point that is a point subjected to addition processing.

The target point on the light-receiving surface of the image sensor 102 is represented by coordinate values on the x-y plane illustrated in FIG. 8, for example.

In step S1370, the refocusing processing unit 220 obtains an image corresponding to the selected illumination position from the storage unit 120. That is, the refocusing processing unit 220 obtains an image captured by using the illuminator 101 located at the selected illumination position from the storage unit 120. Specifically, the refocusing processing unit 220 obtains an image stored in the storage unit 120 in accordance with a correspondence between the illumination position information and the image illustrated in FIG. 6. For example, the refocusing processing unit 220 obtains an image corresponding to the position of the illuminator 101a illustrated in FIG. 13.

In step S1380, the refocusing processing unit 220 determines a position in the obtained image that corresponds to the position of the target point on the image sensor 102 determined in step S1360. Specifically, the refocusing processing unit 220 determines a position in the obtained image that corresponds to the position of the target point with reference to a pixel array of the obtained image.

If the position in the photographic image that corresponds to the target point is between the plurality of pixels, the refocusing processing unit 220 calculates a pixel value of the target point in the photographic image by performing interpolation processing by using pixel values of the plurality of pixels adjacent to the position of the target point. Specifically, the refocusing processing unit 220 determines a distances between the target point and each of a plurality of pixels (for example, four pixels) that are adjacent to the target point and multiplies pixel values of the respective pixels by the respective proportions of the distances between the target point and the pixels and adds the products together. In this way, the refocusing processing unit 220 determines the pixel value of the target point in the photographic image.

Figure 15:
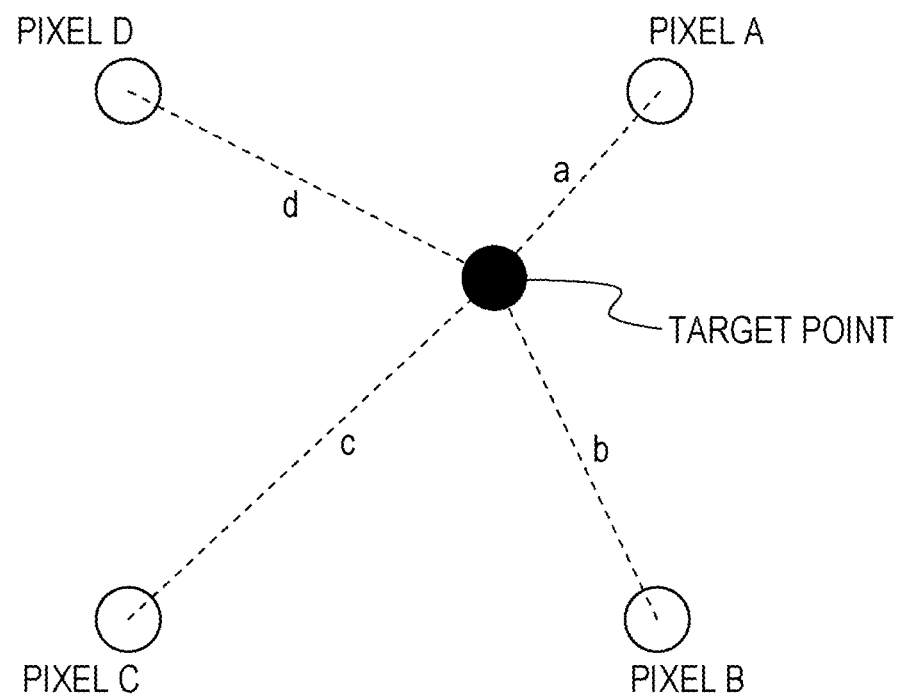
FIG. 15 is a schematic diagram for describing the specific example of the refocusing process according to the first embodiment.

FIG. 15 is a schematic diagram for describing how the pixel value of the target point is calculated in step S1380.

Referring to FIG. 15, distances between the target point and four pixels A to D that are adjacent to the target point are respectively denoted as a, b, c, and d. In this case, the pixel value $L_t$ of the target point is determined by using Equation 3 below.

$$L_t = \left(\frac{L_a}{a} + \frac{L_b}{b} + \frac{L_c}{c} + \frac{L_d}{d}\right) \times (a + b + c + d) \qquad \text{Equation 3}$$

In Equation 3, $L_a$, $L_b$, $L_c$, and $L_d$ represent pixel values of the pixels A, B, C, and D, respectively.

In step S1390, the refocusing processing unit 220 adds the pixel value of the target point calculated in step 1380 to the pixel value of the selected pixel in the in-focus image.

As a result of iteration of the processing from step S1340 to step S1390, the result obtained by adding the pixel value of the target point in the respective images captured for all the illumination positions to the pixel value of the selected pixel is calculated as the pixel value of the selected pixel.

As a result of such addition processing, a plurality of images formed by light that has passed through each point on the focal plane from a plurality of directions are superimposed at a pixel in the in-focus image.

Referring to FIG. 14, light radiated from the illuminator 101a passes through the point 1102a on the focal plane 1100 that corresponds to the selected pixel and reaches the target point (intersection point 1103a) on the light-receiving surface of the image sensor 102. Accordingly, an image at the point 1102a on the focal plane 1100 is contained at a position of the target point (i.e., the intersection point 1103a) of the image captured using the illuminator 101a.

In addition, in FIG. 14, light radiated from the illuminator 101b passes through the point 1102a on the focal plane 1100 that corresponds to the selected pixel and reaches the target point (intersection point 1103b) on the light-receiving surface of the image sensor 102. Accordingly, an image at the point 1102a on the focal plane 1100 is contained at a position of the target point (i.e., the intersection point 1103b) in the image captured using the illuminator 101b.

By adding the images (pixel values) at such target points (i.e., the intersection points 1103a and 1103b) together, a plurality of images formed by using light from a plurality of directions are superimposed at the selected pixel in the in-focus image.

According to the refocusing process described above, the pixel value of a target point, which is an intersection point of a line connecting the position of a pixel on the focal plane and the position of the illuminator 101 and the light-receiving surface of the image sensor 102, can be used for the pixel value of the pixel. Accordingly, pixel values of a pixel in a plurality of captured images are successfully reflected in a pixel value of the corresponding pixel of an in-focus image at a virtual focal plane, and consequently a high-quality in-focus image of the object is successfully generated.

A target point which is an intersection point of the light-receiving surface of the image sensor 102 and a line that passes through the position of the illuminator 101 and a point corresponding to the selected pixel is used in the refocusing process described above. That is, the target point having a pixel value to be added to the pixel value of the selected pixel is identified on the basis of a relationship among the position of the illuminator 101, the point corresponding to the selected pixel, and the target point on the light-receiving surface of the image sensor 102; however, a pixel having the pixel value to be added to the pixel value of the selected pixel may be identified on the basis of a relationship among the position of the illuminator 102, the selected pixel, and the pixel on the light-receiving surface of the image sensor 102 instead of the relationship between the points. For example, a pixel value detected by a pixel of the image sensor 102 that receives light that reaches the light-receiving surface of the image sensor 102 after being emitted from the illuminator 101 and passing through a region of the selected pixel may be added to the pixel value of the selected pixel. That is, a pixel value detected by a pixel of the image sensor 102 that satisfies a positional relationship in which the position of the illuminator 101, the selected pixel, and the pixel on the image sensor 102 are arranged in a line may be added to the pixel value of the selected pixel.

1-2-4. Detailed Operation of Image Generation System

Figure 16:
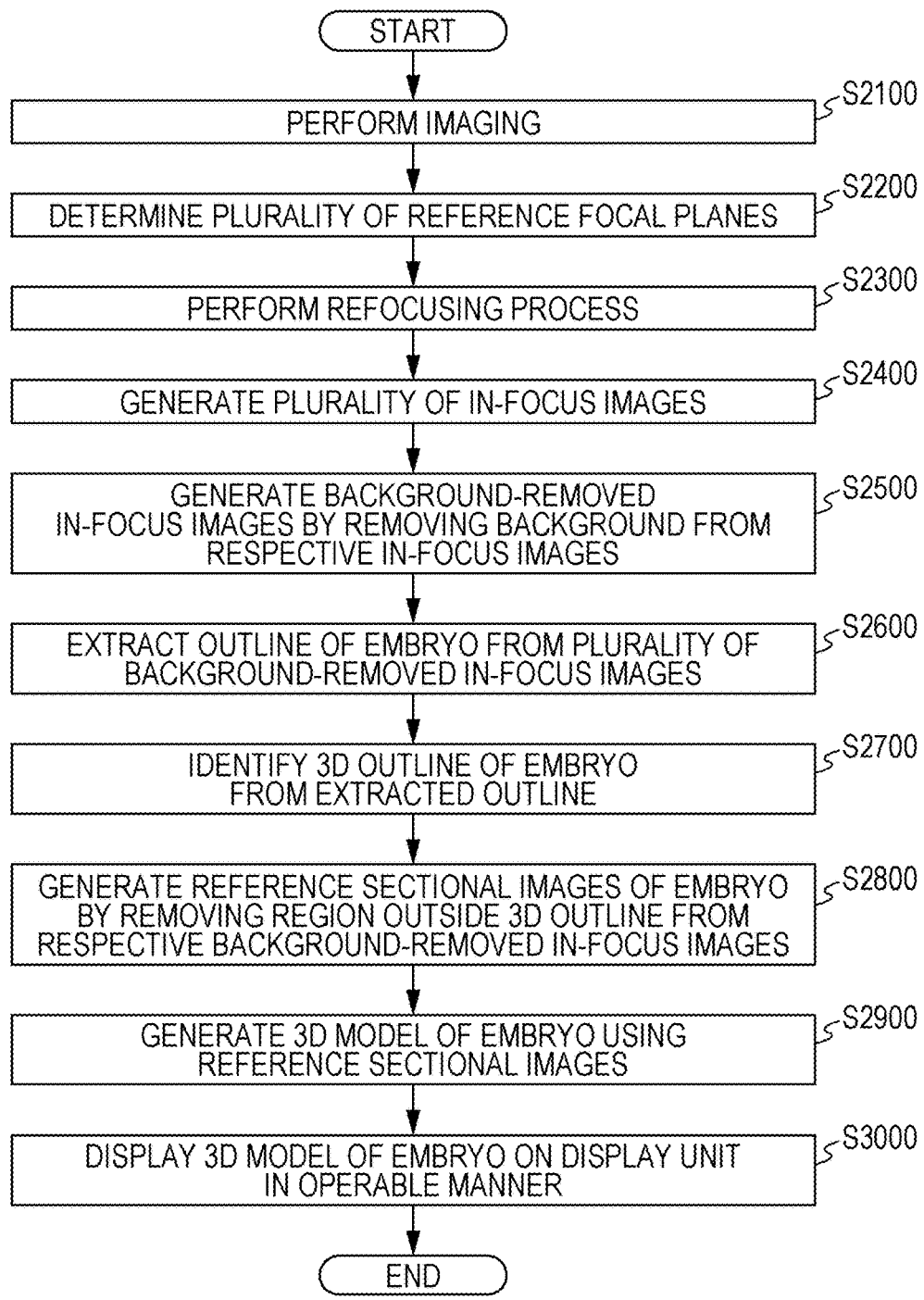
FIG. 16 is a flowchart illustrating an example of an operation of the refocusing processing unit according to the first embodiment.
Figure 17:
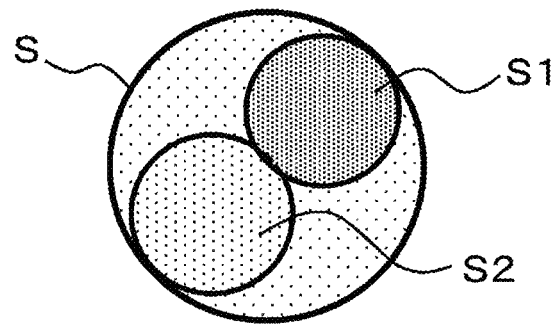
FIG. 17 is a perspective view of an embryo which is an example of an object to be imaged.

An operation of the image generation system 10 thus configured will be described in detail with reference to FIG. 16 next. FIG. 16 is a flowchart illustrating an example of an operation of the image generation system 10 according to the first embodiment. The following description will be given of the case where a translucent embryo S which is an early embryo of a vertebrate animal as illustrated in FIG. 17 is used as an object to be imaged. FIG. 17 is a perspective view of the embryo S, which is an example of the object. Referring to FIG. 17, the spherical embryo S includes two spherical cells S1 and S2 resulting from cleavage.

In step S2100, the imaging control unit 103 of the imaging device 100 irradiates the translucent embryo S placed on the light-receiving surface of the image sensor 102 with light by sequentially using the plurality of illuminators 101 and captures a plurality of images of the embryo S. In the first embodiment, the positions of the plurality of illuminators 101 are fixed with respect to the image sensor 102, and position information of the plurality of illuminators 101 is predetermined. The imaging control unit 103 records intensity of light that has reached individual pixels on the light-receiving surface of the image sensor 102 when the embryo S is irradiated with light by each of the plurality of illuminators 101 so as to capture an image of the embryo S. Each captured image is stored in the storage unit 120 together with the position information of the illuminator 101 used for irradiation of the embryo S with light at the time of imaging.

In step S2200, the focal plane determination unit 210 of the image generation device 200 determines a plurality of reference focal planes which are focal planes used as references. In the first embodiment, the plurality of reference focal planes that are substantially parallel to the light-receiving surface of the image sensor 102 and are spaced apart from one another are determined. Specifically, a plurality of reference focal planes that are substantially parallel to the light-receiving surface and are spaced apart from one another by an interval of approximately 1 μm are determined for the embryo S having a diameter of approximately 100 μm. The plurality of reference focal planes are arranged in a region that extends over a distance of approximately 110 μm from the light-receiving surface. With this configuration, the entire embryo S is included in a region where the plurality of reference focal planes are present. Many reference focal planes among the plurality of reference focal planes cross the embryo S. Note that the specific numerical values are example values and numerical values of the respective elements are not limited to these numerical values.

In step S2300, the refocusing processing unit 220 performs the refocusing process on the basis of the plurality of captured images, the position information of the plurality of illuminators 101, and the information regarding the reference focal planes and determines pixel values of respective pixels (i.e., points) on each of the reference focal planes.

Figure 18:
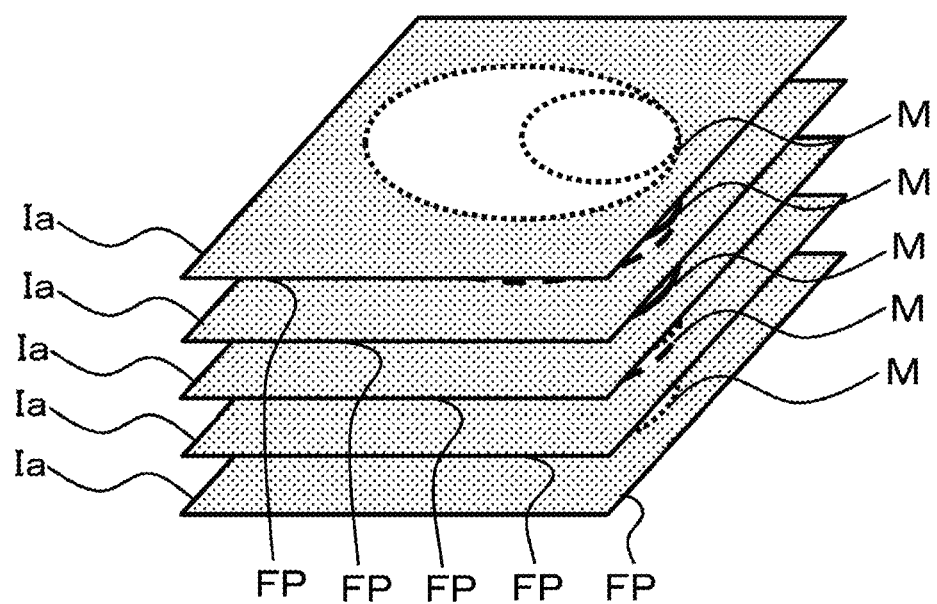
FIG. 18 is a schematic diagram of a stack of reference in-focus images at a plurality of reference focal planes that are stacked in a line in the arrangement order.
Figure 19:
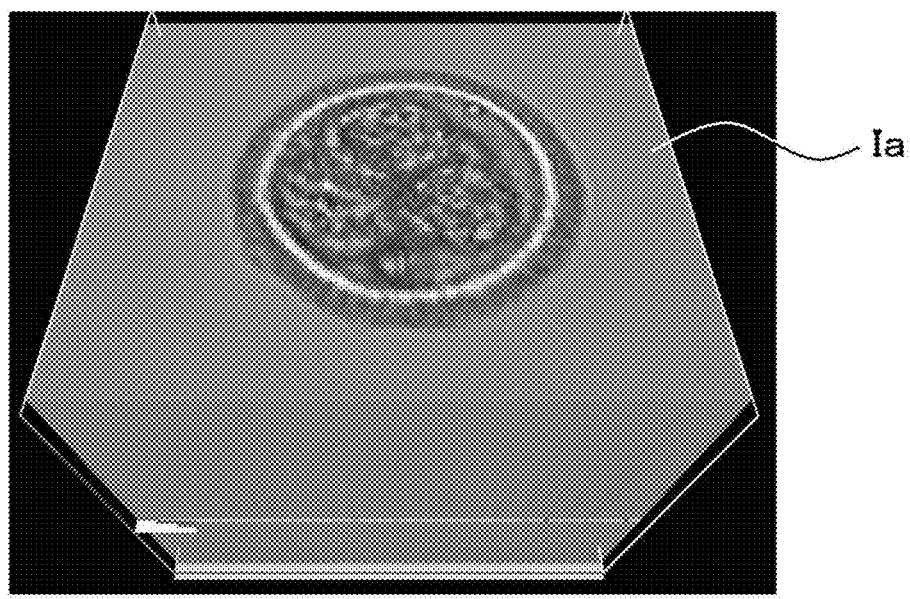
FIG. 19 is a diagram illustrating an example in which the plurality of reference in-focus images are displayed using a photograph.

In step S2400, the in-focus image generation unit 230 generates reference in-focus images, which are in-focus images at the plurality of reference focal planes and can be output to a display or the like, on the basis of the result of the refocusing process performed in step S2300. Note that since the reference focal plane is a plane at which an in-focus image is formed, it is also referred to as an in-focus image plane or a refocusing image plane. FIG. 18 illustrates reference in-focus images Ia at a plurality of reference focal planes FP of the embryo S. FIG. 18 is a schematic diagram illustrating a stack of the reference in-focus images Ia at the plurality of reference focal planes FP arranged in a line in the arrangement order. FIG. 18 illustrates some of the plurality of reference in-focus images Ia. FIG. 19 illustrates an example in which the reference in-focus images Ia arranged in a line are displayed as an image on the display screen 151 of the display unit 150. FIG. 19 is a diagram illustrating an example in which the reference in-focus images Ia are displayed using a photograph. FIG. 19 illustrates an example in which the embryo S includes four cells. The reference in-focus image Ia at each reference focal plane FP includes a region of pixels that receives light that has passed through the embryo S, that is, an object-showing region M including an image of the embryo S.

Figure 20:
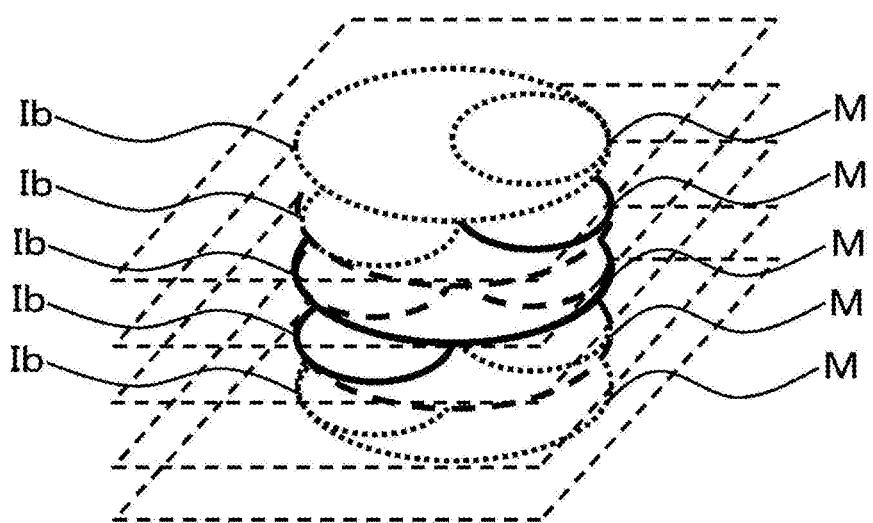
FIG. 20 is a diagram illustrating a stack of a plurality of background-removed in-focus images that are stacked in a line in the arrangement order of respective reference focal planes.
Figure 21:
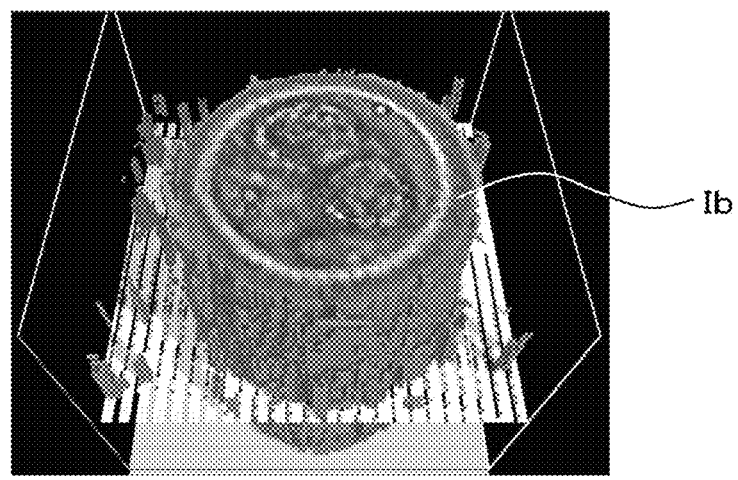
FIG. 21 is a diagram illustrating an example in which the plurality of background-removed in-focus images are displayed using a photograph.

In step S2500, the target object extraction unit 240 identifies an outline of the object-showing region M including the image of the embryo S in each reference in-focus image Ia at the corresponding reference focal plane FP as illustrated in FIG. 20 and generates a background-removed in-focus image Ib by removing background located outside the outline from the reference in-focus image Ia. The outline may be identified in the following manner, for example. The object extraction unit 240 detects circles from the image by using the Hough transform and determines a circle having the largest radius as the outline from among the detected circles. Alternatively, the target object extraction unit 240 may use, for example, the dimension of the embryo S (i.e., the object), for example, the diameter of 100 μm, as a reference and may determine a circle having a diameter that is the closest to the reference as the outline from among the detected circles. An example of how the outline of the embryo S is identified will be described. The embryo S has, for example, a spherical shape having a diameter of approximately 100 μm. The target object extraction unit 240 applies a Laplacian filter to the reference in-focus image Ia to extract edge points of the embryo S. The target object extraction unit 240 classifies a plurality of pixels of the reference in-focus image Ia by using the filtering result. For example, the target object extraction unit 240 sets a threshold on the basis of an intensity distribution of the input image (the reference in-focus image Ia in this case). An example of the threshold is a boundary point at which the ratio of the number of low-intensity pixels to the number of all pixels is 25% based on the intensity histogram. The target object extraction unit 240 extracts, as edge points, pixels having an intensity lower than or equal to the threshold. The target object extraction unit 240 applies the Hough transform on the extracted edge points to extract circles. For example, the target object extraction unit 240 extracts a circle corresponding to the embryo S by extracting circles having a diameter in a range from 80 μm to 120 μm. Since the center and the radius of the circle are determined through the Hough transform, a circle serving as an outline is successfully identified in the reference in-focus image Ia. FIG. 20 is a schematic diagram illustrating a stack of the plurality of background-removed in-focus images Ib arranged in a line in accordance with the arrangement order of the reference focal planes FP as in FIG. 18. FIG. 21 illustrates an example in which the background-removed in-focus images Ib that are stacked in a line are displayed on the display screen 151 of the display unit 150 as an image. FIG. 21 is a diagram illustrating an example in which the background-removed in-focus images Ib are displayed using a photograph. FIG. 21 illustrates the example in which the embryo S includes four cells.

Figure 22:
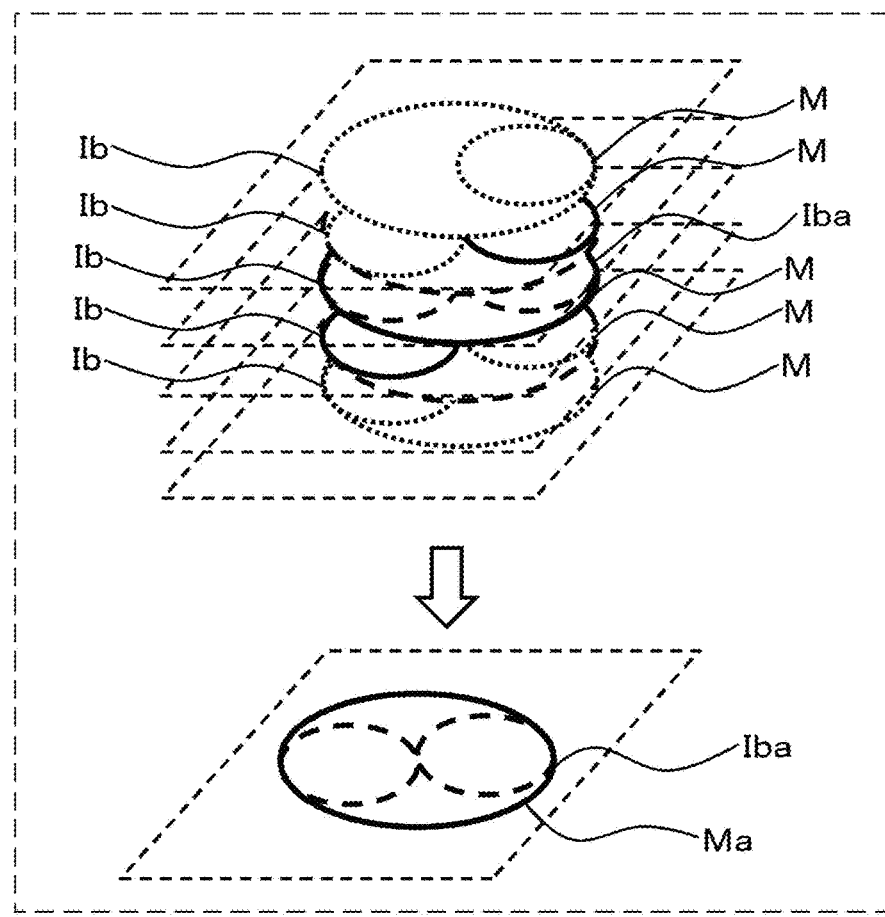
FIG. 22 is a schematic diagram illustrating an example of an outline reference in-focus image.

In step S2600, the 3D image generation unit 250 extracts an outline reference in-focus image Iba in which the object-showing region M of the embryo S has an outline having the highest contrast from among the plurality of background-removed in-focus images Ib as illustrated in FIG. 22. The 3D image generation unit 250 may determine which of a first outline reference in-focus image Iba1 and a second outline reference in-focus image Iba2 includes an outline having a higher contrast in the following manner. For example, the first outline reference in-focus image Iba1 includes a1 pixels determined to be an outline. The 3D image generation unit 250 determines, for each of the pixels determined to be an outline, the largest value from among the pixel value differences between the pixel and the plurality of adjacent pixels. Let A1 denote the sum of the largest values. For example, the second outline reference in-focus image Iba2 includes a2 pixels determined to be an outline. The 3D image generation unit 250 determines, for each of the pixels determined to be an outline, the largest value from among the pixel value differences between the pixel and the plurality of adjacent pixels. Let A2 denote the sum of the largest values. The 3D image generation unit 250 determines that the first outline reference in-focus image Iba1 includes an outline having a higher contrast than the second outline reference in-focus image Iba2 if $\{(A1)/(a1)\} > \{(A2)/(a2)\}$. FIG. 22 is a schematic diagram illustrating an example of the outline reference in-focus image Iba. The pixel value of a pixel that makes the contrast of the outline of the object-showing region M the highest corresponds to a pixel value obtained when the pixel of the image sensor 102 detects light that passes through the periphery of the embryo S and a region near the periphery when the embryo S is irradiated with light from directly above the embryo S in a direction perpendicular to the light-receiving surface of the image sensor 102. Accordingly, a circular outline Ma of the object-showing region M in the outline reference in-focus image Iba corresponds to an outline of a section that passes through the center of the embryo S, that is, a two-dimensional outline for the embryonic membrane of the embryo S, and corresponds to a planer outline of the embryo S when the embryo S is viewed in a direction perpendicular to the light-receiving surface of the image sensor 102. The 3D image generation unit 250 then extracts the outline Ma of the embryo S from the outline reference in-focus image Iba. In this way, the two-dimensional outline Ma of the embryo S is extracted. Which of the first outline reference in-focus image Iba1 and the second outline reference in-focus image Iba2 includes an outline having a higher contrast may be determined in the following manner. Let a1 denote an average pixel value of pixels of the first outline reference in-focus image Iba1 that are determined to be an outline, and let a2 denote an average pixel value of pixels of the second outline reference in-focus image Iba2 that are determined to be an outline. Let b1 denote an average pixel value of pixels that are adjacent to the pixel of the first outline reference in-focus image Iba1 that is determined to be an outline, and let b2 denote an average pixel value of pixels that are adjacent to the pixel of the second outline reference in-focus image Iba2 that is determined to be an outline. The 3D image generation unit 250 determines that the first outline reference in-focus image Iba1 includes an outline having a higher contrast than the second outline reference in-focus image Iba2 if $|a1-b1|>|a2-b2|$.

Figure 23:
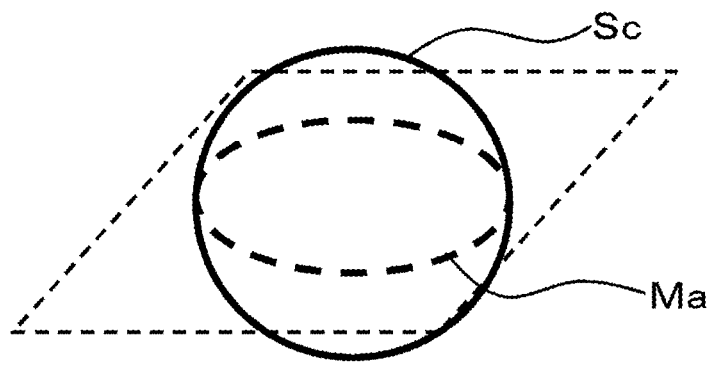
FIG. 23 is a schematic diagram illustrating an example of a three-dimensional (3D) outline of an embryo.

In step S2700, the 3D image generation unit 250 identifies a three-dimensional outline of the embryo S from the shape of the two-dimensional outline extracted from the outline reference in-focus image Iba and the shape of the embryo S stored in the first memory 121. For example, the first memory 121 stores information indicating that "the embryo S has a spherical shape". Specifically, the 3D image generation unit 250 identifies that the three-dimensional outline Sc of the embryo S is a sphere having a radius equal to the radius of the outline Ma from the circular outline Ma of the object-showing region M of the outline reference in-focus image Iba and the information stored in the first memory 121 indicating that the embryo S has a spherical shape as illustrated in FIGS. 22 and 23. FIG. 23 is a schematic diagram illustrating an example of the three-dimensional outline Sc of the embryo S.

In step S2800, the 3D image generation unit 250 generates reference sectional images Ic by associating the plurality of background-removed in-focus images Ib with the three-dimensional outline Sc of the embryo S and removing a region outside the three-dimensional outline Sc from the plurality of background-removed in-focus images Ib. The reference sectional images Ic correspond to sectional images of the embryo S at the plurality of reference focal planes FP determined in step S2200.

Figure 24:
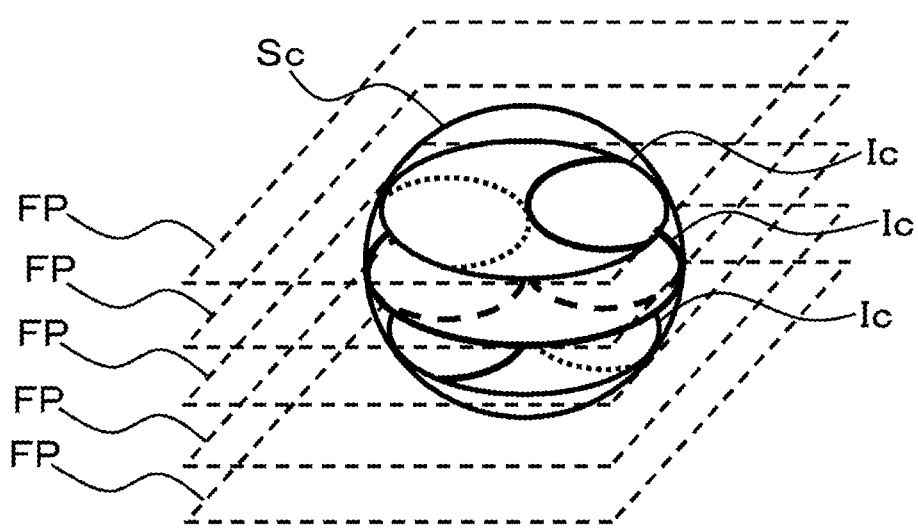
FIG. 24 is a diagram illustrating an example of a plurality of reference sectional images.
Figure 25:
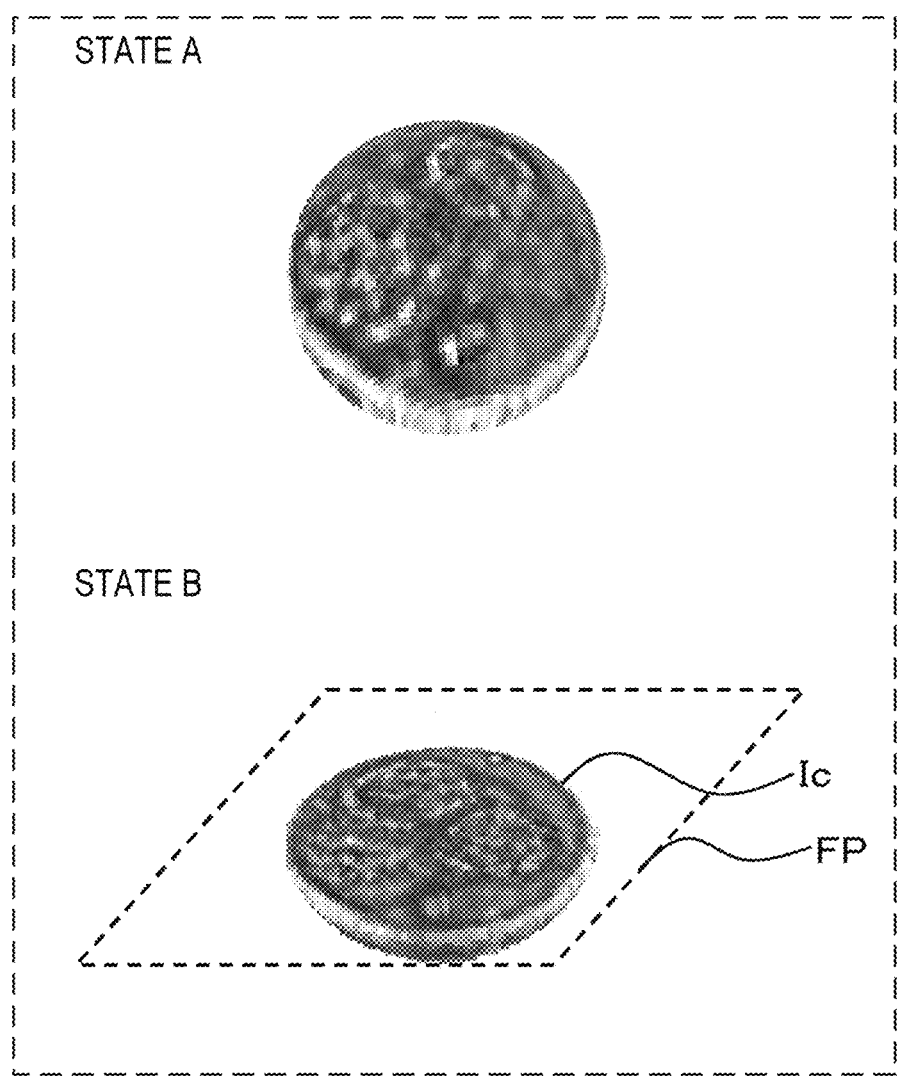
FIG. 25 is a diagram illustrating an example in which the plurality of reference sectional images are displayed using a photograph.

Specifically, the 3D image generation unit 250 identifies the positional relationship between the reference focal plane FP corresponding to each background-removed in-focus image Ib and the spherical outline Sc of the embryo S. At that time, the 3D image generation unit 250 determines that the reference focal plane FP including the outline reference in-focus image Iba is a plane that passes through the center of the three-dimensional outline Sc and that is substantially parallel to the light-receiving surface of the image sensor 102. The 3D image generation unit 250 further determines the position of the reference focal plane FP including another background-removed in-focus image Ib with respect to the three-dimensional outline Sc on the basis of the above determination. The 3D image generation unit 250 then removes a region outside the spherical outline Sc of the embryo S from the plurality of background-removed in-focus images Ib and generates the plurality of reference sectional images Ic as illustrated in FIG. 24. FIG. 24 is a schematic diagram illustrating an example of the plurality of reference sectional images Ic as in FIG. 18. FIG. 24 illustrates the plurality of reference sectional images Ic that are arranged in a line in the arrangement order of the reference focal planes FP. Each reference sectional image Ic is a sectional image of the embryo S at the corresponding reference focal plane FP. In addition, FIG. 25 illustrates an example in which the plurality of reference sectional images Ic obtained by removing a region outside the spherical outline Sc of the embryo S are displayed as an image on the display screen 151 of the display unit 150. FIG. 25 is a diagram illustrating an example in which the reference sectional images Ic are displayed using a photograph. All the reference sectional images Ic are illustrated in the state A of FIG. 25 and form the outer shape of the spherical outline Sc of the embryo S, whereas some of the reference sectional images Ic are displayed in the state B of FIG. 25.

The background-removed in-focus images Ib need not be generated in step S2500. For example, background outside the outline of the object-showing region M may be removed from the reference in-focus images Ia through processing for removing a region outside the spherical outline Sc of the embryo S in step S2800. That is, the processing of step S2500 may be included in the processing of step S2800. in this case, the processing of step S2600 to step S2800 is performed on the reference in-focus images Ia.

In step S2900, the 3D image generation unit 250 generates a 3D model A, which is a 3D model of the embryo S, as image data that can be output to a display or the like by using the three-dimensional outline Sc of the embryo S and the plurality of reference sectional images Ic. The 3D model A includes information regarding the spherical outline Sc of the embryo S and the plurality of reference sectional images Ic and includes the reference sectional images Ic as sectional images. The 3D model A is similar to that of the state A illustrated in FIG. 25 when it is displayed as an image on the display screen 151 of the display unit 150.

In step S3000, the image operation unit 260 displays the 3D model A of the embryo S generated by the 3D image generation unit 250 on the display unit 150 in an operable manner. The image operation unit 260 moves the 3D model A of the embryo S on the display unit 150 in accordance with an instruction input via the CG operation input unit 140. The image operation unit 260 accepts selection of a section at various positions of the embryo S via the CG operation input unit 140. Further, the image operation unit 260 may display a preview sectional image Bi, which is a brief image of the selected section, on the 3D model A of the embryo S or separately from the 3D model.

Figure 26A:
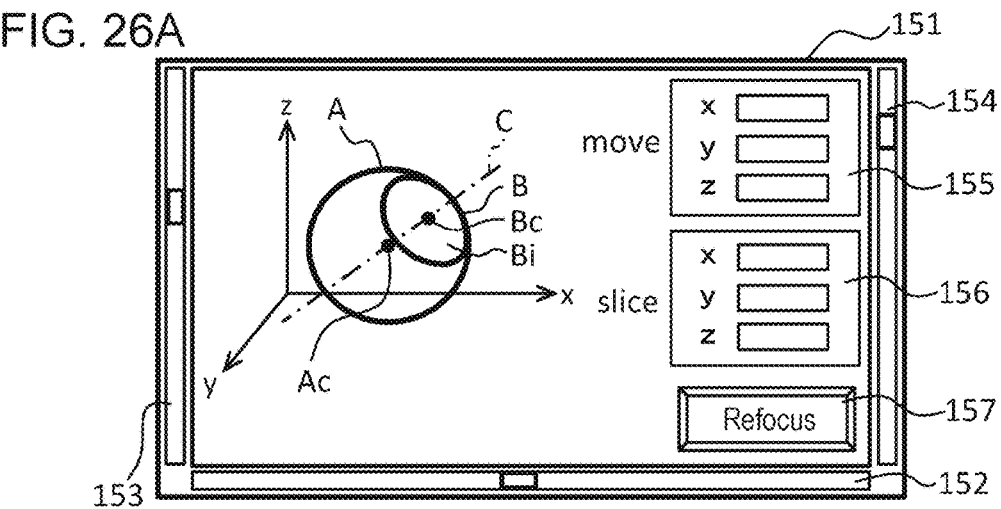
FIG. 26A is a diagram illustrating an example of a 3D model of the embryo displayed on a display screen of a display unit.
Figure 26B:
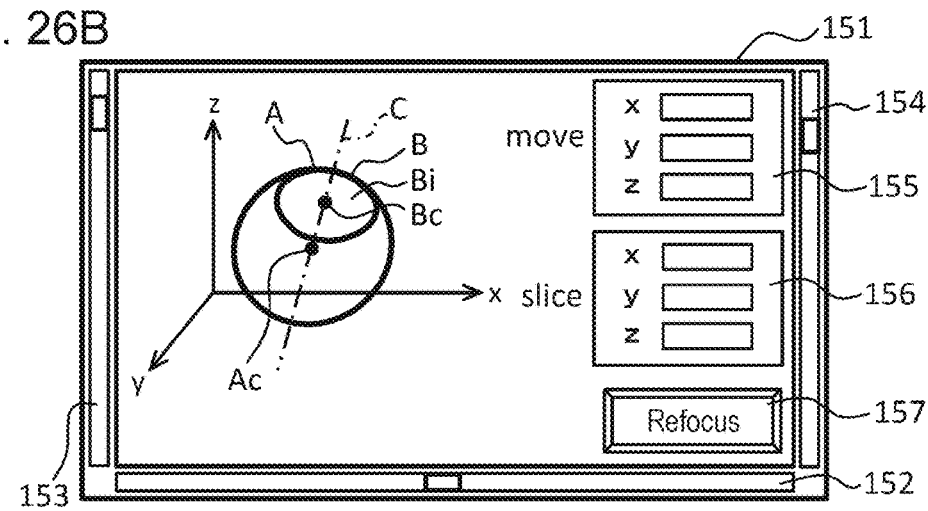
FIG. 26B is a diagram illustrating an example of the 3D model of the embryo displayed on the display screen of the display unit.
Figure 26C:
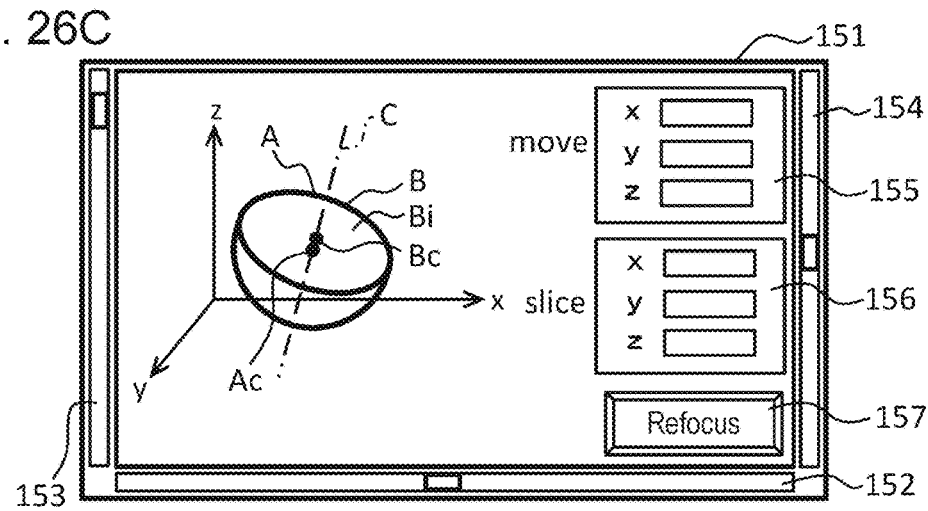
FIG. 26C is a diagram illustrating an example of the 3D model of the embryo displayed on the display screen of the display unit.

For example, the image operation unit 260 displays the 3D model A of the embryo S on the display screen 151 of the display unit 150 in an operable state as illustrated in FIGS. 26A, 26B, and 26C. Each of FIGS. 26A, 26B, and 26C is a diagram illustrating an example of the 3D model of the embryo S displayed on the display screen 151 of the display unit 150. The screen illustrated in FIGS. 26A, 26B, and 26C is a screen in which the user is allowed to select and display a section to be displayed in detail by using the 3D model A of the embryo S.

In the display screen 151, the position of the 3D model A of the embryo S is defined by using the xyz space. The x-y plane is set to be parallel to the light-receiving surface of the image sensor 102. Further, a reference axis C that passes through the center of the 3D model A of the spherical embryo S is set, and the orientation of the reference axis C is defined by using the xyz space. In addition, the position of a section B of the 3D model A of the embryo S that is perpendicular to the reference axis C is defined by using the xyz space.

As illustrated in FIGS. 26A and 26B, the reference axis C rotates with respect to the spherical center Ac of the 3D model A in the display screen 151 in accordance with an instruction input via the CG operation input unit 140, and consequently the orientation of the reference axis C is changed in any manner. A horizontal movement scroll bar 152 and a vertical movement scroll bar 153 are displayed near the edges of the display screen 151. The reference axis C rotates in a direction along the x-y plane with respect to the spherical center Ac of the 3D model A, that is, rotates around an axis parallel to the z axis that passes through the center of the 3D model A, in response to a scroll operation on the horizontal movement scroll bar 152. The reference axis C rotates in a direction along the y-z plane with respect to the center of the 3D model A, that is, rotates around an axis parallel to the x axis that passes through the center of the 3D model A in response to a scroll operation on the vertical movement scroll bar 153. In this way, the orientation of the reference axis C is changed in any given manner. In addition, the direction vector of the reference axis C is displayed by using the x, y, and z coordinates at a movement position display portion 155 located at an upper right portion of the display screen 151. The orientation of the reference axis C may be determined by inputting numerical values at fields of the x, y, and z coordinates of the movement position display portion 155. Note that the configuration used to move the reference axis C is not limited to the above one and any other configuration may be used.

Figure 27:
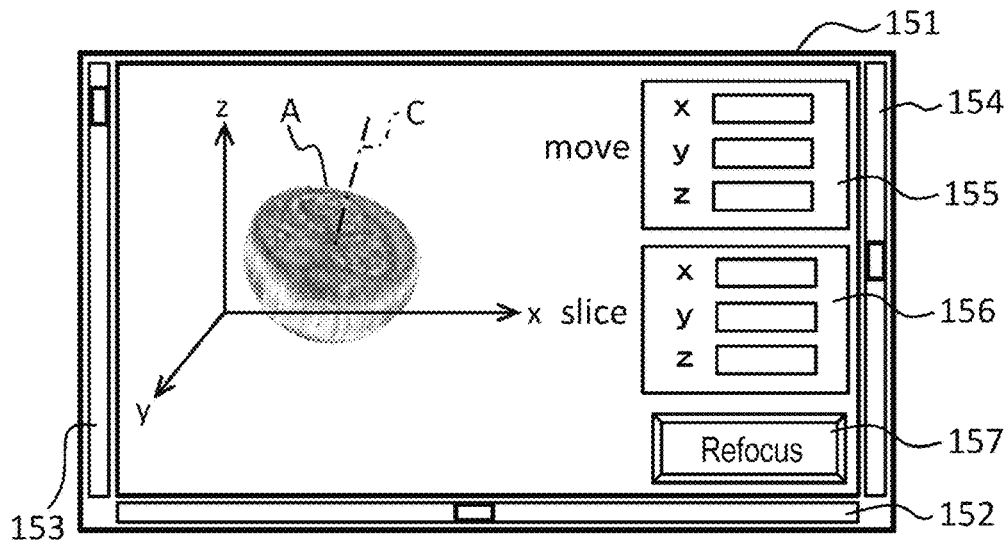
FIG. 27 is a diagram illustrating a screen in which part of the example displayed on the display screen in FIG. 26C is displayed using a photograph.

Further, the section B of the 3D model A slides along the reference axis C in the direction of the axis in any given manner in accordance with an instruction input via the CG operation input unit 140 as illustrated in FIGS. 26B and 26C. The preview sectional image Bi, which is a briefly created image of the section B, is displayed as the section B of the 3D model A with the displayed content being changed in accordance with the position of the section B. For example, FIG. 27 illustrates an example in which the 3D model A illustrated in FIG. 26C is displayed as an image on the display screen 151 of the display unit 150. FIG. 27 is a diagram illustrating an example in which part of the display screen 151 illustrated in FIG. 26C is displayed using a photograph. Note that the preview sectional image Bi may be displayed at a position different from that of the section B.

A section movement scroll bar 154 is displayed near an edge of the display screen 151. The section B including the preview sectional image Bi slides (translates) along the reference axis C with the displayed content being changed in response to a scroll operation on the section movement scroll bar 154. In addition, the position of the center Bc of the section B, which is the intersection point of the section B of the 3D model A and the reference axis C, is displayed by using the x, y, and z coordinates at a section position display portion 156 at a middle right portion of the display screen 151. The position of the section B may be determined by inputting numerical values in fields of the x, y, and z coordinates of the section position display portion 156. Note that the configuration for moving the section B is not limited to the above one, and any other configuration may be used.

The preview sectional image Bi at a given position of the 3D model A can be displayed on the display screen 151 of the display unit 150 by rotating the reference axis C and sliding the section B in combination. In this example, the reference axis C and the section B move but the 3D model A does not move; however, the 3D model A may be displayed so as to move such as to rotate. Any given configuration may be used as the configuration for changing the position of the section B.

The preview sectional image Bi is generated by using information included in the 3D model A, that is, information included in the plurality of reference sectional images Ic within the spherical outline Sc of the embryo S. For example, each pixel in a portion where the preview sectional image Bi crosses the reference focal plane FP of the reference sectional image Ic is displayed in the preview sectional image Bi of the section B by using a pixel value of the corresponding pixel of the reference sectional image Ic. Each pixel in a region other than the intersection region is displayed by using a pixel value of the corresponding pixel of the reference sectional image Ic located near the pixel or is not displayed. Accordingly, the preview sectional image Bi shows a brief image of the section B.

Upon being supplied with position information of the section of the embryo S to be displayed in detail, the image generation system 10 according to the first embodiment generates a detailed image of the section and displays the detailed image on the display unit 150. At that time, the sectional image generation unit 270 of the image generation device 200 generates a detailed image of the section and displays the detailed image on the display unit 150. The position information of the section of the embryo S to be displayed in detail may be supplied as a result of the preview sectional image Bi of the embryo S currently displayed on the display screen 151 of the display unit 150 being selected and determined via the CG operation input unit 140.

Figure 28:
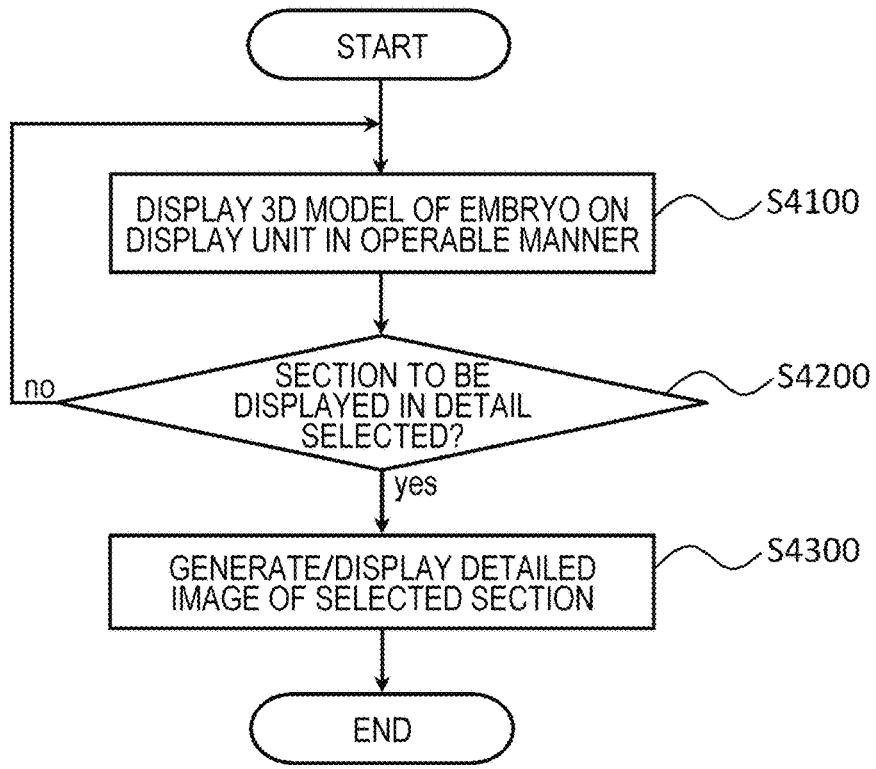
FIG. 28 is a flowchart illustrating an example of an operation performed by the image generation system according to the first embodiment to display a detailed sectional image of the embryo.

An example of an operation performed by the image generation system 10 to display a detailed sectional image of the embryo S will be described with reference to FIG. 28. FIG. 28 is a flowchart illustrating an example of an operation performed by the image generation system 10 according to the first embodiment to display a detailed sectional image of the embryo S. The following description will be given of an example in which the position of the section of the embryo S to be displayed in detail is determined by using the 3D model A of the embryo S displayed on the display unit 150.

In step S4100, the image operation unit 260 of the image generation device 200 displays the 3D model A of the embryo S so that operations, such as rotation of the reference axis C of the 3D model A and sliding of the section B, can be performed.

In step S4200, the image operation unit 260 rotates the reference axis C of the 3D model A of the embryo S or slides the section B on the display screen 151 of the display unit 150 in accordance with an instruction input via the CG operation input unit 150 as illustrated in FIGS. 26A to 26C and displays various preview sectional images Bi of the 3D model A. Then, if the position of the displayed section B is at a desired position or the displayed preview sectional image Bi is a desired section, that is, if the desired section or the position of the desired section is displayed on the display screen 151, the user inputs an instruction to display a detailed section via the CG operation input unit 140 (yes in step S4200). Consequently, the position of the section of the embryo S to be displayed in detail is determined. At that time, a refocus icon 157 of the display screen 151 is selected through input via the CG operation input unit 140 and the associated instruction is executed. As a result, the process proceeds to step S4300 so that the sectional image generation unit 270 generates the sectional image of the embryo S to be displayed. On the other hand, if an instruction associated with the refocus icon 157 is not executed, that is, if an instruction to display the section of the embryo S in detail is not issued (no in step S4200), the image operation unit 260 performs the operation of step S4100.

In step S4300, the sectional image generation unit 270 generates a detailed image of the determined section by using the position of the determined section and information included in the plurality of reference sectional images Ic. Specifically, the sectional image generation unit 270 generates an in-focus image by using the determined section as the focal plane through the refocusing process. That is, the sectional image generation unit 270 uses a pixel value of a corresponding pixel of the reference sectional image Ic as a pixel value of each pixel located in a region where the determined section overlaps or crosses the reference foal plane FP of the reference sectional image Ic. The sectional image generation unit 270 calculates a pixel value of each interpolation pixel, which is a pixel located in a region where the determined section neither overlaps nor crosses the reference focal plane FP of the reference sectional image Ic, by using pixel values of pixels of the reference sectional images Ic at the reference focal planes FP that are located near the interpolation pixel. The sectional image generation unit 270 then generates a detailed sectional image, which is an in-focus image of the determined section of the embryo S, as image data that can be output to a display or the like by using the pixel values of the pixels of the reference sectional images Ic and the pixel values of the interpolation pixels and displays the detailed sectional image on the display screen 151.

As described above, the user of the image generation system 10 is allowed to display a desired preview sectional image Bi or the position of the desired preview sectional image Bi of the 3D model A of the embryo S on the display screen 151 of the display unit 151 by operating the CG operation input unit 140. Further, the user is allowed to obtain a detailed sectional image of the preview sectional image Bi by operating the CG operation input unit 140 and selecting the displayed preview sectional image Bi or the position of the displayed preview sectional image Bi.

Figure 29:
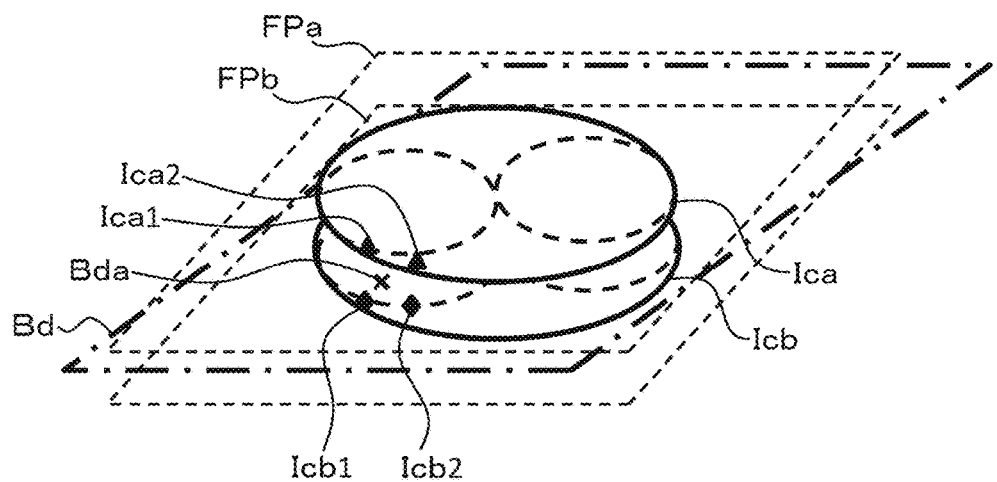
FIG. 29 is a diagram illustrating an example case where a pixel value of each pixel on a section of the embryo to be displayed in detail is estimated by using the corresponding pixels of reference sectional images at two reference focal planes that cross the section.
Figure 30:
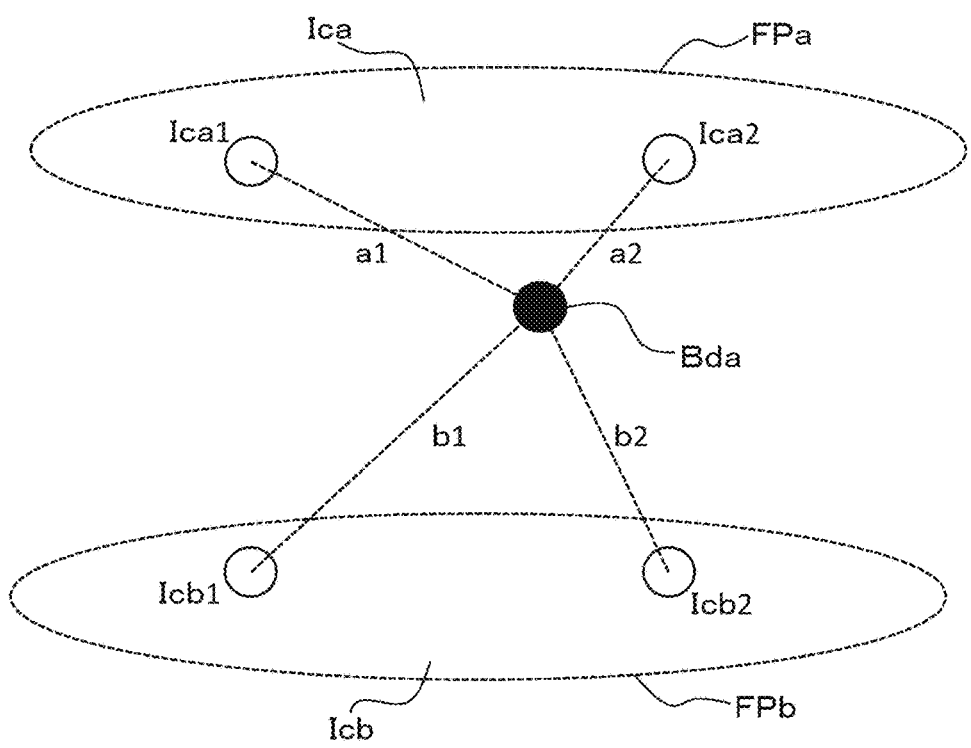
FIG. 30 is a diagram illustrating a relationship between a pixel on a section of the embryo to be displayed in detail and the corresponding pixels of the two reference sectional images, the relationship being used to calculate the pixel value of the pixel.

Now, a method for calculating a pixel value of a pixel of a section Bd to be displayed in detail in the case where the section Bd crosses the reference focal planes FP of the reference sectional images Ic will be described with reference to FIGS. 29 and 30. FIG. 29 is a diagram illustrating an example case where pixel values of pixels of the section Bd are estimated by using pixels of reference sectional images Ica and Icb respectively at two reference focal planes FPa and FPb that cross the section Bd to be displayed in detail. FIG. 30 is a diagram illustrating a relationship between a pixel of the section Bd to be displayed in detail and pixels of the two reference sectional images Ica and Icb that are used to calculate the pixel of the section Bd.

The section Bd crosses the reference focal planes FPa and FPb of the two reference sectional images Ica and Icb that are adjacent to each other. A pixel Bda of the section Bd for which a pixel value is to be estimated is an interpolation pixel located between the reference focal planes FPa and FPb. The reference focal planes FPa and FPb are in-focus image planes located near the position of the interpolation pixel Bda. The pixel value of the interpolation pixel Bda is estimated by using two pixels Ica1 and Ica2 of the reference sectional image Ica located near the position of the interpolation pixel Bda and two pixels Icb1 and Icb2 of the reference sectional image Icb located near the position of the interpolation pixel Bda. Accordingly, the reference focal planes FPa and FPb whose reference sectional images include pixels that influence the pixel value of the interpolation pixel Bda may be the ones that are the closest to the position of the interpolation pixel Bda.

As illustrated in FIG. 30, distances from the position of the interpolation pixel Bda to the pixels Ica1, Ica2, Icb1, and Icb2 are denoted by $a_1$, $a_2$, $b_1$, and $b_2$, respectively. Pixel values of the pixels Ica1, Ica2, Icb1, and Icb2 are denoted by $L_{a1}$, $L_{a2}$, $L_{b1}$, and $L_{b2}$. Accordingly, the pixel value $L_{Bda}$ of the interpolation pixel Bda is determined by using Equation 4 below.

$$L_{Bda} = \left(\frac{L_{a_1}}{a_1} + \frac{L_{a_2}}{a_2} + \frac{L_{b_1}}{b_1} + \frac{L_{b_2}}{b_2}\right) \times (a_1 + a_2 + b_1 + b_2) \quad \text{Equation 4}$$

Accordingly, the to-be-estimated pixel value $L_{Bda}$ of the interpolation pixel Bda of the section Bd is estimated by using pixel values of the pixels of the reference sectional images Ica and Icb at the two reference focal planes FPa and FPb that are adjacent to the pixel Bda.

The in-focus image of the section Bd to be displayed in detail is generated by using pixel values of pixels of the reference sectional images Ic located at a portion where the section Bd overlaps or crosses the respective reference focal planes FP of the reference sectional images Ic and pixel values of interpolation pixels that are calculated by using pixel values of pixels of the reference sectional images Ic of the reference focal planes FP that are adjacent to the interpolation pixels. Accordingly, the in-focus image of the section B is generated through a refocusing process in which information included in the reference sectional images Ic that are generated in advance is used. For this reason, the in-focus image of the section Bd is generated more easily and rapidly than in the case where the in-focus image is generated through a refocusing process using the plurality of captured images as in generation of the reference sectional images Ic. Note that three or more pixels of the reference sectional image Ica or three or more pixels of the reference sectional image Icb may be used to calculate the pixel value of the interpolation pixel Bda. In addition, the pixel value of each pixel on the section Bd is also successfully calculated in a manner similar to the above-described one when the section Bd to be displayed in detail is parallel to the reference focal plane FP of the reference sectional image Ic.

1-3. Advantageous Effects

As described above, the image generation device 200 according to the first embodiment is capable of generating a plurality of reference in-focus images corresponding to a plurality of reference focal planes that pass through the embryo S serving as an object and of generating a three-dimensional image of the embryo S by using the generated reference in-focus images. The use of the reference in-focus images corresponding to the plurality of reference focal planes that pass through the embryo S may allow a three-dimensional image of the embryo S to be displayed three-dimensionally including constituents, such as cells, included in the embryo S even if the embryo S is translucent or transparent. In addition, since the in-focus images are generated for the plurality of reference focal planes instead of generating the in-focus images for the entire region of the embryo S, an amount of processing needed to generate the three-dimensional image of the embryo S can also be reduced.

In addition, the image generation device 200 according to the first embodiment allows a given section to be selected by using the three-dimensional image of the embryo S and allows an image of the selected section to be displayed. Since pixel values of a plurality of section pixels of a sectional image of the embryo S are calculated using pixel values of the corresponding pixels of the reference in-focus image located at the section pixels or pixel values of pixels of the reference in-focus images located near the section pixels, the sectional image of the embryo S can be a sharp image in which discontinuity and blur are reduced. Further, since pixel values of the section pixels of the sectional image of the embryo S are calculated by using pixels of the reference in-focus images of reference focal planes located on the respective sides of the section pixels, the pixel values of the section pixels can be highly accurate.

In addition, the image generation device 200 according to the first embodiment generates a preview sectional image representing a section of the embryo S for preview and displays the preview sectional image on the display screen. Pixel values of a plurality of pixels of the preview sectional image can be pixel values of respective pixels of the reference in-focus images located at the pixels of the preview sectional image. Thus, the user is allowed to select a to-be-displayed section of the embryo S with reference to the preview sectional image. In addition, since pixel values of pixels of the preview sectional image are pixel values of the respective pixels of the reference in-focus images, the preview sectional image is generated easily.

In addition, the image generation device 200 according to the first embodiment calculates a pixel value of each in-focus pixel by using, as the pixel value of the in-focus pixel, a pixel value obtained by each sensor pixel that satisfies a relationship in which the position of the illuminator 101, the position of the in-focus pixel in the reference in-focus image, and the position of the sensor pixel of the image sensor 102 are on a line. Accordingly, pixel values of a plurality of captured images corresponding to each pixel of the in-focus image at the focal plane are successively reflected in the pixel, and a high-quality in-focus image of the embryo S is successfully generated.

Second Embodiment

A second embodiment will be described next. In the second embodiment, the image generation system displays an optimum sectional image, which is a representative sectional image of the embryo S, on the display screen 151 of the display unit 150 prior to the 3D model A of the embryo S, which differs from the first embodiment. The second embodiment will be described below in terms of differences from the first embodiment.

2-1. Configuration of Image Generation System

Figure 31:
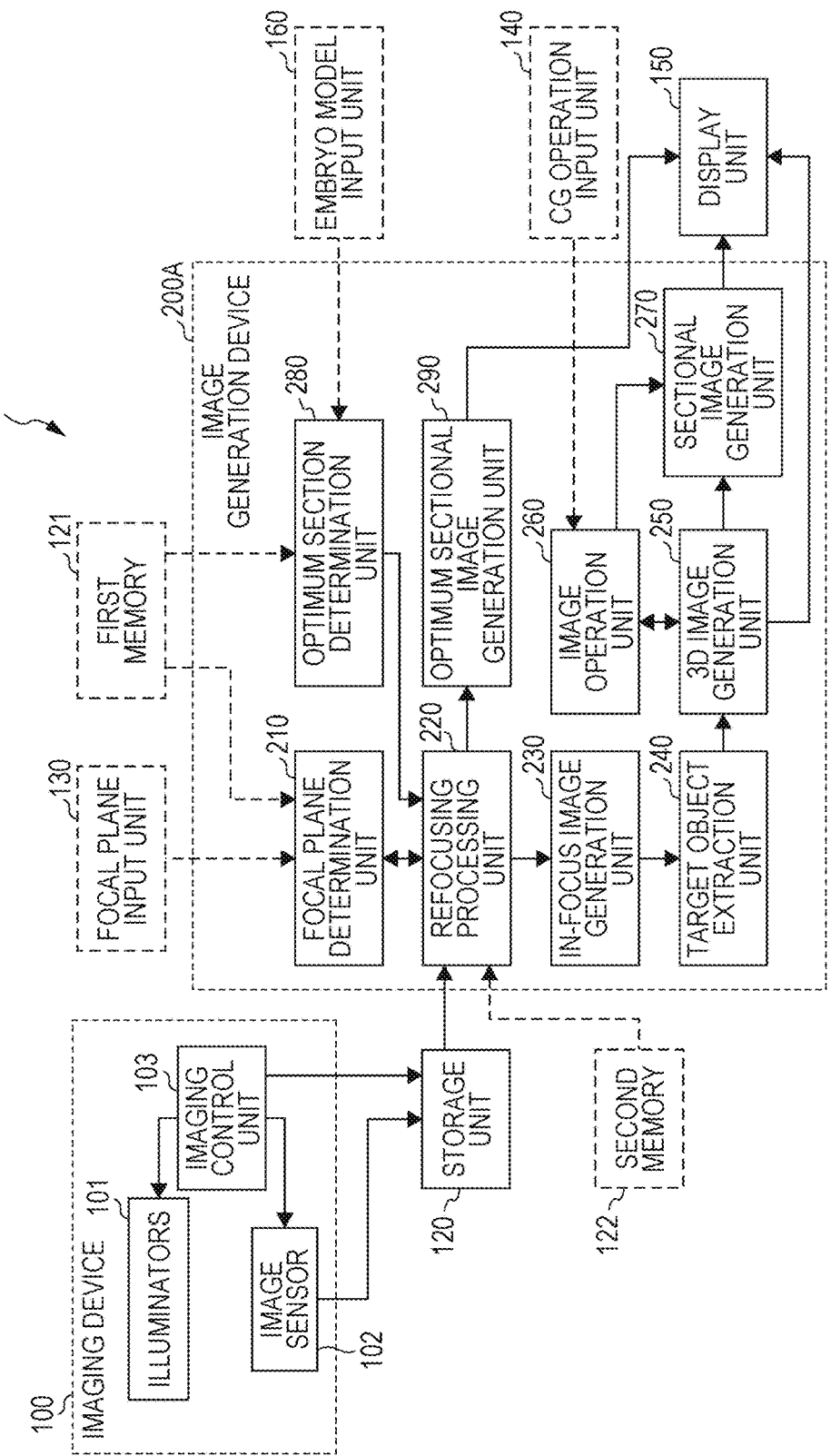
FIG. 31 is a block diagram illustrating an example of the functional configuration of an image generation system according to a second embodiment.

FIG. 31 is a block diagram illustrating an example of the functional configuration of an image generation system 10A according to the second embodiment. In the second embodiment, the plurality of illuminators 101 of the imaging device 100 are arranged in a grid pattern on a flat surface. An image generation device 200A further includes an optimum section determination unit 280 and an optimum sectional image generation unit 290, compared with the image generation device 200 of the image generation system 10 according to the first embodiment. The first memory 121 stores early embryo models of the embryo S in advance in addition to information regarding predetermined focal planes and the shape of the embryo S, which is an object to be imaged. The image generation system 10A includes an embryo model input unit 160 that accepts input of an instruction to select a model of the embryo S to be displayed on the display unit 150 from among the early embryo models stored in the first memory 121.

The early embryo models of the embryo S stored in the first memory 121 include information regarding the number of cells included in the embryo S. For each early embryo model of the embryo S, the number of cells included in the embryo S and a culture period from the start of culturing of the embryo S may be stored in association with each other. In this case, the early embryo models of the embryo S may be stored as a table illustrated in FIG. 32. FIG. 32 illustrates an example of the early embryo models stored in the first memory 121. In the example illustrated in FIG. 32, the model ID of each early embryo model, the culture period which indicates a period from the start of culturing of the embryo S, the number of cells included in the embryo S in the culture period, and an illustrative schematic diagram of the embryo S in the culture period are stored in combination with one another.

The optimum section determination unit 280 is implemented by, for example, a control circuit or a processor. The optimum section determination unit 280 determines the optimum section of the embryo S to be initially displayed as an example when the embryo S is displayed on the display unit 150. At that time, the optimum section determination unit 280 determines the number of candidate optimum sections and the number of cells that can be included in the optimum section on the basis of the number of cells included in an embryo model selected via the embryo model input unit 160. The optimum section determination unit 280 calculates the position of the optimum section on the basis of the determined elements and sends information representing the position of the optimum section to the refocusing processing unit 220.

Specifically, the optimum section determination unit 280 refers to an optimum section setting table, such as the one illustrated in FIG. 33, stored in the first memory 121 in advance, and determines the elements regarding the optimum section on the basis of this optimum section setting table. After determining the elements, the optimum section determination unit 280 determines the position of the optimum section of the embryo S in a manner described later. FIG. 33 illustrates an example of the optimum section setting table stored in the first memory 121. In the example illustrated in FIG. 33, the number of cells included in the embryo S, the number of candidate optimum sections (i.e., the number of candidate optimum focal planes), and the largest number of cells possibly included in an optimum sectional image which is a sectional image of the embryo S at the optimum focal plane are stored in combination with one another.

In the optimum section setting table illustrated in FIG. 33, if there is only one candidate optimum focal plane and the optimum focal plane passes through the center of a cell included in the embryo S or a region of 5 μm from the center, the largest number of cells which the optimum focal plane passes through is used as the largest number of cells possibly included in the optimum sectional image at the optimum focal plane. Alternatively, if the optimum focal plane passes through a position at which distances from the respective centers of individual cells become the smallest, the largest number of cells which the optimum focal plane can pass through is used as the largest number of cells possibly included in the optimum sectional image at the optimum focal plane. At that time, a situation where distances from the respective centers of individual cells become the smallest may indicate a situation where the sum of the distances from the respective centers of the individual cells becomes the smallest.

If there are two or more candidate optimum focal planes, the number of optimum focal planes is set in accordance with the number of cells included in the embryo S. Further, if the optimum focal plane passes through a position at which distances from the respective centers of individual cells become the smallest, the largest number of cells which the optimum focal plane can pass through is used as the largest number of cells possibly included in the optimum sectional image at the optimum focal plane. At that time, a situation where distances from the respective centers of a plurality of cells become the smallest may indicate a situation where the sum of the distances from the respective centers of the plurality of cells becomes the smallest or the sum of the distances from the respective centers of all the cells becomes the smallest.

The optimum sectional image generation unit 290 is implemented by, for example, a control circuit or a processor. The optimum sectional image generation unit 290 generates an in-focus image at the optimum focal plane, that is, an optimum sectional image, from pixel values of respective pixels calculated by the refocusing processing unit 220 and displays the optimum sectional image on the display unit 150.

2-2. Operation of Image Generation System

Figure 34:
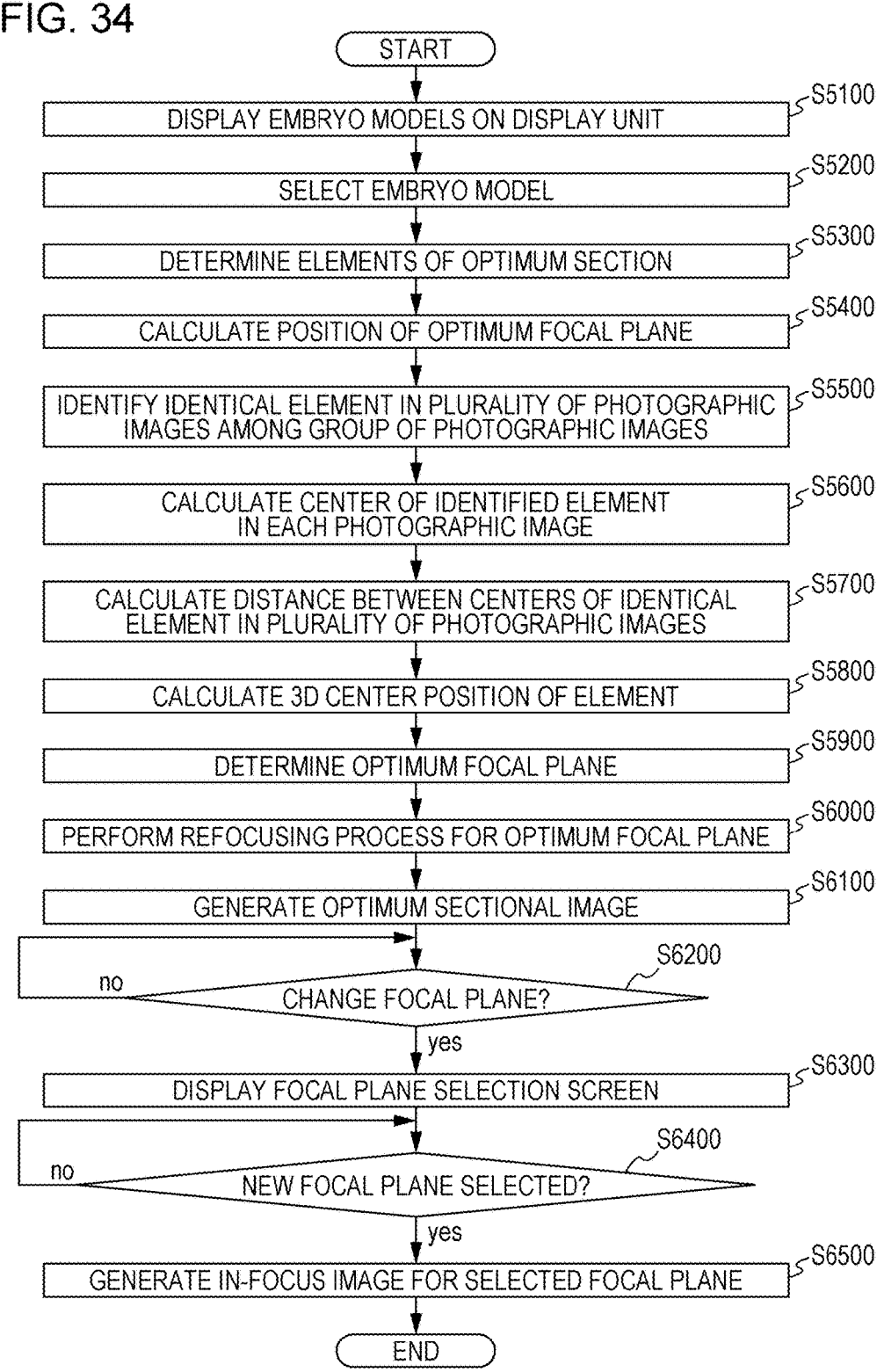
FIG. 34 is a flowchart illustrating an example of an operation performed by the image generation system according to the second embodiment to display an optimum sectional image.

An operation performed by the image generation system 10A thus configured to display an optimum sectional image on the display unit 150 will be described. FIG. 34 is a flowchart illustrating an example of the operation performed by the image generation system 10A according to the second embodiment to display an optimum sectional image. The following description will be given of the case where the embryo S includes two cells S1 and S2 as illustrated in FIG. 17.

In step S5100, the optimum section determination unit 280 of the image generation device 200A of the image generation system 10A displays on the display unit 150 embryo models of the embryo S stored in the first memory 121.

In step S5200, the user of the image generation system 10A refers to a table of the embryo models of the embryo S, such as the one illustrated in FIG. 32, that is displayed on the display unit 150 and selects a model ID of the embryo S for which the optimum sectional image is to be displayed on the display unit 150 via input using the embryo model input unit 160. At that time, the user may select the embryo model corresponding to the time of imaging by comparing the culture period of the embryo S at the time of imaging using the illuminators 101 with the culture period included in the table of the embryo models.

In step S5300, the optimum section determination unit 280 determines elements of the optimum section, that is, the optimum focal plane, on the basis of the number of cells included in the selected embryo model and the optimum section setting table, such as the one illustrated in FIG. 33, that is stored in the first memory 121. Specifically, the optimum section determination unit 280 determines the number of optimum focal planes and the largest number of cells possibly included in a sectional image at the optimum focal plane.

Figure 35:
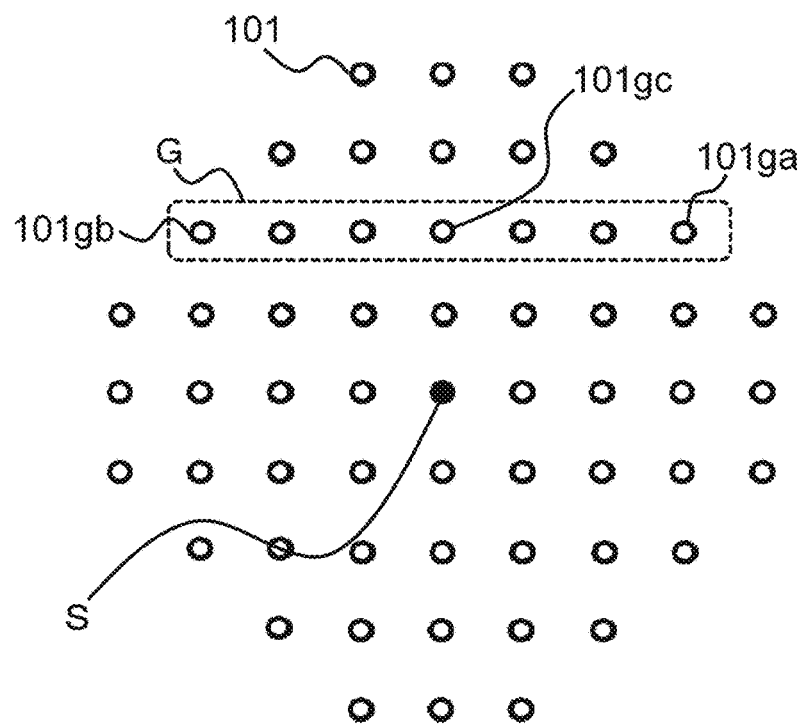
FIG. 35 is a plan view of a plurality of illuminators viewed in a direction from the illuminators toward an image sensor.

In step S5400, the optimum section determination unit 280 then determines the position of the optimum focal plane in the embryo S. At that time, the optimum section determination unit 280 obtains, from the storage unit 120, a plurality of captured images each associated with position information of a corresponding one of the plurality of illuminators 101. The optimum section determination unit 280 further selects an illuminator group G including illuminators 101 arranged in a line from among the plurality of illuminators 101 arranged in a grid pattern on a flat surface as illustrated in FIG. 35. The optimum section determination unit 280 selects captured images captured when the illuminators 101 belonging to the illuminator group G have radiated light from among the obtained captured images and form a captured image group including the selected captured images. FIG. 35 is a diagram illustrating how the plurality of illuminators 101 are arranged when the plurality of illuminators 101 are viewed in a direction from the illuminators 101 toward the image sensor 102. The illuminators 101 denoted by circles in FIG. 35 are point light sources and are implemented by, for example, a light source and a pinhole having a diameter of 10 μm. Each circle in FIG. 35 indicates the center position of the illuminator 101. The embryo S is placed substantially directly below the illuminator 101 denoted by a black circle in FIG. 35. The embryo S has a diameter of approximately 100 μm. Further, the optimum section determination unit 280 extracts lines that match the shape of the embryo S and the shapes of the two cells S1 and S2 included in the embryo S in each of the captured images belonging to the captured image group. Specifically, since all of the embryo S and the two cells S1 and S2 have a spherical shape, the optimum section determination unit 280 extracts, from each of the captured images, a circle representing the embryo S and circles representing the two cells S1 and S2 included in the circle representing the embryo S. The outline of the embryo S is identified in the following manner, for example. The shape of the embryo S is substantially spherical, and the diameter of the embryo S is approximately 100 μm. To extract edge points, a Laplacian filter is applied to the reference in-focus image Ia. The filtering results are classified based on a threshold. The threshold is set, for example, based on an intensity distribution of the input image (the reference in-focus image Ia in this case). For example, the threshold is set to a value at which the ratio of the number of low-intensity pixels to the number of all pixels is equal to 25% based on the intensity histogram. Pixels having pixel values that are smaller than or equal to the threshold are extracted as edge points. Hough transform is performed on the extracted edge points to extract circles. At that time, a circle is extracted by setting the diameter to a value in a range from 80 μm to 120 μm, for example. Consequently, a circle corresponding to the embryo S is extracted. Since the center and the radius of the circle are derived through Hough transform, a circle representing the outline is successfully identified in the reference in-focus image Ia. The cells S1 and S2 are extracted by performing Hough transform by using edge points located in the circle representing the determined outline of the embryo S. During Hough transform, circles are extracted by setting the diameter to a value in a range from 30 μm to 60 μm. Two circles are extracted with overlapping permitted.

Figure 36:
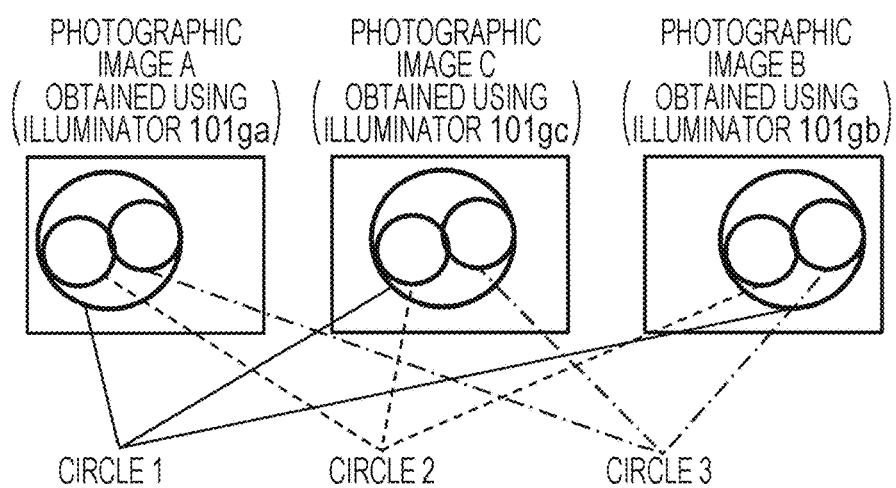
FIG. 36 is a diagram illustrating a correspondence of each identical element in a plurality of captured images belonging to a group of captured images.

In step S5500, the optimum section determination unit 280 identifies identical elements included in the plurality of captured images belonging to the captured image group. For example, the optimum section determination unit 280 identifies circles 1 representing the shape of the embryo S, circles 2 representing the shape of the first cell S1 among the two cells included in the embryo S, and circles 3 representing the shape of the second cell S2 among the two cells in association with each other in a plurality of photographic images A, B, and C belonging to the captured image group. FIG. 36 is a diagram illustrating a correspondence between identical elements in the plurality of photographic images A, B, and C belonging to the captured image group. The photographic images A, B, and C are used in FIG. 36; however, all of the plurality of photographic images belonging to the captured image group may be used. At that time, the optimum section determination unit 280 may identify the circles 1, 2, and 3 by using a condition that the circle 1 including the circles 2 and 3 does not cross the circles 2 and 3. Further, the optimum section determination unit 280 may identify the circles 1, 2, and 3 using a condition that the identical circles have substantially the same size and the positions of the identical circles are shifted based on a rule in the plurality of photographic images.

Referring to FIGS. 35 and 36, the photographic image A is an image captured when an illuminator 101ga located at one end of the illuminator group G is used for illumination. The photographic image B is an image captured when an illuminator 101gb located at the other end of the illuminator group G is used for illumination. The photographic image C is an image captured when an illuminator 101gc located at the center of the illuminator group G is used for illumination. Accordingly, the positions of the circles 1, 2, and 3 are shifted based on a rule from the photographic image A to the photographic image B.

Figure 37:
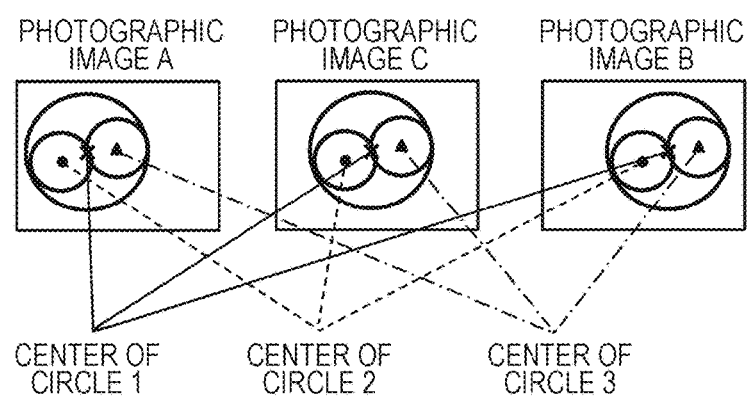
FIG. 37 is a diagram illustrating the positions of the center of each identical element in the plurality of captured images.

In step S5600, the optimum section determination unit 280 calculates the positions of the centers, which is feature points of the circles 1, 2, and 3 identified in the photographic images A, B, and C, as illustrated in FIG. 37. The optimum section determination unit 280 may determine, as the position of the center of each circle, a point that is located at substantially the same distance from a plurality of points on the circumference of the identified circle. FIG. 37 is a diagram illustrating the positions of the centers of the respective elements in the photographic images A, B, and C. The positions of the centers of the circles 1, 2, and 3 correspond to positions of corresponding pixels on the light-receiving surface of the image sensor 102. Accordingly, the optimum section determination unit 280 may calculate relative positions of the centers of the circles 1, 2, and 3 in the photographic images A, B, and C. Here, each of the center of the circle 2 representing the first cell S1 and the center of the circle 3 representing the second cell S2 is an example of a feature point of a second object in a photographic image. However, the feature point of the second object in the photographic image is not limited to the center of the circle. If the second object does not have a spherical shape unlike the cells S1 and S2, a point whose position can be identified, such as the centroid, the incenter, the circumcenter, the orthocenter, an apex, or a corner point may be used as the feature point. For example, when the second object has a polygonal shape, a feature point such as the centroid, the incenter, the circumcenter, the orthocenter, or an apex is set for the second object in the photographic images. Through the processing of steps S5500 and S5600, feature points of the embryo S, the cell S1, and the cell S2 in the photographic images are associated with each other. In this example, feature points of the embryo S, the cell S1, and the cell S2 are set in each photographic image after the embryo S, the cell S1, and the cell S2 in the photographic images are associated with each other; however, the configuration is not limited to this one. The embryo S, the cell S1, and the cell S2 and feature points of the embryo S, the cell S1, and the cell S2 may be associated with each other in the photographic images after the feature points of the embryo S, the cell S1, and the cell S2 are set in the photographic images.

Figure 38:
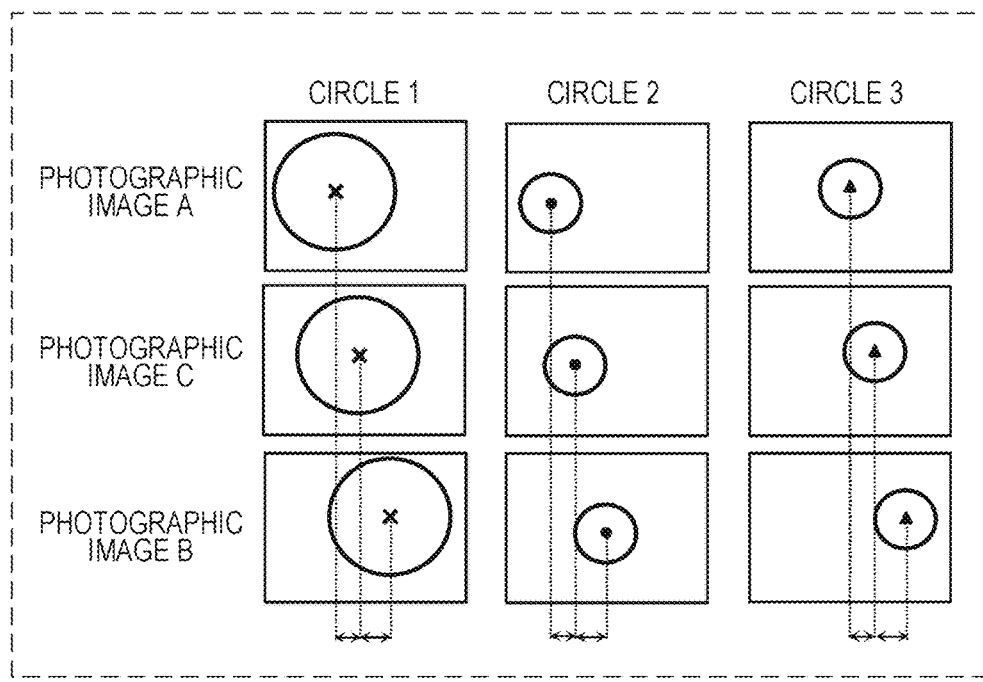
FIG. 38 is a diagram illustrating a positional relationship among the centers of each identical element in the plurality of captured images.

In step S5700, the optimum section determination unit 280 calculates distances between the center positions of the same circle in the photographic images A, B, and C. That is, the optimum section determination unit 280 calculates a positional relationship between the centers of the same circle in the photographic images A, B, and C. Specifically, as illustrated in FIG. 38, the optimum section determination unit 280 calculates distances between the center positions of the circle 1 in the photographic images A, B, and C, that is, shift amounts of the center positions of the circle 1 in the photographic images A, B, and C. Likewise, the optimum section determination unit 280 calculates distances between the center positions of the circle 2 in the photographic images A, B, and C. Further, the optimum section determination unit 280 calculates distances between the center positions of the circle 3 in the photographic images A, B, and C. FIG. 38 is a diagram illustrating the positional relationship between the centers of each element in the photographic images A, B, and C. The distances between the center positions of the same circle in the photographic images A, B, and C indicate distances between three parallel lines each passing through the center of the circle. In FIG. 38, the distances between the center positions of the same circle in the photographic images A, B, and C are the distances along a direction in which the illuminators 101 belonging to the illuminator group G are arranged.

Figure 39:
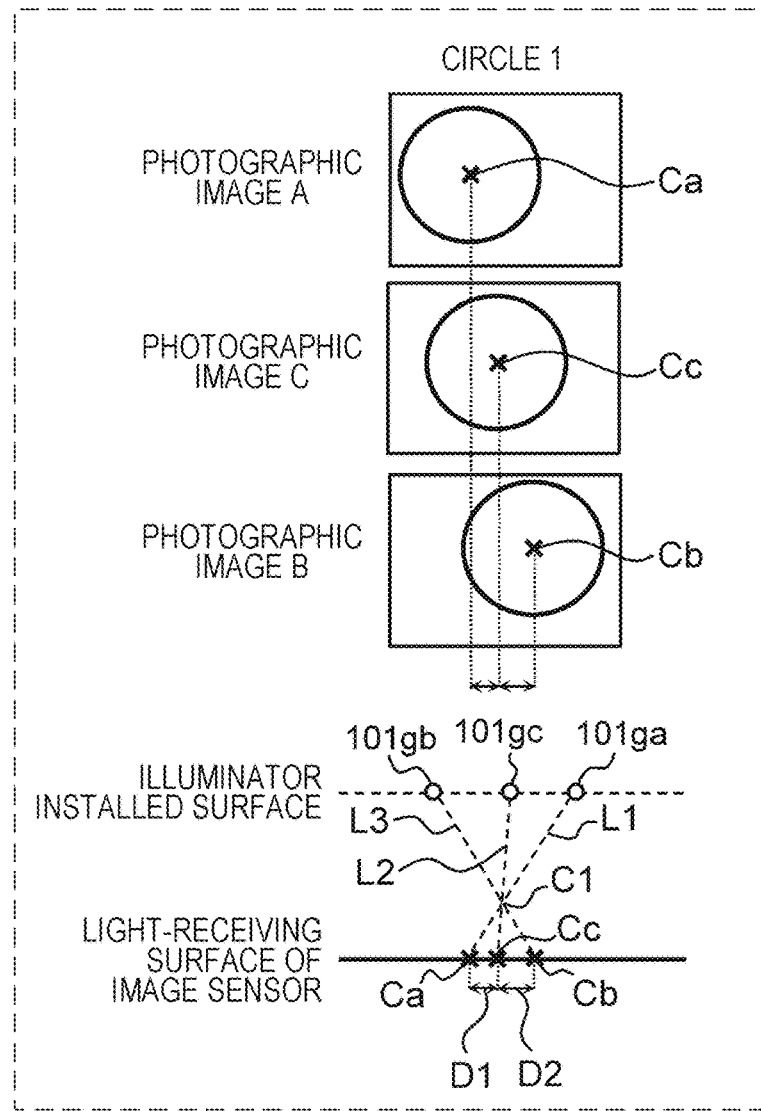
FIG. 39 is a diagram illustrating a positional relationship among the centers of the identical element in the plurality of photographic images and illuminators.

In step S5800, the optimum section determination unit 280 calculates the position of the center of the sphere that represents the shape of each of the embryo S, the first cell S1, and the second cell S2 from the distances between center positions of the corresponding circle in the photographic images A, B, and C and the positions of the illuminators 101 corresponding to the respective photographic images A, B, and C. For example, as illustrated in FIG. 39, a center Ca of the circle 1 in the photographic image A, a center Cb of the circle 1 in the photographic image B, and a center Cc of the circle 1 in the photographic image C are arranged on the light-receiving surface of the image sensor 102 in accordance with a distance D1 between the center Ca and the center Cc and a distance D2 between the center Cc and the center Cb. FIG. 39 is a diagram illustrating a positional relationship between the centers of an element in the photographic images A, B, and C and the corresponding illuminators 101.

In this case, the centers Ca, Cb, and Cc can be arranged substantially in a line. The position of the illuminator used for capturing the photographic image A, that is, the position of the illuminator 101ga corresponding to the photographic image A, and the center Ca are connected by a line L1. Similarly, the position of the illuminator 101gb corresponding to the photographic image B and the center Cb are connected by a line L3. The position of the illuminator 101gc corresponding to the photographic image C and the center Cc are connected by a line L2. The optimum section determination unit 280 determines the position of an intersection point C1 of the lines L1, L2, and L3 as the position of the three-dimensional center of the embryo S. The height of the intersection point C1 of the lines L1, L2, and L3 from the light-receiving surface of the image sensor 102 is the height of the center of the embryo S. If the lines L1, L2, and L3 do not cross at a single point, the position at which the sum of distances to the lines L1, L2, and L3 is the smallest may be set as the center position of the embryo S. The optimum section determination unit 280 also performs the similar processing for the circles 2 and 3 and calculates the center positions of the first cell S1 and the second cell S2.

Figure 40:
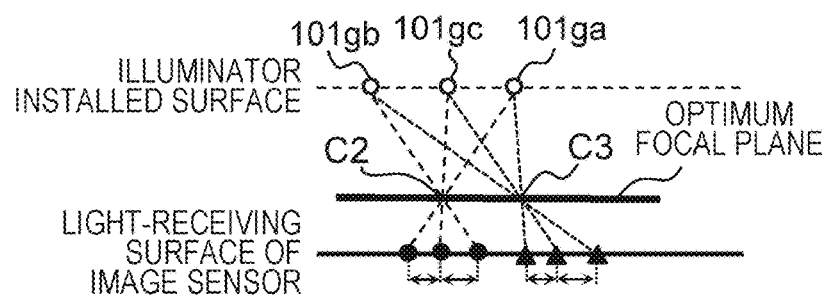
FIG. 40 is a diagram illustrating a positional relationship between the centers of two cells of the embryo.

In step S5900, the optimum section determination unit 280 determines a plane including the center of the first cell S1 and the center of the second cell S2 as the optimum focal plane, that is, the optimum section. For example, as illustrated in FIG. 40, the three-dimensional position of the center C2 of the first cell S1 is calculated based on the positions of the three centers of the circle 2 representing the first cells S1 in the photographic images A, B, and C and the positions of the illuminators 101ga, 101gb, and 101gc in step S5800. Similarly, the three-dimensional position of the center C3 of the second cell S2 is calculated based on the three center positions of the circle 3 representing the second cell S2 in the photographic images A, B, and C and the positions of the illuminators 101ga, 101gb, and 101gc. FIG. 40 is a diagram illustrating a positional relationship between the centers C2 and C3 of the two cells S1 and S2 included in the embryo S. In the second embodiment, since the embryo S includes two cells S1 and S2, a plane including the center of the first cell S1 and the center of the second cell S2 is determined as the optimum section. When the embryo S includes three or more cells, a plane including the centers of the largest number of cells among the centers of the plurality of cells may be determined as the optimum section. In addition, a plane for which the sum of lengths of perpendicular lines from the respective centers of the plurality of cells to the plane is the smallest may be determined as the optimum section.

The optimum section determination unit 280 determines a plane that passes through the centers C2 and C3 as the optimum focal plane. At that time, the optimum section determination unit 280 may determine the optimum focal plane so that the optimum focal plane has a tilt closer to a tilt of a plane that is parallel to the light-receiving surface of the image sensor 102 from among planes that pass through the centers C2 and C3. Specifically, the optimum section determination unit 280 may determine the optimum focal plane so that the optimum focal plane has a tilt angle of 10 degree or less with respect to a plane that is parallel to the light-receiving surface of the image sensor 102.

When the embryo S includes three or more cells, the optimum section determination unit 280 may determine the optimum focal plane so that the optimum focal plane includes a largest number of centers of the cells for which the position of the center is derived by performing processing similar to the above one. In addition to or separately from the above condition, the optimum section determination unit 280 may determine the optimum focal plane so that distances from the centers of all of the cells to the optimum focal plane become the smallest, that is, the sum of the distances from the centers of all of the cells becomes the smallest. In addition to or separately from the above condition, the optimum section determination unit 280 may determine the optimum focal plane so that the optimum focal plane passes through the centers of three cells among the cells for which the position of the center is successfully determined by performing processing similar to the above one and distances from the centers of the other cells to the optimum focal plane become the smallest. Further, the optimum section determination unit 280 may determine the optimum focal plane so that the optimum focal plane has a tilt closer to a tilt of a plane that is parallel to the light-receiving surface of the image sensor 102 during the determination.

In addition, when there are two or more candidate optimum focal planes as illustrated in FIG. 33, the optimum plane determination unit 280 may calculate two optimum focal planes and employ both or one of the two optimum focal planes. In addition, regarding display of the optimum sectional image at the optimum focal plane described below, optimum sectional images at two optimum focal planes may be displayed or an optimum sectional image at one of the two optimum focal planes may be displayed.

In step S6000, the optimum section determination unit 280 sends position information of the determined optimum focal plane to the refocusing processing unit 220. The refocusing processing unit 220 performs the refocusing process by using the photographic images stored in the storage unit 120 on the basis of the plurality of photographic images, the position information regarding the plurality of illuminators 101, and the position information regarding the optimum focal plane and determines pixel values of pixels at the optimum focal plane. The refocusing processing unit 220 may determine pixel values of the pixels at the optimum focal plane by using information included in the reference sectional images Ic at the respective reference focal planes FP as in the sectional image generation operation performed by the sectional image generation unit 270 in the first embodiment.

Figure 41:
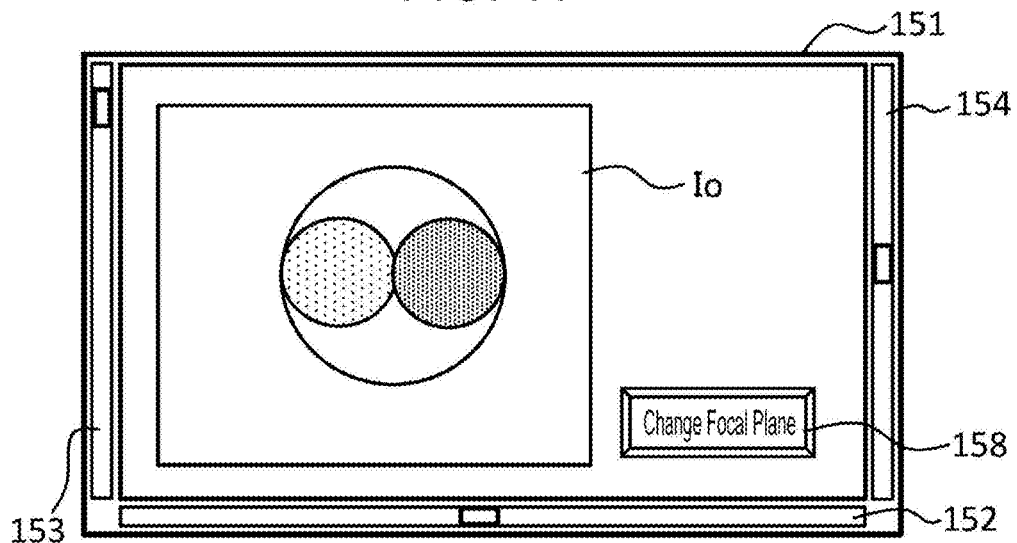
FIG. 41 illustrates an example in which the optimum sectional image of the embryo is displayed on a display screen of a display unit.
Figure 42:
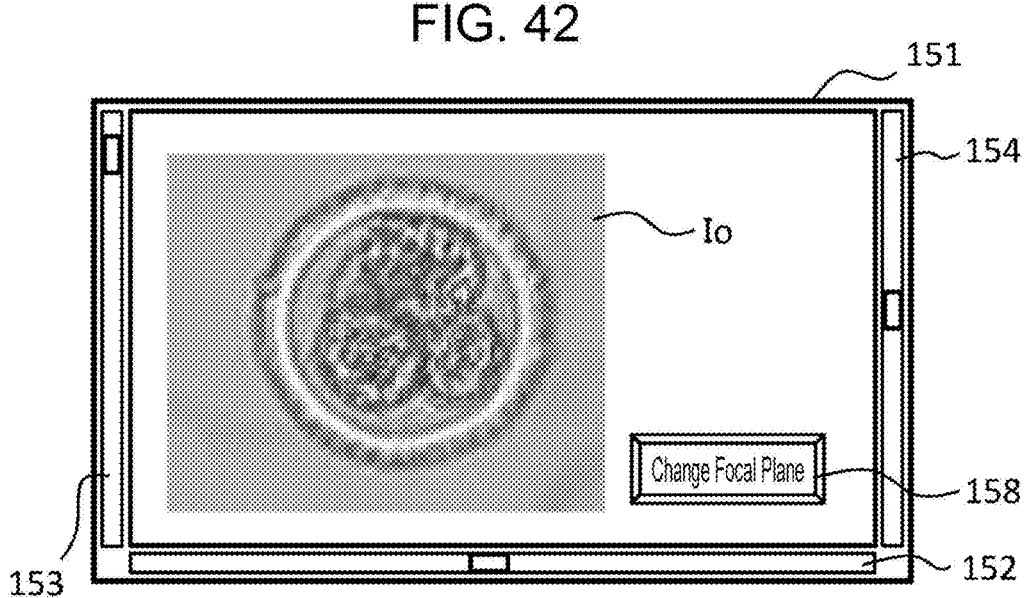
FIG. 42 is a diagram illustrating an example in which the optimum sectional image of the embryo is displayed using a photograph.

In step S6100, the optimum sectional image generation unit 290 generates, as an in-focus image, an optimum sectional image which is image data that can be output to a display or the like, on the basis of the result of the refocusing processing performed in step S6000, and displays the optimum sectional image on the display unit 150. FIGS. 41 and 42 illustrate an example of the optimum sectional image displayed on the display screen 151 of the display unit 150. FIG. 41 is a diagram illustrating an example in which the optimum sectional image of the embryo S is displayed on the display screen 151 of the display unit 150. FIG. 42 is a diagram illustrating an example in which the optimum sectional image of the embryo S is displayed using a photograph. FIG. 42 illustrates an example of the embryo S including four cells.

In step S6200, a focal plane change icon 158 is displayed on the display screen 151 together with an optimum sectional image Io of the embryo S. When the user of the image generation system 10A displays another sectional image of the embryo S, the user selects the focal plane change icon 158 via the CG operation input unit 140 to execute the associated instruction (yes in step S6200). If an instruction to change the displayed section from the optimum sectional image Io is not issued via the CG operation input unit 140 (no in step S6200), the optimum sectional image Io is kept displayed.

Figure 43:
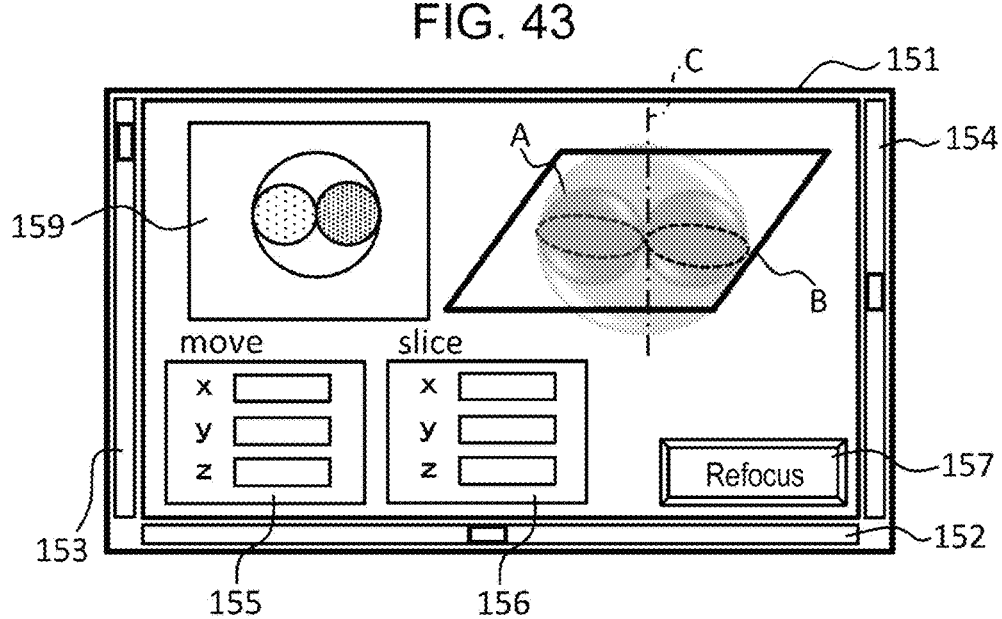
FIG. 43 is a diagram illustrating an example of a focal plane selection screen displayed on the display screen of the display unit.
Figure 44:
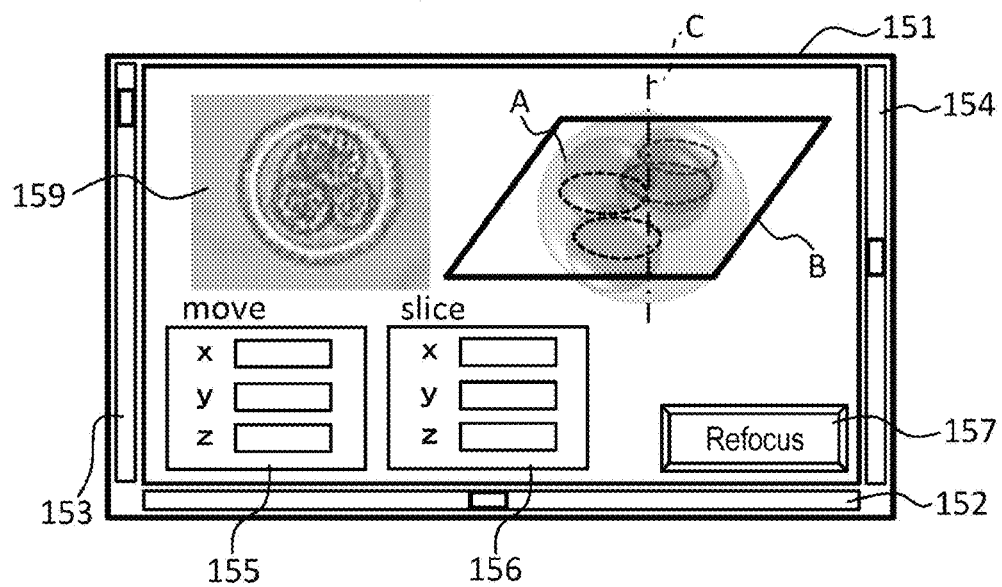
FIG. 44 is a diagram illustrating an example in which the focal plane selection screen is displayed using a photograph.

In step S6300, in response to executing an instruction associated with the focal plane change icon 158, the image operation unit 260 of the image generation device 200A displays a focal plane selection screen, such as ones illustrated in FIGS. 43 and 44, on the display screen 151 of the display unit 150. FIG. 43 is a diagram illustrating an example of the focal plane selection screen displayed on the display screen 151 of the display unit 150. FIG. 44 is a diagram illustrating an example in which the focal plane selection screen is displayed by using a photograph. FIG. 44 illustrates an example in which the embryo S includes four cells.

As in the first embodiment, the 3D model A of the embryo S defined using the xyz space, the horizontal movement scroll bar 152, the vertical movement scroll bar 153, the section movement scroll bar 154, the movement position display portion 155, the section position display portion 156, and the refocus icon 157 are displayed in the focal plane selection screen. The reference axis C that passes through the center of the 3D model A and the sectional plane B are displayed together with the 3D model A. The reference axis C can be rotated with respect to the center of the 3D model A, and the sectional plane B can be slid along the reference axis C via an operation of the CG operation input unit 140. Note that the 3D model A may be configured to rotate in a given manner and the sectional plane B may be configured to slide along the fixed reference axis C. In either case, the sectional plane B can represent a given section of the 3D model A. A detailed sectional image 159 of the embryo S at the sectional plane B is shown in the focal plane selection screen.

In step S6400, in response to execution of an instruction associated with the refocus icon 157 via an operation of the CG operation input unit 140 (yes in step S6400), the image operation unit 260 of the image generation device 200A determines the position of the displayed sectional plane B as the position of a section for which the detailed sectional image of the embryo S is to be displayed. The refocusing processing unit 220 and the in-focus image generation unit 230 of the image generation device 200A generate a detailed sectional image of the embryo S, which is an in-focus image obtained using the sectional plane B as the focal plane, and display the detailed sectional image on the display screen 151 (step S6500). The detailed sectional image of the embryo S may be generated in a manner similar to that performed by the sectional image generation unit 270 in the first embodiment; however, the detailed sectional image of the embryo S may be generated by performing the refocusing process by using photographic images stored in the storage unit 120 and using the sectional plane B as the focal plane. In addition, when an instruction associated with the refocus icon 157 is not executed (no in step S6400), the sectional image of the embryo S is kept displayed on the display screen 151 of the display unit 150.

The 3D model of the embryo S may be generated in a manner similar to that performed by the 3D image generation unit 250 in the first embodiment.

The following configuration is another example of the method for generating the 3D model A of the embryo S in the second embodiment.

The 3D image generation unit 250 obtains information regarding the position of the center C1 of the embryo S, the position of the center C2 of the first cell S1, and the position of the center C3 of the second cell S2 that are determined by the optimum section determination unit 280. The 3D image generation unit 250 further obtains, from the storage unit 120, photographic images obtained under illumination by the illuminators 101 that are located directly above or at positions closest to positions directly above the centers C1, C2, and C3 in a direction perpendicular to the light-receiving surface of the image sensor 102. Then, the 3D image generation unit 250 extracts an outline having the highest contrast, specifically, a circular outline, from each of the photographic images.

The outline extracted from a photographic image corresponding to illumination performed by the illuminator 101 located directly above or at a position closest to a position directly above the center C1 corresponds to an outline of a section that passes through the center of the embryo S, that is, the two-dimensional outline of the planar shape when the embryo S is viewed in a direction perpendicular to the light-receiving surface of the image sensor 102. In this way, the 3D image generation unit 250 identifies the spherical shape of the embryo S.

Likewise, the outline extracted from a photographic image corresponding to illumination performed by the illuminator 101 located directly above or at a position closest to a position directly above the center C2 corresponds to an outline of a section that passes through the center of the first cell S1, that is, the two-dimensional outline of the planar shape when the first cell S1 is viewed in a direction perpendicular to the light-receiving surface of the image sensor 102. In this way, the 3D image generation unit 250 identifies the spherical shape of the first cell S1.

The outline extracted from a photographic image corresponding to illumination performed by the illuminator 101 located directly above or at a position closest to a position directly above the center C3 corresponds to an outline of a section that passes through the center of the second cell S2, that is, the two-dimensional outline of the planar shape when the second cell S2 is viewed in a direction perpendicular to the light-receiving surface of the image sensor 102. In this way, the 3D image generation unit 250 identifies the spherical shape of the second cell S2.

Accordingly, the 3D image generation unit 250 generates the 3D model A of the embryo S on the basis of the center positions and the spherical shapes of the embryo S, the first cell S1, and the second cell S2. At that time, the 3D image generation unit 250 is capable of display the 3D model A of the embryo S in a translucent or transparent state in which arrangement of the first cell S1 and the second cell S2 can be checked.

2-3. Advantageous Effects

As described above, the image generation device 200A according to the second embodiment selects a section that includes the largest number of centers of cells, which are feature points of the embryo S that is an object to be imaged, and displays an in-focus image of the selected section. The displayed in-focus image of the section can show many features of the embryo S. Thus, the image generation device 200A is capable of automatically generating and providing useful information to the user.

First Modification of Embodiments

A first modification of the first and second embodiments will be described next. The first modification is a modification regarding the refocusing process performed by the image generation system. In the first and second embodiments described above, the illumination position is selected in step S1350 illustrated in FIG. 10; however, in the first modification, an image is selected. The first modification will be described below in terms of differences from the first and second embodiments.

Figure 45:
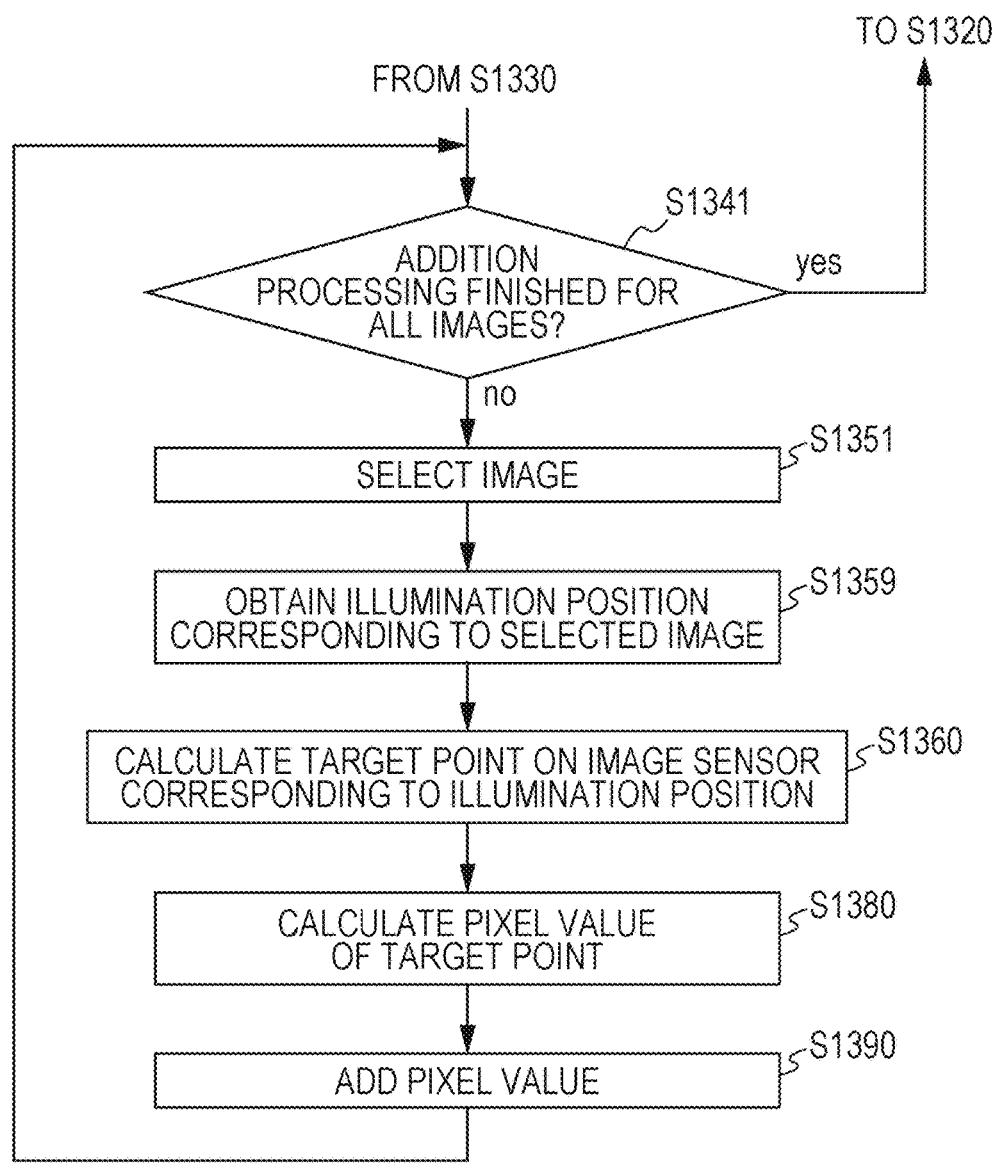
FIG. 45 is a flowchart illustrating an example of an operation of the refocusing processing unit according to a first modification of the first and second embodiments.

FIG. 45 is a flowchart illustrating an example of an operation of the refocusing processing unit 220 according to the first modification of the embodiments. In FIG. 45, steps S1341 to S1390 are performed instead of steps S1340 to S1390 illustrated in FIG. 10. In FIG. 45, steps that are substantially the same as those of FIG. 10 are denoted by the same reference signs, and a description thereof is omitted appropriately.

In FIG. 45, if all images are used in addition processing (yes in step S1341), the process returns to step S1320. On the other hand, if any of the images is not used in addition processing (no in step S1341), the process proceeds to step S1351. The refocusing processing unit 220 selects one of the images stored in the storage unit 120 (step S1351). In this step, an image that has not been used in addition processing is selected.

The refocusing processing unit 220 obtains, from the storage unit 120, illumination position information corresponding to the image selected in step S1351 (step S1359). The processing to be performed thereafter is substantially the same as that illustrated in FIG. 10 except that the operation of obtaining an image in step S1370 is omitted.

As described above, according to the refocusing processing method of the image generation system according to the first modification, pixel values of a plurality of images that correspond to each pixel of an in-focus image can be used for the pixel of the in-focus image as in the first and second embodiments even if selection of an illumination position is replaced with selection of an image. Consequently, a high-quality in-focus image of an object is successfully generated.

Second Modification of Embodiments

A second modification of the first and second embodiments will be described next. The second modification is a modification regarding the refocusing process performed by the image generation system. In the first and second embodiments described above, pixels of an in-focus image are sequentially selected in steps S1320 and S1330 of FIG. 10; however, pixels of a captured image are sequentially selected in the second modification. That is, the second modification differs from the first and second embodiments in that a pixel of the captured image is selected first and then a point on the focal plane corresponding to the selected pixel is determined. The pixel value of the selected pixel of the captured image is reflected for a pixel of an in-focus image that corresponds to the point on the focal plane thus determined. The second modification will be described below in terms of differences from the first and second embodiments.

Figure 46:
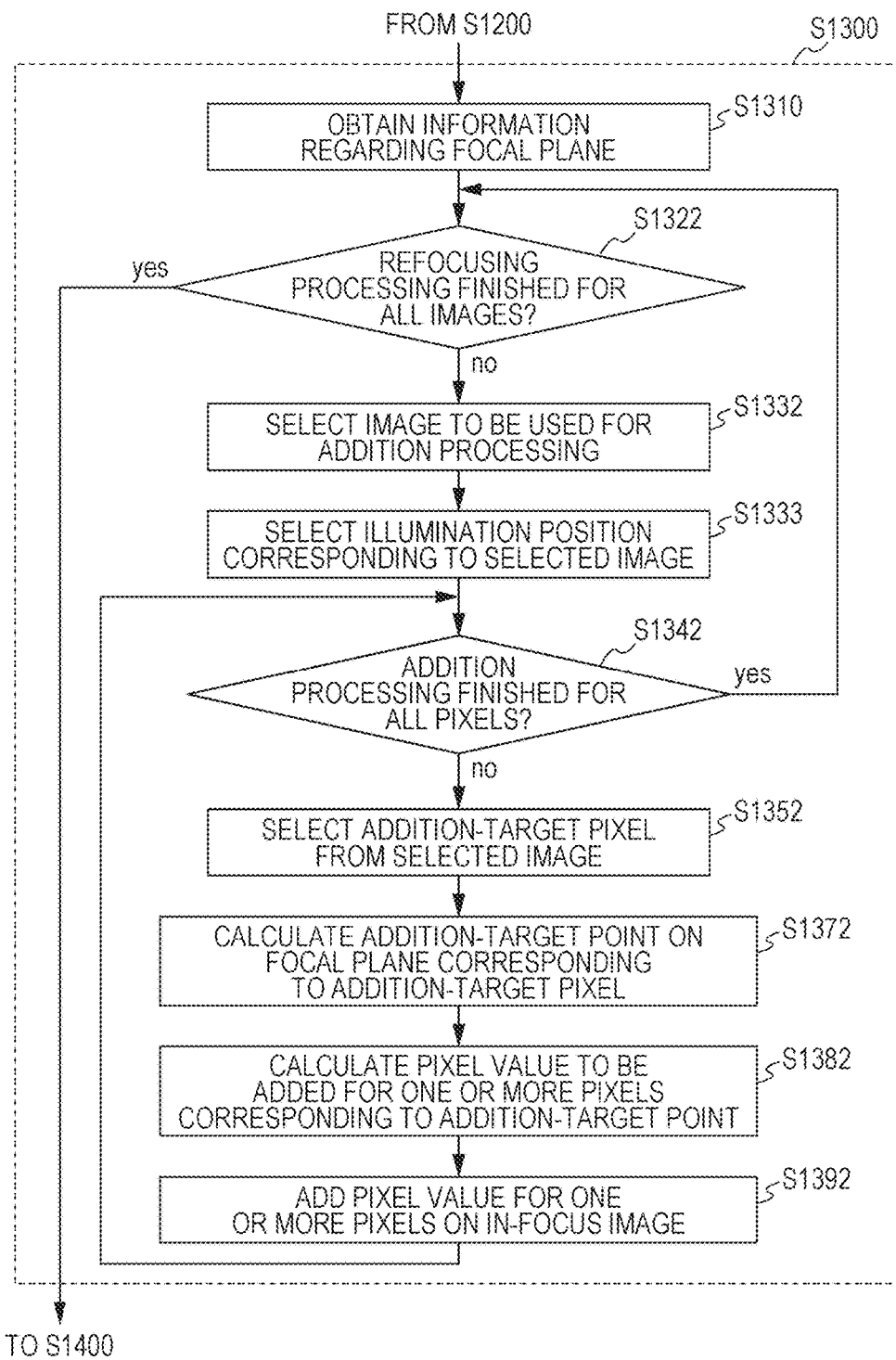
FIG. 46 is a flowchart illustrating an example of an operation of the refocusing processing unit according to a second modification of the first and second embodiments.

FIG. 46 is a flowchart illustrating an example of an operation of the refocusing processing unit 220 according to the second modification of the embodiments. In FIG. 46, steps that are substantially the same as those of FIG. 10 are denoted by the same reference signs, and a description thereof is omitted appropriately.

In step S1322, the refocusing processing unit 220 determines whether the refocusing processing has been finished for all the images captured in step S1100. The refocusing processing indicates processing from step S1322 to step S1392. If the refocusing processing has been finished for all the images (yes in step S1322), the process proceeds to step S1400. If the refocusing processing has not been finished for any of the images captured in step S1100 (no in step S1322), the process proceeds to step S1332.

In step S1332, the refocusing processing unit 220 selects a captured image from among the images captured in step S1100 and stored in the storage unit 120. A captured image selected in this step is an image that has not been subjected to the refocusing processing. Hereinafter, the image selected in step S1332 is referred to as a selected image.

In step S1333, the refocusing processing unit 220 obtains illumination position information corresponding to the selected image. For example, the refocusing processing unit 220 obtains illumination position information with reference to correspondences each between an image and illumination position information illustrated in FIG. 6. Here, the description will be given of the case where the position information regarding the illuminator 101a is obtained.

In step S1342, the refocusing processing unit 220 determines whether addition processing has been finished for all pixels of the selected image. If addition processing has been finished for all pixels of the selected image (yes in step S1342), the refocusing processing unit 220 finishes the addition processing, and the process returns to step S1322. On the other hand, if addition processing has not been finished for any of the pixels of the selected image (no in step S1342), the process proceeds to step S1352. The addition processing indicates processing from step S1342 to step S1392.

Figure 47:
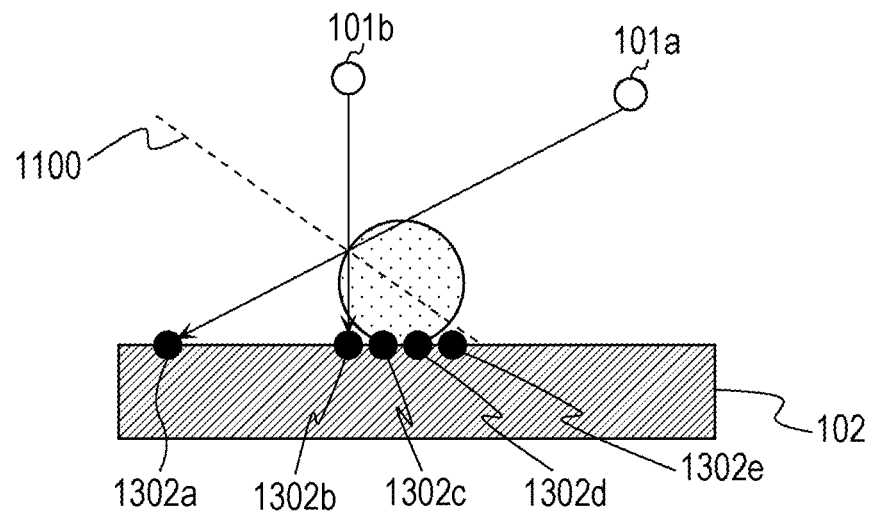
FIG. 47 is a schematic diagram for describing a specific example of a refocusing process according to the second modification of the first and second embodiments.
Figure 48:
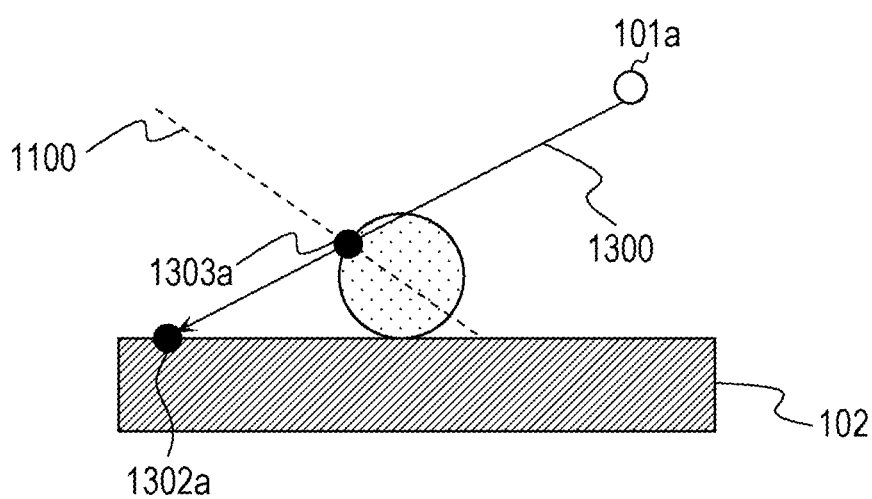
FIG. 48 is a schematic diagram for describing the specific example of the refocusing process according to the second modification of the first and second embodiments.
Figure 49:
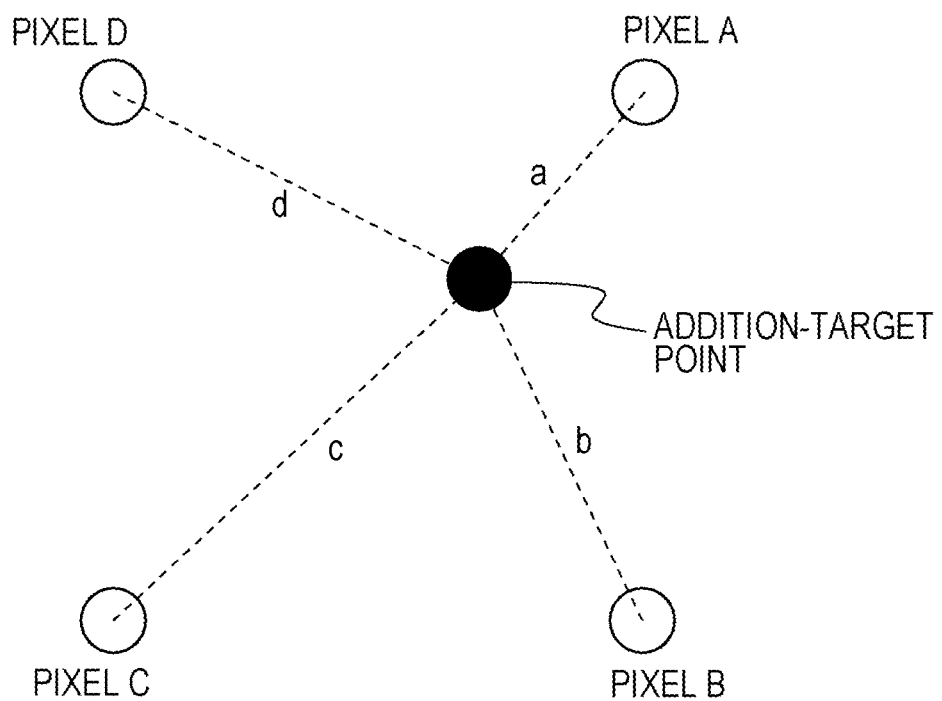
FIG. 49 is a schematic diagram for describing the specific example of the refocusing process according to the second modification of the first and second embodiments.

In step S1352, the refocusing processing unit 220 selects a pixel of the selected image. A pixel selected in this step is a pixel that has not been subjected to addition processing. FIG. 47 illustrates a plurality of points 1302a to 1302e on the light-receiving surface that correspond to a plurality of pixels included in the selected image. A description will be given of the case where a pixel corresponding to the point 1302a on the light-receiving surface is selected from the selected image as illustrated in FIG. 48. Hereinafter, the pixel selected in step S1352 is also referred to as an addition-target pixel.

In step S1372, the refocusing processing unit 220 calculates a position of an intersection point 1303a at which the focal plane 1100 crosses a line connecting the point 1302a on the light-receiving surface and the position of the illuminator 101a as illustrated in FIG. 48. Hereinafter, the intersection point 1303a is also referred to as an addition-target point.

In step S1382, the refocusing processing unit 220 calculates a pixel value of the addition-target pixel of the selected image that corresponds to the point 1302a on the light-receiving surface that is to be added to pixel value(s) of one or more pixels of the in-focus image that correspond to the addition-target point (intersection point 1303a) on the focal plane.

For example, if the position of the intersection point 1303a matches none of pixels (integer pixels) of the in-focus image, the refocusing processing unit 220 calculates a pixel value to be added for a plurality of pixels that are adjacent to the intersection point 1303a in the in-focus image. Specifically, the refocusing processing unit 220 determines the position in the in-focus image that corresponds to the addition-target point (intersection point 1303a) on the focal plane calculated in step S1372 on the basis of the arrangement of pixels of the in-focus image.

For example, a position surrounded by four pixels (pixels A to D) is determined to be the position of the addition-target point in the in-focus image. In this case, the refocusing processing unit 220 determines distances between the addition-target point and the respective pixels (pixels A to D) that are adjacent to the addition-target point in the in-focus image. The refocusing processing unit 220 calculates a pixel value to be added to each of the pixels adjacent to the addition-target point by using the calculated distances and the pixel value of the addition-target pixel. For example, the refocusing processing unit 220 calculates a pixel value to be added to each of the pixels so that a pixel whose distance to the addition-target point is relatively large in the in-focus image has a relatively large pixel value. Specifically, the refocusing processing unit 220 calculates a pixel value La to be added to the pixel A by using Equation 5 below, for example.

$$La = \frac{a \times L}{a+b+c+d} \quad \text{Equation 5}$$

In Equation 5, a denotes a distance between the pixel A and the addition-target point in the in-focus image, b denotes a distance between the pixel B and the addition-target point in the in-focus image, c denotes a distance between the pixel C and the addition-target point in the in-focus image, and d denotes a distance between the pixel D and the addition-target pixel in the in-focus image. In addition, L denotes a pixel value of the addition-target pixel of the captured image.

In step S1392, the refocusing processing unit 220 adds the pixel value calculated in step S1382 to pixel value(s) of one or more pixels of the in-focus image.

As a result of iteration of processing form step S1342 to step S1392, the pixel values of all the pixels of the selected image are successfully reflected to pixel values of the respective pixels of the in-focus image.

Further, addition processing is performed for all the pixels of the captured image as a result of iteration of processing from step S1322 to step S1392, and consequently the in-focus image at the focal plane is successfully generated.

Figure 50:
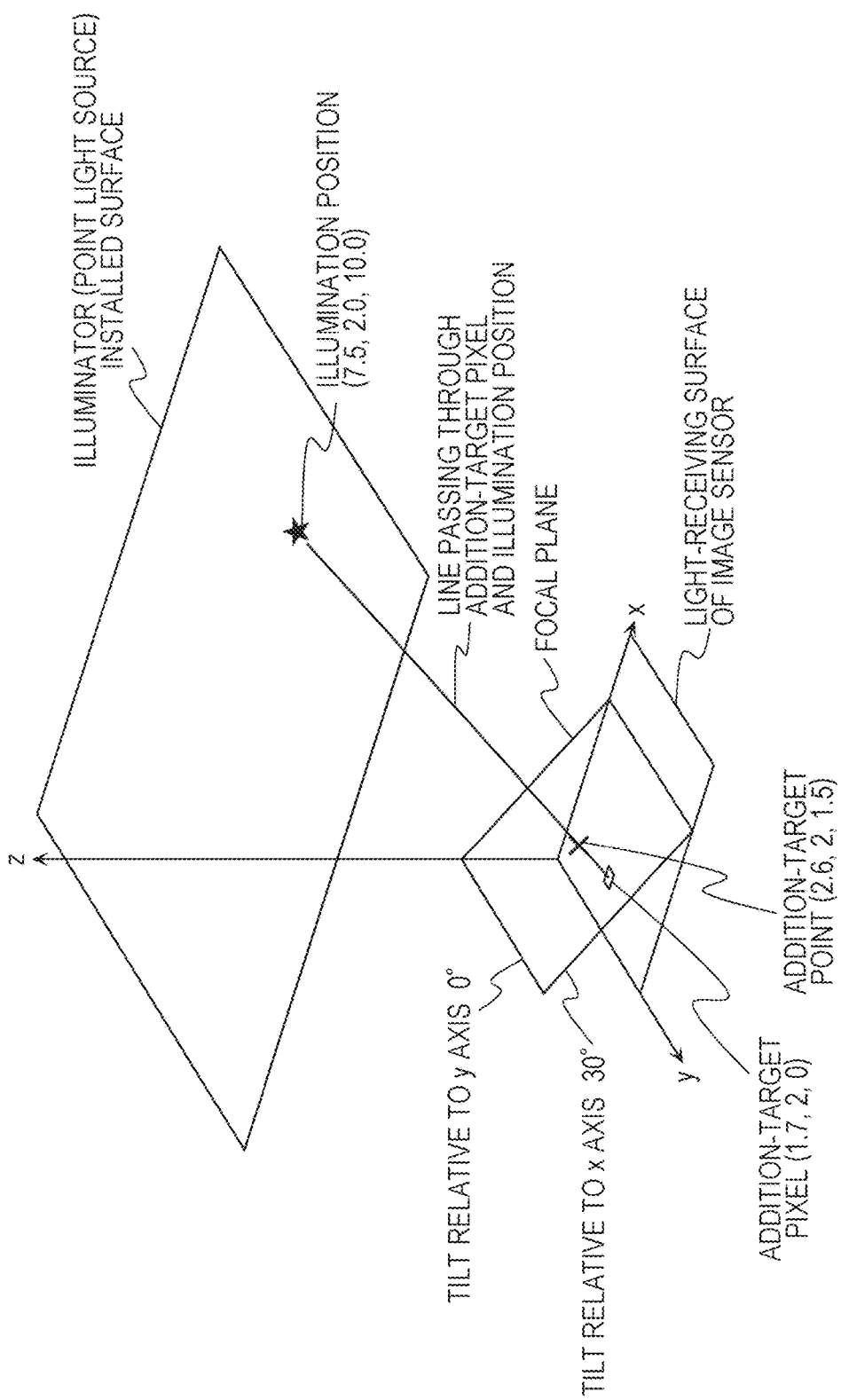
FIG. 50 is a schematic diagram for describing the specific example of the refocusing process according to the second modification of the first and second embodiments.

A specific example of the respective steps of the flowchart of FIG. 46 will be described with reference to FIG. 50. The description will be given of the case where the image sensor 102 and the focal plane satisfy the following conditions. The length of a longer side (i.e., a side parallel to the x axis) of the light-receiving surface of the image sensor 10 is 6 mm, whereas the length of a shorter side (i.e., a side parallel to the y axis) of the light-receiving surface is 4 mm. The focal plane is tilted with respect to the x axis by 30 degrees and with respect to the y axis by 0 degrees. An area of the focal plane is equal to an area of the light-receiving surface of the image sensor 102. That is, the focal plane is a rectangular plane of 6 mm×4 mm. One of the shorter sides of the focal plane extends in parallel to the y axis on the y-z plane as illustrated in FIG. 50, whereas the other shorter side of the focal plane extends in parallel to the y axis on the x-y plane with the x coordinate fixed to the position of approximately 5.2 mm. The coordinates (x, y, z) of the center of the focal plane are equal to (2.6, 2, 1.5).

It is assumed that an image is selected in step S1332, an illumination position (7.5, 2, 10) corresponding to the image is obtained in step S1333, and an addition-target pixel (1.7, 2, 0) is selected in step S1352. In this case, coordinates (2.6, 2, 1.5) of the addition-target point, which is an intersection point of the focal plane and a line that passes through the addition-target pixel (1.7, 2, 0) and the illumination position (7.5, 2.0, 10), are calculated. Then, the pixel value of the addition-target pixel is distributed and added to the pixel values of the pixels adjacent to the addition-target point in the in-focus image in step S1382.

As described above, according to the second modification, a pixel value of a first pixel of a captured image is applicable to pixel value(s) of one or more second pixels of an in-focus image that correspond to a position of an intersection point of a focal plane and a line connecting the position of the first pixel on the light-receiving surface of the image sensor 102 and the position of the illuminator. Accordingly, the pixel value of each pixel of the captured image is successfully reflected in a pixel value of the corresponding pixel of an in-focus image, and consequently, a high-quality in-focus image of an object is successfully generated.

Third Modification of Embodiments

A third modification of the first and second embodiments will be described next. The third modification is a modification regarding the image generation system. In the third modification, the illumination position is adaptively determined in accordance with a determined focal plane and an object is imaged by using an illuminator located at the determined illumination position, which is different from the first and second embodiments. The third modification will be described below in terms of differences from the first and second embodiments.

Configuration of Image Generation System

Figure 51:
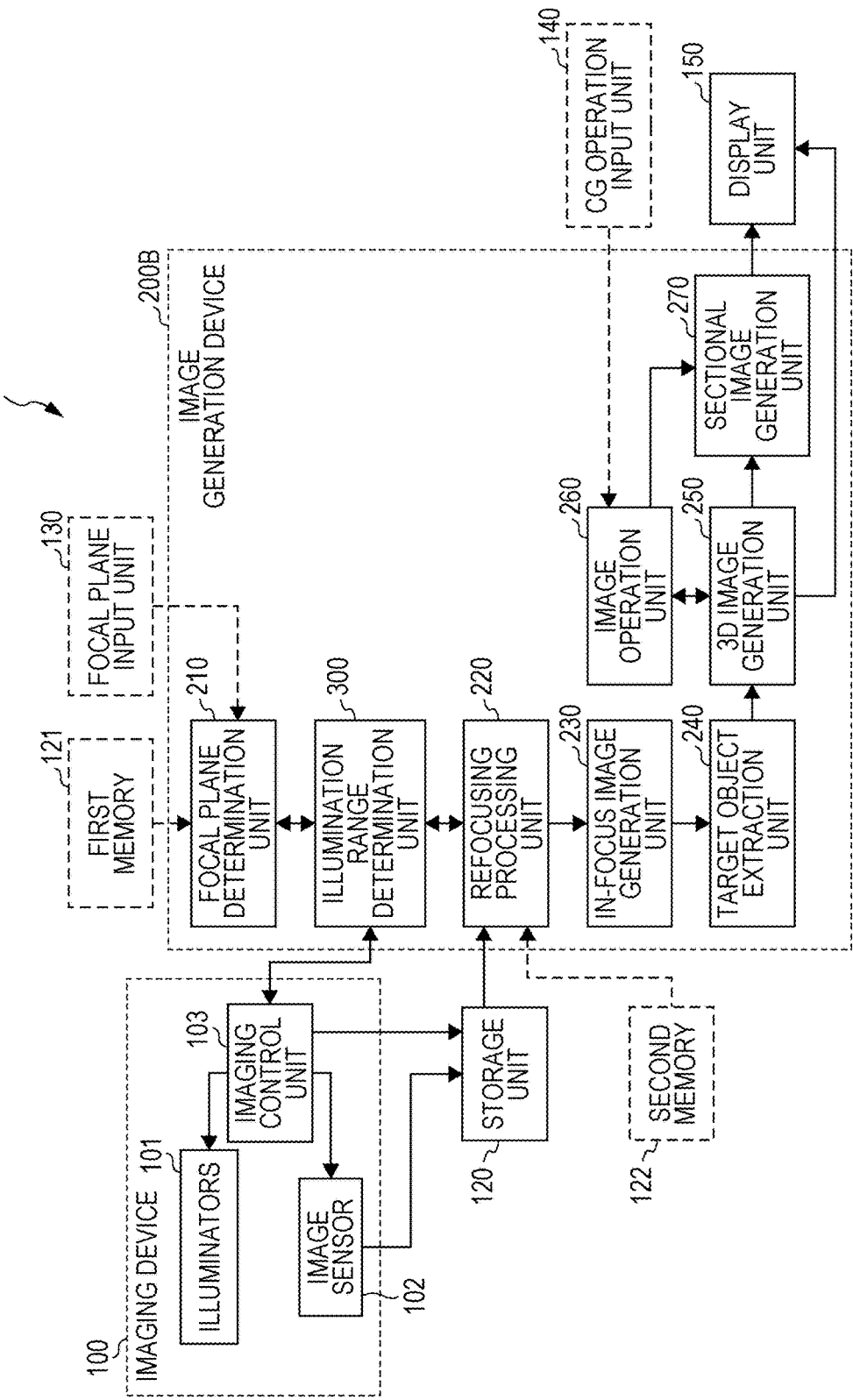
FIG. 51 is a block diagram illustrating an example of the functional configuration of an image generation system according to a third modification of the first and second embodiments.

FIG. 51 is a block diagram illustrating the functional configuration of an image generation system 10B according to the third modification. In FIG. 51, components that are substantially the same as those of FIG. 1 are denoted by the same reference signs, and a description thereof is omitted appropriately. The image generation system 10B includes the imaging device 100, an image generation device 200B, the storage unit 120, and the display unit 150.

Configuration of Imaging Device

The imaging device 100 includes the plurality of illuminators 101, the image sensor 102 that records, for each pixel, intensity of light, and the imaging control unit 103.

The imaging control unit 103 controls operations of the plurality of illuminators 101 and the image sensor 102 in accordance with illumination range information obtained from an illumination range determination unit 300 (described later). Specifically, the imaging control unit 103 causes the plurality of illuminators 101 located at different positions to sequentially radiate light. The imaging control unit 102 causes the image sensor 102 to capture an image of an object every time the object is irradiated with light by one of the plurality of illuminators 101.

Configuration of Image Generation Device

The image generation device 200B includes the focal plane determination unit 210, the illumination range determination unit 300, the refocusing processing unit 220, the in-focus image generation unit 230, the target object extraction unit 240, the 3D image generation unit 250, the image operation unit 260, and the sectional image generation unit 270.

The illumination range determination unit 300 determines the illumination position corresponding to the focal plane determined by the focal plane determination unit 210. A specific example of how the illumination position is determined will be described with reference to FIGS. 52 and 53.

Figure 52:
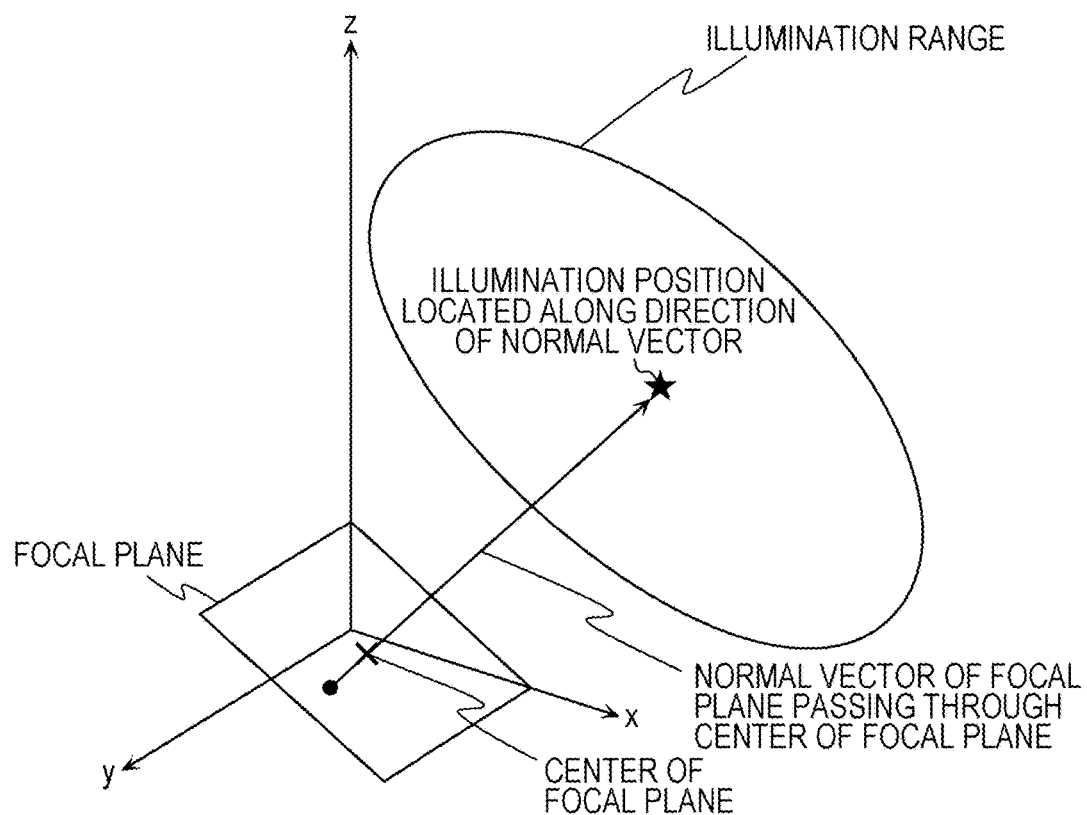
FIG. 52 is a diagram schematically illustrating an example of a range of the illumination position according to the third modification of the second embodiment.
Figure 53:
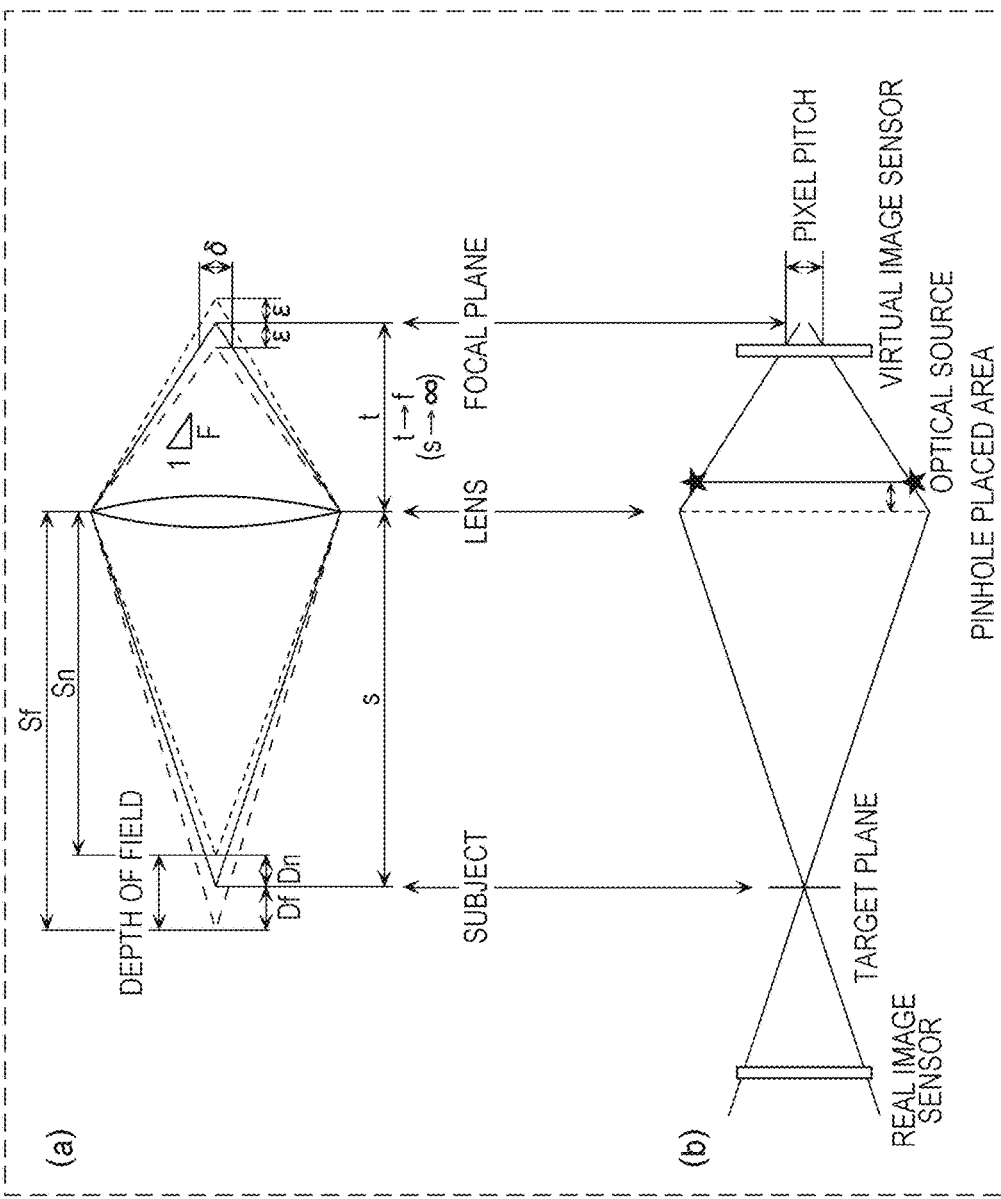
FIG. 53 is a schematic diagram in which a relationship between the focal length of a lens and the depth of field is associated with a relationship between arrangement of a point light source at the time of refocusing and the depth of field.

FIG. 52 is an explanatory diagram schematically illustrating a method for determining the illumination position in accordance with the third modification. FIG. 53 is a schematic diagram illustrating a correspondence between a relationship between the focal length of a lens and the depth of field and a relationship between arrangement of a point light source at the time of refocusing and the depth of field. FIG. 53(*a*) illustrates a relationship between the focal length of a lens and the depth of field, whereas FIG. 53(*b*) illustrates a relationship between arrangement of a point light source at the time of refocusing and the depth of field.

Referring to FIG. 53, f denotes the focal length of a lens, s denotes a distance to a subject, and t denotes a distance from the lens to an image plane. In addition, F denotes an F-number, ε denotes ½ of a depth of focus, and δ denotes the diameter of the permissible circle of confusion. Further, Sn denotes a near-point distance, Sf denotes a far-point distance, Dn denotes a near depth of field, and Df denotes a far depth of field.

The depth of field achieved by refocusing is determined in accordance with an extent of a illumination position distribution range. Referring to FIG. 53(*b*), the illumination position distribution range denoted by a dot line corresponds to the diameter of the lens in FIG. 53(*a*). In the case of the lens illustrated in FIG. 53(*a*), light reflected by the surface of a subject passes through the lens and forms an image on the focal plane. The depth of field is the sum of the near depth of field Dn and the far depth of field Df. Since refocusing is performed for imaging based on transmitted light in the present disclosure, the focal plane corresponds to the position of the subject illustrated in FIG. 53(*a*). In FIG. 53(*b*), the image sensor is located on the left side of the focal plane. In the third modification, the depth of field can be calculated by setting a pixel pitch of the image sensor as the permissible circle of confusion although nothing is located on the right side of the array of point light sources in FIG. 53(*b*).

For example, the range of the illumination position that is necessary to generate an in-focus image at the image plane illustrated in FIG. 52 corresponds to the size of the lens placed in parallel to the focal plane as illustrated in FIG. 53. The range of the illumination position of the case where observation of a subject located at the focal point requires a lens having a diameter of 10 mm that is apart from the subject by 5 mm is represented by the following circle. That is, the range of the illumination position is represented by a circle that is parallel to the focal plane, is apart from the focal plane by 5 mm, has the center at the intersection point of the normal that passes through the center of the focal plane and a plane parallel to the focal plane, and has a diameter of 10 mm. The position of the illuminator arranged in a region obtained by mapping this range of the illumination position onto a flat or curved surface on which the point light source is actually arranged (e.g., the curved surface illustrated in FIG. 3 or the flat surface illustrated in FIG. 4) is the illumination position that is determined to be suitable for the focal plane by the focal plane determination unit 210.

Operation of Refocusing Process of Image Generation System

Figure 54:
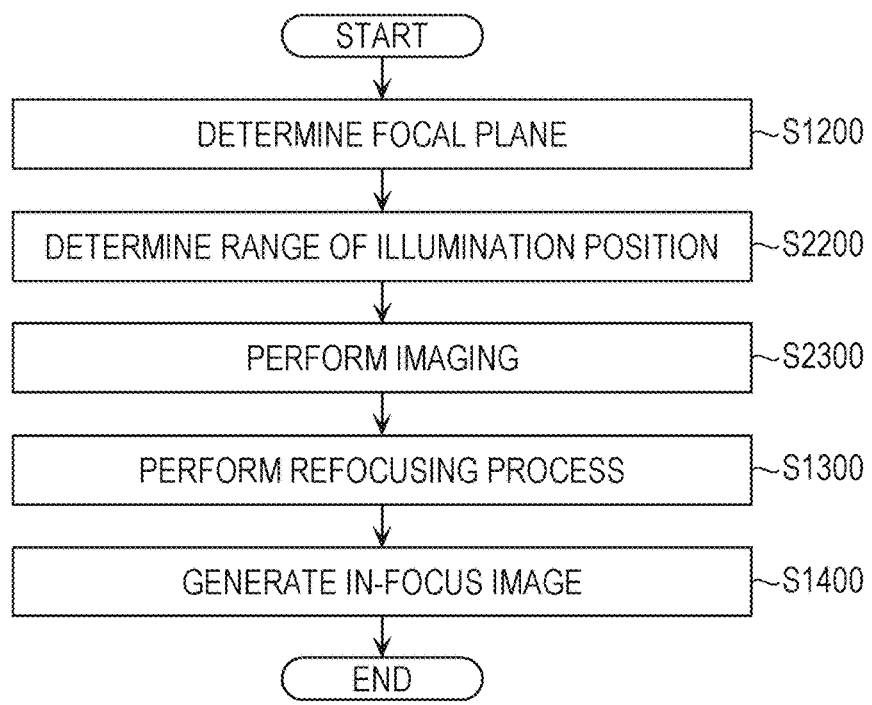
FIG. 54 is a flowchart illustrating an example of an operation of the image generation system according to the third modification of the second embodiment.

An operation of a refocusing process of the image generation system 10B thus configured will be described next. FIG. 54 is a flowchart illustrating an example of the operation of the refocusing process of the image generation system 10B according to the third modification. In FIG. 54, steps that are substantially the same as those of FIG. 7 are denoted by the same reference signs, and a description thereof is omitted appropriately.

As illustrated in FIG. 54, first, the focal plane determination unit 210 determines a focal plane (step S1200).

The illumination range determination unit 300 determines a range of the illumination position corresponding to the focal plane determined in step S1200 (step S2200).

The imaging device 100 irradiates an object with light by sequentially using illuminators corresponding to the range of the illumination position determined in step S2200 among the plurality of illuminators 101. The imaging device 100 records intensity of light that has received at the light-receiving surface of the image sensor 102 every time the object is irradiated with light by the corresponding illuminator to capture an image of the object. The captured image is stored in the storage unit 120 together with the position information of the illuminator used to irradiate the object with light during imaging (step S2300). Specifically, the imaging control unit 103 of the imaging device 100 selects two or more illuminators located in the determined range of the illumination position from among the plurality of illuminators 101 on the basis of the range of the illumination position determined in step S2200. The imaging control unit 103 then causes the two or more selected illuminators to sequentially irradiate the object with light in a predetermined order and causes the image sensor 102 to image the object. The imaging device 100 captures images of the object by using the illuminators located in the determined range of the illumination position by iterating irradiation of the object with light and imaging of the object. Since the following operation is substantially the same as that illustrated in FIG. 7 according to the first embodiment, a description thereof is omitted.

As described above, the image generation system according to the third modification is capable of determining a range of the illumination position on the basis of information regarding the focal plane and sequentially irradiating an object with light by using illuminators corresponding to the determined range of the illumination position. Accordingly, the object is successfully imaged by using illuminators suitable for generation of an in-focus image at the focal plane, and the time for imaging is successfully reduced.

Other Embodiments

While the image generation systems according to one or a plurality of aspects have been described on the basis of the embodiments and the modifications of the embodiments, the present disclosure is not limited to these embodiments and modifications. Embodiments achieved by applying various modifications conceived by a person skilled in the art to the embodiments and modifications and embodiments achieved by using elements of different embodiments in combination may also be within the scope of the one or plurality of aspects as long as these embodiments do not depart of the essence of the present disclosure.

The present disclosure can be widely employed in devices that generate an image of cultured cells or a cell mass, such as an embryo, and are useful when an object is imaged in an incubator.

What is claimed is:

1. An image generation device comprising:
a plurality of illuminators;
an image sensor including a plurality of sensor pixels, the image sensor having a surface on which an object is placed; and
a control circuit that generates a plurality of reference in-focus images each corresponding to one of a plurality of virtual reference focal planes that are located between the image sensor and the plurality of illuminators and generates a three-dimensional image of the object by using the plurality of reference in-focus images,
wherein the image sensor captures a plurality of images, each of the plurality of images being captured by using pixel values based on light received by the plurality of sensor pixels when a corresponding one of the plurality of illuminators irradiates the object with the light,
wherein each of the plurality of reference in-focus images includes a plurality of in-focus pixels,
wherein the control circuit
(a1) obtains the plurality of images captured by the image sensor,
(a2) obtains information regarding the plurality of virtual reference focal planes that pass through the object and are spaced apart from one another,
(a3) generates the plurality of reference in-focus images by obtaining pixel values of the sensor pixels corresponding to the plurality of in-focus pixels of the plurality of reference in-focus images by using the information regarding the plurality of virtual reference focal planes and the plurality of images,
(a4) extracts an outline of the object by using a reference in-focus image including an outline of the object having the highest contrast from among the plurality of reference in-focus images,
(a5) identifies a three-dimensional outline of the object on the basis of the extracted outline of the object,
(a6) generates a plurality of reference sectional images of the object by removing a region outside the three-dimensional outline from the plurality of reference in-focus images, and
(a7) generates the three-dimensional image of the object by using the plurality of reference sectional images and causes the three-dimensional image to be displayed on a display screen, and
wherein the control circuit calculates the pixel value of each of the plurality of in-focus pixels by using a pixel value of each of the sensor pixels that satisfy a relationship in which the position of one of the plurality of illuminators, the position of the in-focus pixel, and the position of the sensor pixel are on a line.

2. The image generation device according to claim 1, wherein
the control circuit
selects a section of the object in the displayed three-dimensional image of the object in accordance with an instruction externally input,
generates an image of the selected section of the object by using pixel values of a plurality of pixels of the plurality of reference in-focus images, the image of the selected section of the object including a plurality of section pixels, and
calculates a pixel value of each of the plurality of section pixels of the image of the selected section of the object by using a pixel value of a pixel of the reference in-focus image located at the section pixel or by using pixel values of pixels of the reference in-focus images located near the section pixel.

3. The image generation device according to claim 2, wherein the pixels of the reference in-focus images located near the section pixel that are used to calculate the pixel value of the section pixel are pixels of the reference in-focus images for two virtual reference focal planes having the section pixel interposed therebetween.

4. The image generation device according to claim 2,
wherein the control circuit generates a preview sectional image representing a section of the object for preview and causes the preview sectional image to be displayed on the display screen, the preview sectional image including a plurality of pixels, and
wherein the control circuit generates the preview sectional image by using, as a pixel value of each of the plurality of pixels of the preview sectional image, a pixel value of a pixel of the reference in-focus image located at the pixel of the preview sectional image.

5. The image generation device according to claim 1,
wherein the object is an embryo,
wherein the outline of the embryo included in the reference in-focus image is circular, and
wherein the three-dimensional outline of the embryo is spherical.

6. An image generation method for generating an image of an object placed on an image sensor, comprising:
(b1) capturing a plurality of images, each of the plurality of images being captured by using pixel values based on light received by a plurality of sensor pixels of the image sensor when a corresponding one of a plurality of illuminators irradiates the object with the light;
(b2) setting a plurality of virtual reference focal planes between the image sensor and the plurality of illuminators, the plurality of virtual reference focal planes passing through the object and being spaced apart from one another;
(b3) generating a plurality of reference in-focus images each corresponding to one of the plurality of virtual reference focal planes by obtaining pixel values of the sensor pixels corresponding to a plurality of in-focus pixels of the plurality of reference in-focus images by using information regarding the plurality of virtual reference focal planes and the plurality of captured images;
(b4) extracting an outline of the object by using a reference in-focus image including an outline of the object having the highest contrast from among the plurality of reference in-focus images;
(b5) identifies a three-dimensional outline of the object on the basis of the extracted outline of the object;
(b6) generating a plurality of reference sectional images of the object by removing a region outside the three-dimensional outline of the object from the plurality of reference in-focus images; and
(b7) generating a three-dimensional image of the object by using the plurality of reference sectional images and causing the three-dimensional image to be displayed on a display screen,
at least one of (b1) to (b7) being performed by a control circuit,
wherein the pixel value of each of the plurality of in-focus pixels is calculated by using a pixel value of each of the sensor pixels that satisfy a relationship in which the position of one of the plurality of illuminators, the position of the in-focus pixel, and the position of the sensor pixel are on a line.

7. The image generation method according to claim 6, further comprising:
(c1) selecting a section of the object in the three-dimensional image of the object;
(c2) generating an image of the selected section of the object by using pixel values of a plurality of pixels of the plurality of reference in-focus images, the image of the selected section of the object including a plurality of section pixels; and
(c3) calculating a pixel value of each of the plurality of section pixels of the image of the selected section of the object by using a pixel value of a pixel of the reference in-focus image located at the section pixel or by using pixel values of pixels of the reference in-focus images located near the section pixel.

8. The image generation method according to claim 7, wherein in the calculating of a pixel value of each of the plurality of section pixels, pixels of the reference in-focus images for two virtual reference focal planes having the section pixel interposed therebetween are used as the pixels of the reference in-focus images located near the section pixel.

9. The image generation method according to claim 7, further comprising:
(d1) generating a preview sectional image representing a section of the object for preview and causing the preview sectional image to be displayed on the display screen, the preview sectional image including a plurality of pixels,
wherein in the generating of the preview sectional image, as a pixel value of each of the plurality of pixels of the preview sectional image, a pixel value of a pixel of the reference in-focus image located at the pixel of the preview sectional image is used.

10. The image generation method according to claim 6,
wherein the object is an embryo,
wherein the outline of the embryo included in the reference in-focus image is circular, and
wherein the three-dimensional outline of the embryo is spherical.

11. A non-transitory computer-readable recording medium storing a control program that causes a device including a processor to perform a process, the process comprising:
(e1) capturing, using an image sensor, a plurality of images of an object placed on the image sensor, each of the plurality of images being captured by using pixel values based on light received by a plurality of sensor pixels of the image sensor when a corresponding one of a plurality of illuminators irradiates the object with the light;
(e2) setting a plurality of virtual reference focal planes between the image sensor and the plurality of illuminators, the plurality of virtual reference focal planes passing through the object and being spaced apart from one another between the image sensor and the plurality of illuminators;
(e3) generating a plurality of reference in-focus images each corresponding to one of the plurality of virtual reference focal planes by obtaining pixel values of the sensor pixels corresponding to a plurality of in-focus pixels of the plurality of reference in-focus images by using information regarding the plurality of virtual reference focal planes and the plurality of captured images;

(e4) extracting an outline of the object by using a reference in-focus image including an outline of the object having the highest contrast from among the plurality of reference in-focus images;

(e5) identifying a three-dimensional outline of the object on the basis of the extracted outline of the object;

(e6) generating a plurality of reference sectional images of the object by removing a region outside the three-dimensional outline of the object from the plurality of reference in-focus images; and (e7) generating a three-dimensional image of the object by using the plurality of reference sectional images and causing the three-dimensional image to be displayed on a display screen, and wherein the pixel value of each of the plurality of in-focus pixels is calculated by using a pixel value of each of the sensor pixels that satisfy a relationship in which the position of one of the plurality of illuminators, the position of the in-focus pixel, and the position of the sensor pixel are on a line.

12. A processor-implemented method, comprising:

causing a first illuminator to irradiate an object with light and causing an image sensor to image the object during the irradiation by the first irradiator to capture a first image;

causing a second illuminator to irradiate the object with light after the irradiation by the first irradiator and causing the image sensor to image the object during the irradiation by the second illuminator to capture a second image;

calculating sets of pixel values included in reference in-focus images at virtual reference focal planes, the virtual reference focal planes including virtual sections of the object, the sets of pixel values and the reference in-focus images having a one-to-one correspondence, the reference in-focus images and the virtual reference focal planes having a one-to-one correspondence, the virtual reference focal planes and the virtual sections having a one-to-one correspondence;

determining outlines of the object included in the reference in-focus images, the reference in-focus images and the outlines having a one-to-one correspondence, each of the outlines being determined by detecting a circle in a corresponding one of the reference in-focus images;

selecting one of the outlines by detecting contrasts corresponding to the respective outlines, the contrast of the selected outline being the highest among the detected contrasts;

generating a three-dimensional image of the object by using the selected outline but not using one or a plurality of unselected outlines among the detected outlines; and causing a display to display the three-dimensional image, wherein calculation of a pixel value, provided by a virtual pixel, included in a set of pixel values included in the sets includes:

determining a first intersection point of a first line and the image sensor, the first line including a point included in the first illuminator and a point included in the virtual pixel;

determining a first pixel providing a first pixel value included in the first image, the first pixel is the closest to the first intersection point than any other pixels included in the image sensor;

determining a second intersection point of a second line and the image sensor, the second line including a point included in the second illuminator and the point included in the virtual pixel;

determining a second pixel providing a second pixel value included in the second image, the second pixel is the closest to the second intersection point than any other pixels included in the image sensor; and calculating the pixel value based on the first pixel value, the second pixel value, a distance between the virtual pixel and the first pixel, and a distance between the virtual pixel and the second pixel.

* * * * *